United States Patent
Zhao et al.

(10) Patent No.: US 11,077,187 B2
(45) Date of Patent: Aug. 3, 2021

(54) EPITOPE OF OPTIMIZED HUMANIZED MONOCLONAL ANTIBODIES AGAINST ACTIVATED PROTEIN C AND USES THEREOF

(71) Applicant: OKLAHOMA MEDICAL RESEARCH FOUNDATION, Oklahoma City, OK (US)

(72) Inventors: Xiao-Yan Zhao, Union City, CA (US); Andreas Wilmen, Cologne (DE); Christoph Freiberg, Wuppertal (DE); Lars Linden, Gevelsberg (DE); Ji-Yun Kim, Berkeley, CA (US); Subramanian Yegneswaran, Pleasanton, CA (US); Karin Regnstrom, San Francisco, CA (US); Ursula Egner, Berlin (DE); Xinquan Wang, Beijing (CN)

(73) Assignee: OKLAHOMA MEDICAL RESEARCH FOUNDATION, Oklahoma City, OK (US)

(*) Notice: Subject to any disclaimer, the term of this patent is extended or adjusted under 35 U.S.C. 154(b) by 108 days.

(21) Appl. No.: 15/775,056

(22) PCT Filed: Nov. 15, 2016

(86) PCT No.: PCT/US2016/062047
§ 371 (c)(1),
(2) Date: May 10, 2018

(87) PCT Pub. No.: WO2017/087391
PCT Pub. Date: May 26, 2017

(65) Prior Publication Data
US 2018/0326053 A1 Nov. 15, 2018

Related U.S. Application Data

(60) Provisional application No. 62/256,582, filed on Nov. 17, 2015.

(51) Int. Cl.
| | |
|---|---|
| *C07K 16/40* | (2006.01) |
| *A61K 39/395* | (2006.01) |
| *A61K 39/00* | (2006.01) |
| *A61P 7/04* | (2006.01) |

(52) U.S. Cl.
CPC .......... *A61K 39/3955* (2013.01); *A61K 39/00* (2013.01); *A61P 7/04* (2018.01); *C07K 16/40* (2013.01); *A61K 2039/505* (2013.01); *C07K 2317/24* (2013.01); *C07K 2317/34* (2013.01); *C07K 2317/55* (2013.01); *C07K 2317/567* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 5,202,253 A | 4/1993 | Esmon et al. | |
| 5,279,956 A | 1/1994 | Griffin et al. | |
| 5,679,639 A * | 10/1997 | Griffin | C07K 14/755 514/13.7 |
| 6,838,437 B2 | 1/2005 | Kaufman et al. | |
| 6,953,568 B1 | 10/2005 | Esmon et al. | |
| 6,989,241 B2 | 1/2006 | Esmon et al. | |
| 7,244,430 B2 | 7/2007 | Throsby et al. | |
| 7,247,453 B1 | 7/2007 | Rezaie et al. | |
| 7,879,322 B2 | 2/2011 | Kneissel et al. | |
| 8,039,597 B2 | 10/2011 | Raitano et al. | |
| 8,153,766 B2 * | 4/2012 | Xu | C07K 16/40 530/388.23 |
| 9,127,072 B2 * | 9/2015 | Xu | A61P 37/00 |
| 9,657,111 B2 * | 5/2017 | Zhao | G01N 33/573 |
| 2009/0068178 A1 | 3/2009 | Crowley et al. | |
| 2009/0110683 A1 | 4/2009 | Xu et al. | |
| 2010/0028910 A1 | 2/2010 | Griffin et al. | |
| 2010/0291106 A1 | 11/2010 | Etemad-Gilbertson et al. | |
| 2012/0164150 A1 | 6/2012 | Xu et al. | |
| 2015/0307625 A1 | 10/2015 | Zhao et al. | |

FOREIGN PATENT DOCUMENTS

| | | |
|---|---|---|
| EP | 1544214 | 6/2005 |
| JP | 2006-197930 | 8/2006 |
| JP | 2014-237651 | 12/2014 |
| WO | WO 1993/000102 | 1/1993 |
| WO | WO 1996/005303 | 2/1996 |
| WO | WO 2002/029015 | 4/2002 |
| WO | WO 2003/091415 | 11/2003 |

(Continued)

OTHER PUBLICATIONS

Janeway et al., Immunobiology, 3rd edition, 1997 Garland Publishing Inc., pp. 3:1-3:11.*
Rudikoff et al., Proc Natl Acad Sci USA. Mar 1982. 79(6):1979-83.*
Edwards et al., J Mol Biol. Nov. 14, 2003;334(1):103-18.*
Lloyd et al., Protein Eng Des Sei. Mar. 2009;22(3):159-68. doi: 10.1093/protein/gzn058. Epub Oct. 29, 2008.*
Goel et al., J Immunol. Dec. 15, 2004;173(12)7358-67.*
Kanyavuz et al., Nat Rev Immunol. Jun. 2019;19(6):355-368. doi: 10.1038/S41577-019-0126-7.*
Zhao et al. Nat Commun. Jun. 12, 2020;11(1):2992. doi: 10.1038/S41467-020-16720-9.*

(Continued)

*Primary Examiner* — Michael Szperka
(74) *Attorney, Agent, or Firm* — Parker Highlander PLLC

(57) ABSTRACT

Provided are optimized humanized antibodies that selectively bind to and inhibit activated protein C without binding to or inhibiting unactivated protein C. In particular, the antibodies bind to particular epitopes outside the catalytic triad of the active site of human activated protein C. Methods of treatment employing these antibodies are described herein.

17 Claims, 20 Drawing Sheets

Specification includes a Sequence Listing.

(56) References Cited

FOREIGN PATENT DOCUMENTS

| WO | WO-2004041862 A2 * | 5/2004 | ............ A61P 43/00 |
|---|---|---|---|
| WO | WO 2004/073656 | 9/2004 | |
| WO | WO 2006/052591 | 5/2006 | |
| WO | WO 2007/070750 | 6/2007 | |
| WO | WO 2007/076524 | 7/2007 | |
| WO | WO 2008/021156 | 2/2008 | |
| WO | WO 2009/055669 | 4/2009 | |
| WO | WO 2012/007516 | 1/2012 | |
| WO | WO-2014085527 A1 * | 6/2014 | ............ C07K 16/40 |
| WO | WO-2014085596 A1 * | 6/2014 | ............ A61K 45/06 |
| WO | WO-2015179435 A1 * | 11/2015 | ............ C07K 16/36 |

OTHER PUBLICATIONS

Brown et al., "Identification and purification of vitamin K-dependent proteins and peptides with monoclonal antibodies specific for gamma-carboxyglutamyl (Gla) residues," *J. Biol. Chem.*, 275(26):19795-802, 2000.

Cheng et al., "Activated protein C blocks p53-mediated apoptosis in ischemic human brain endothelium and is neuroprotective," *Nature Medicine*, 9(3):338-342, 2003.

Chognot et al., "Identification of protein C epitopes altered during its nanoencapsulation," *Journal of Protein Chemistry*, 18:779-784, 1999.

Extended European Search Report issued in European Patent Application No. 13857737.4, dated Jun. 10, 2016.

Gale et al., "Nonenzymatic anticoagulant activity of the mutant serine protease Ser360Ala-activated protein C mediated by factor Va," *Protein Science*, 6(1):132-140, 1997.

Gale et al., "The autolysis loop of activated protein C interacts with factor Va and differentiates between the Arg506 and Arg306 cleavage sites," *Blood*, 96(2):585-593, 2000.

Green, "Antibody engineering via genetic engineering of the mouse: XenoMouse strains are a vehicle for facile generation of therapeutic human monoclonal antibodies," *J. Immunological Methods*, 231:11-23, 1999.

Hosac, "Drotrecogin alfa (activated): the first FA-approved treatment for severe sepsis," *BUMC Proceedings*, 15:224-227, 2002.

Hwang et al., "A thrombin-cross-reactive anticardiolipin antibody binds to and inhibits the anticoagulant function of Activated Protein C," *Arthritis & Rheumatism*, 48(6):1623-1630, 2003. .

Liaw et al., "A monoclonal antibody against activated protein C allows rapid detection of activated protein C in plasma and reveals a calcium ion dependent epitope involved in factor Va inactivation," *Journal of Thomrobsis and Haemostasis*, 1(4):662-670, 2003.

Liaw et al., "Identification of the Protein C/Activated Protein C Binding Sites on the Endothelial Cell Protein C Receptor," *The Journal of Biological Chemistry*, 276(11):8364-8370, 2001.

Lloyd et al., "Modelling the human immune response: performance of a $10^{11}$ human antibody repertoire against a broad panel of therapeutically relevant antigens," *Protein Engineering, Design & Selection*, 22(3):159-168, 2009.

Mosnier et al., "Activated protein C variants with normal cytoprotective but reduced anticoagulant activity," *Blood*, 104:1740-1744, 2004.

Office Communication issued in Australian Patent Application No. 2013202464, dated Jul. 29, 2014.

Office Communication issued in Japanese Patent Application No. 2015-545419, dated Aug. 29, 2017. (English translation of Japanese text).

Office Communication issued in Japanese Patent Application No. 2012-263561, dated Mar. 5, 2014. (English translation of Japanese text).

Office Communication issued in Japanese Patent Application No. 2014-136566, dated Sep. 30, 2015. (English translation of Japanese text).

Office Communication issued in Korean Patent Application No. 10-2010-7011548, dated Mar. 16, 2016. (English translation of Korean text).

Office Communication issued in Russian Patent Application No. 2010121148/10, dated Apr. 7, 2014. (English translation of Russian patent document).

Office Communication issued in U.S. Appl. No. 12/257,706, dated Jun. 24, 2010.

Office Communication issued in U.S. Appl. No. 12/257,706, dated Nov. 15, 2010.

Office Communication issued in U.S. Appl. No. 12/257,706, dated Oct. 18, 2011.

Office Communication issued in U.S. Appl. No. 12/257,706, dated Mar. 15, 2011.

Office Communication issued in U.S. Appl. No. 14/443,696, dated Aug. 29, 2016.

Office Communication issued in U.S. Appl. No. 13/306,301, dated May 8, 2015.

Office Communication issued in U.S. Appl. No. 13/306,301, dated Jan. 26, 2015

Office Communication issued in U.S. Appl. No. 13/306,301, dated Sep. 11, 2014.

Office Communication issued in U.S. Appl. No. 14/734,055, dated May 4, 2018.

Office Communication issued in U.S. Appl. No. 14/734,055, dated Sep. 20, 2017.

Owens and Young, "The genetic engineering of monoclonal antibodies," *J. Immunological Methods*, 168:149-165, 1994.

PCT International International Search Report and Written Opinion issued in International Application No. PCT/US2016/062047, dated Feb. 3, 2017.

PCT International International Search Report and Written Opinion issued in International Patent Application No. PCT/US2013/072243, dated Mar. 10, 2014.

PCT International Partial Search Report issued in Application No. PCT/US2008/081110, dated Feb. 16, 2009.

PCT International Search Report and Written Opinion issued in Application No. PCT/US2008/081110, dated Jul. 8, 2009.

PCT International Search Report and Written Opinion issued in International Patent Application No. PCT/US2013/072137, dated Feb. 21, 2014.

Preston et al., "Multifunctional specificity of the protein C/activated protein C Gla domain," *J. Biol. Chem.*, 281(39):28850-7, 2006.

Preston et al., "Selective modulation of protein C affinity for EPCR and phospholipids by Gla domain mutation," *FEBS J.*, 727(1):97-108, 2004.

Rezaie and Esmon, "The function of calcium in protein C activation by thrombin and the thrombin-thrombomodulin complex can be distinguished by mutational analysis of protein C derivatives," *J. Biol. Chem.*, 267:26104-26109, 1992.

Stearns-Kurosawa et al., "The endothelial cell protein C receptor augments protein C activation by the thrombin-thrombomodulin complex" *Proc. Natl. Acad. Sci. USA*, 93:10212-10216, 1996.

The Merck Manuals Online Medical Library. [Online]. Whitehouse Station, NJ; Merck Research Laboratories, 2006-2007. [Retrieved on Nov. 19, 2007]. Retrieved from the Internet: <URL: http://www.merck.com/mmpe/print/sec06/ch068/ch068a.html>. Sepsis and Septic Shock. See pp. 1-5.

Xu et al., "Reconstitution of the Human Endothelial Cell Protein C Receptor with Thrombomodulin in Phosphatidylcholine Vesicles Enhances Protein C Activation," *The Journal of Biological Chemistry*, 274(10): 6704-6710, 1999.

Zhang and Castellino, "Generation of an antibody with a designed specificity difference for protein C and activated protein C," *J. Protein Chem.*, 8(4):471-480, 1989. (Abstract only).

Zhao et al., "Targeted Inhibition of Activated Protein C Anticoagulant Activity By Monoclonal Antibody HAPC1573 for Treatment of Hemophilia," *Blood*, 128(22):80, 2016.

\* cited by examiner

EPITOPE OF OPTIMIZED HUMANIZED MONOCLONAL ANTIBODIES AGAINST ACTIVATED PROTEIN C AND USES THEREOF

This application is a national phase application under 35 U.S.C. § 371 of International Application No. PCT/US2016/062047, filed Nov. 15, 2016, which claims priority to U.S. Provisional Patent Application No. 62/256,582, filed Nov. 17, 2015. The entire contents of each are incorporated herein by reference in their entirety.

Pursuant to 37 C.F.R. 1.821(c), a sequence listing is submitted herewith as an ASCII compliant text file named "BAOMP0133US_ST25.txt", created on May 3, 2018 and having a size of ~79 kilobytes. The content of the aforementioned file is hereby incorporated by reference in its entirety.

BACKGROUND

Blood coagulation is a process consisting of a complex interaction of various blood components, or factors, which eventually give rise to a fibrin clot. Generally, blood components participating in the coagulation "cascade" are proenzymes or zymogens-enzymatically inactive proteins that are converted into an active form by action of an activator. Regulation of blood coagulation is largely accomplished enzymatically by proteolytic inactivation of the pro-coagulation factors Va and VIIIa achieved by activated protein C (aPC) (Esmon, 1989).

Protein C is the precursor to aPC, a potent natural anticoagulant. Protein C is activated by thrombin in complex with thrombomodulin (TM). The activation is augmented by endothelial cell protein C receptor (EPCR). TM and EPCR can be down-regulated due to inflammatory mediators, such as tumor necrosis factor, reviewed by Esmon (1999). TM and EPCR have also been found to be reduced in some forms of septic shock, meningococcemia in particular. Since EPCR and TM are expressed on endothelium, it is not possible to directly determine how well they are functioning without removal of blood vessels.

aPC functions as an anticoagulant by proteolytically cleaving and downregulating pro-coagulant factors. aPC also serves important functions as an anti-apoptosis agent, an anti-inflammatory molecule and a cytoprotectant. Bleeding disorders where homeostatis is dysregulated through a loss of a key factor, such as the absence of Factor VIII in hemophilia, or in trauma patients where the wound process results in a temporary loss of hemostasis, can be treated by the removal of aPC. Such treatment, however, could result in unwanted detrimental consequences of removing the beneficial functions of aPC in addition to the removal of the anti-coagulant activity. Therefore it is desirable to have a therapeutic that selectively targets the anti-coagulant activity of aPC while leaving other functions of the molecule intact.

SUMMARY

Thus, there are provided antibodies that selectively target the anti-coagulant activity of aPC. Provided is a humanized IgG2 antibody comprising (a) a heavy chain comprising heavy chain CDRs represented by (i) SEQ ID NOS: 2 or 16, (ii) SEQ ID NOS: 3, 17 or 31 and (iii) SEQ ID NOS: 4 or 46; and (b) a light chain comprising light chain CDRs represented by (i) SEQ ID NO: 6, (ii) SEQ ID NO: 7 and (iii) SEQ ID NOS: 8.

The heavy chain of an antibody provided herein may comprise a framework of a VH1C heavy chain, VH3-72 heavy chain, VH3-7 heavy chain, VH3-72 heavy chain, VH3-7(del RL) heavy chain or VH3-48 heavy chain. The light chain of an antibody provided herein may comprise a framework of a VK2_1 light chain, VKD2A light chain, VK2D-29 light chain, VK2D-29(insL) light chain, VK7-3 light chain, VK4-1 light chain, VK4-1(insLY), VK-1(insL), VK2-30-2 light chain, VK2D-28 light chain, VK2D-28 (insL) light chain or VK2-24 light chain. In addition, the light chain framework regions may be altered by introducing the mutation N85D of TPP-3656/3657/3658/3639 (see Table 2, below and SEQ ID NOS: 19, 33, 47 and 5)). In particular, TPP-3656 altered by this N85D mutation is now candidate TPP-4885 (BAY1896502), discussed in the Examples.

The heavy chain and light chain variable regions of an antibody provided herein may be represented by SEQ ID NO: 1 and 5, respectively. The heavy chain and light chain variable regions of an antibody provided herein may be represented by SEQ ID NO: 15 and 19, respectively. The heavy chain and light chain variable regions of an antibody provided herein may be represented by SEQ ID NO: 29 and 33, respectively. The heavy chain and light chain variable regions of an antibody provided herein may be represented by SEQ ID NO: 43 and 47, respectively.

The heavy chain of an antibody provided herein may be a VH3-72 heavy chain, VH3-7 heavy chain or VH3-7(del RL) heavy chain. The light chain of an antibody provided herein may be a VK7-3 light chain.

The heavy and light chains of an antibody provided herein may be represented by SEQ ID NOS: 11 and 12, or SEQ ID NOS: 25 and 26, or SEQ ID NOS: 39 and 40, or SEQ ID NOS: 53 and 54, respectively.

An antibody may be a single-chain antibody or an antibody fragment, such as a Fab', Fab, F(ab')$_2$, a single domain antibody, Fv, or scFv.

In some embodiments, the epitope can comprises one or more residues selected from Y143, S145, S146, R147, E148, K149, E149-A, A149-B, S173, G186, R187, C191, E192, G216, E217, G218, C219, G220, L221, L222, H223, and N224 of human activated Protein C.

Also provided are antibodies which can compete with any of the antibodies described herein for binding to human activated Protein C. For example, such a competing antibody can bind to one or more epitopes described above.

Also provided is a cell or cell line comprising a nucleic acid encoding a humanized IgG2 antibody comprising (a) a heavy chain comprising heavy chain CDRs represented by (i) SEQ ID NOS: 2 or 16, (ii) SEQ ID NOS: 3, 17 or 31 and (iii) SEQ ID NOS: 4 or 46, and (b) a light chain comprising light chain CDRs represented by (i) SEQ ID NO: 6, (ii) SEQ ID NO: 7 and (iii) SEQ ID NOS: 8.

The nucleic acid may encode heavy chain framework selected from VH1C heavy chain, VH3-72 heavy chain, VH3-7 heavy chain, VH3-72 heavy chain, VH3-7(del RL) heavy chain and VH3-48 heavy chain. The nucleic acid may encode a light chain framework selected from a VK2_1 light chain, VKD2A light chain, VK2D-29 light chain, VK2D-29(insL) light chain, VK7-3 light chain, VK4-1 light chain, VK4-1(insLY), VK-1(insL), VK2-30-2 light chain, VK2D-28 light chain, VK2D-28(insL) light chain and VK2-24 light chain. In addition, the light chain framework coding regions may be altered by introducing the mutation resulting in a change of N85D of TPP-3656/3657/3658/3639 (see Table 2, below and SEQ ID NOS: 24, 38, 47 and 10). In particular, TPP-3656 altered by this N85D mutation (AAT→GAT or AAC→GAC) is now candidate TPP-4485, discussed in the Examples.

The nucleic acid may encode heavy chain and light chain variable regions represented by SEQ ID NO: 1 and 5, respectively. The nucleic acid may encode heavy chain and light chain variable regions represented by SEQ ID NO: 15 and 19, respectively. The nucleic acid may encode heavy chain and light chain variable regions represented by SEQ ID NO: 29 and 33, respectively. The nucleic acid may encode heavy chain and light chain variable regions represented by SEQ ID NO: 43 and 47, respectively.

The heavy chain encoded by the nucleic acid may be a VH3-72 heavy chain, VH3-7 heavy chain or VH3-7(del RL) heavy chain. The light chain encoded by the nucleic acid may be a VK7-3.

The heavy and light chains encoded by the nucleic acid may be represented by SEQ ID NOS: 11 and 12, or SEQ ID NOS: 25 and 26, or SEQ ID NOS: 39 and 40, or SEQ ID NOS: 53 and 54, respectively.

The nucleic acid may encode a single-chain antibody or an antibody fragment, such as a Fab', Fab, F(ab')$_2$, a single domain antibody, Fv, or scFv.

Also provided is a pharmaceutical composition comprising an antibody according to the description above dispersed in a pharmaceutically acceptable carrier.

Also provided is a method of inhibiting activated protein C anticoagulant activity in a subject, comprising administering an effective amount of an antibody according to the description above.

Also provided is a method of inhibiting activated protein C amidolytic activity in a subject comprising administering an effective amount of an antibody according to the description above.

Also provided is a method of treating a subject in need of blood coagulation comprising administering an effective amount of an antibody according to the description above.

Also provided is a method of treating a subject suffering from sepsis comprising administering an effective amount of an antibody according to the description above. The method may further comprise administration of activated protein C.

Also provided is a method of treating a subject suffering from hemophilia comprising administering an effective amount of an antibody according to the description above.

Also provided is a method of modulating hemostasis in a subject, comprising administering an effective amount of an antibody according to the description above. The subject may be a trauma patient.

Also provided is a method of modulating thrombosis in a subject, comprising administering an effective amount of an antibody according to the description above.

Yet another embodiment includes a kit comprising an antibody according to the description above. The antibody may be labeled, such as with a fluorophore, a radiolabel, a chemilluminescent label, a dye, a quantum dot, a bead or a chromophore. The kit may further comprise a buffer or diluent, and/or instructions on the use of said antibody. The antibody may be present in an aqueous suspension, or be lyophilized.

It is contemplated that any embodiment discussed in this specification can be implemented with respect to any compound, method, or composition, and vice versa.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4B is TPP-3657; FIG. 4C is TPP-3658. These data correspond to data summarized in Table 2.

Figure 1:
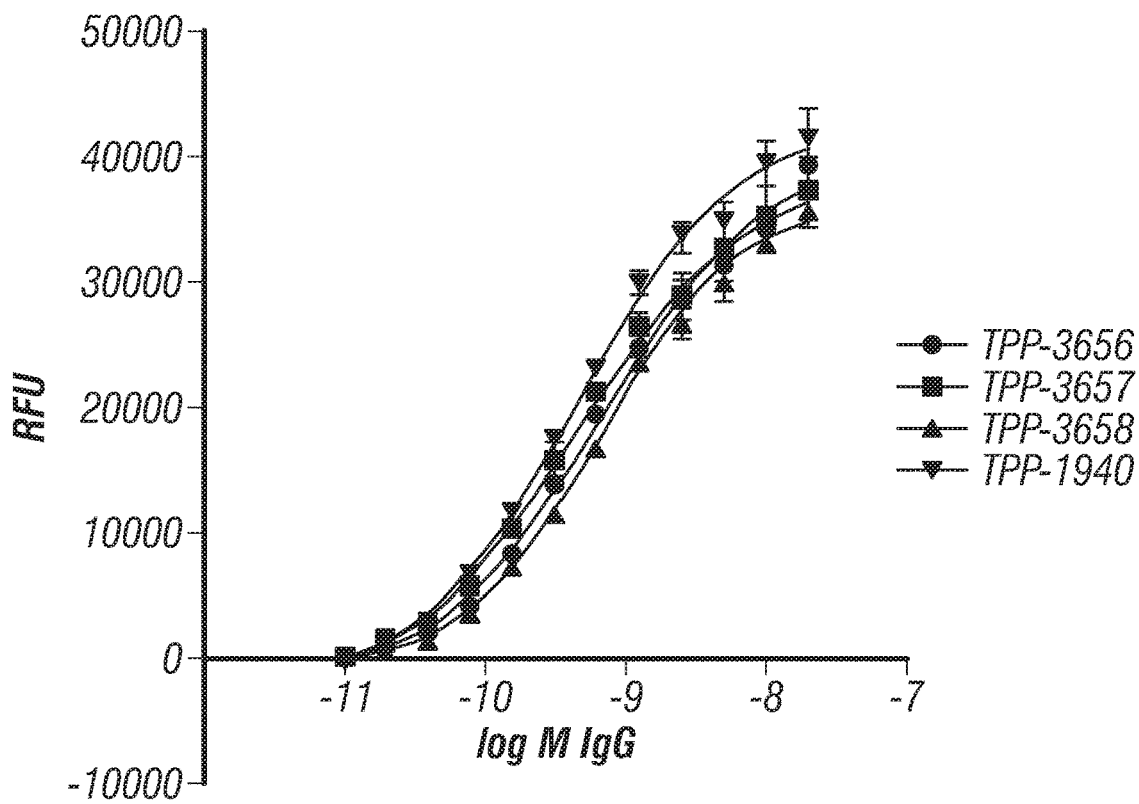
FIG. 1. aPC binding for the optimized germlined anti-aPC IgGs. Titration of anti-aPC IgGs in an aPC-ELISA. These data correspond to data summarized in Table 2.

Furthermore, it is contemplated that an antigen binding fragment can be encompassed in an antibody mimetic. The term "antibody mimetic" or "mimetic" as used herein is meant a protein that exhibits binding similar to an antibody but is a smaller alternative antibody or a non-antibody protein. Such antibody mimetic can be comprised in a scaffold. The term "scaffold" refers to a polypeptide platform for the engineering of new products with tailored functions and characteristics.

As used herein, the term "anti-aPC antibody" refers to an antibody that specifically binds to an epitope of aPC. When bound in vivo to an epitope of aPC, the anti-aPC antibodies disclosed herein augment one or more aspects of the blood clotting cascade.

As used herein, the terms "inhibits binding" and "blocks binding" (e.g., referring to inhibition/blocking of binding of aPC substrate to aPC) are used interchangeably and encompass both partial and complete inhibition or blocking of a protein with its substrate, such as an inhibition or blocking by at least about 10%, about 20%, about 30%, about 40%, about 50%, about 60%, about 70%, about 80%, about 90%, about 95%, about 96%, about 97%, about 98%, about 99%, or about 100%. As used herein, "about" means +/−10% of the numerical value indicated.

In reference to the inhibition and/or blocking of binding of aPC substrate to aPC, the terms inhibition and blocking also include any measurable decrease in the binding affinity of aPC to a physiological substrate when in contact with an anti-aPC antibody as compared to aPC not in contact with an anti-aPC antibody, e.g., the blocking of the interaction of aPC with its substrates, including Factor Va or with Factor VIIIa, by at least about 10%, about 20%, about 30%, about 40%, about 50%, about 60%, about 70%, about 80%, about 90%, about 95%, about 96%, about 97%, about 98%, about 99%, or about 100%.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity that have variable and constant regions derived from human germline immunoglobulin sequences. The human antibodies can include amino acid residues not encoded by human germline immunoglobulin sequences (e.g., mutations introduced by random or site-specific mutagenesis in vitro or by somatic mutation in vivo).

An "isolated antibody," as used herein, is intended to refer to an antibody which is substantially free of other biological molecules, including antibodies having different antigenic specificities (e.g., an isolated antibody that binds to aPC is substantially free of antibodies that bind antigens other than aPC). In some embodiments, the isolated antibody is at least about 75%, about 80%, about 90%, about 95%, about 97%, about 99%, about 99.9% or about 100% pure by dry weight. In some embodiments, purity can be measured by a method such as column chromatography, polyacrylamide gel electrophoresis, or HPLC analysis. An isolated antibody that binds to an epitope, isoform or variant of human aPC can, however, have cross-reactivity to other related antigens, e.g., from other species (e.g., aPC species homologs). Moreover, an isolated antibody can be substantially free of other cellular material and/or chemicals. As used herein, "specific binding" refers to antibody binding to a predetermined antigen. Typically, an antibody that exhibits "specific binding" binds to an antigen with an affinity of at least about $10^5 M^{-1}$ and binds to that antigen with an affinity that is higher, for example at least two-fold greater, than its binding affinity for an irrelevant antigen (e.g., BSA, casein). The phrases "an antibody recognizing an antigen" and "an antibody specific for an antigen" are used interchangeably herein with the term "an antibody which binds specifically to an antigen."

As used herein, the term "minimal binding" refers to an antibody that does not bind to and/or exhibits low affinity to a specified antigen. Typically, an antibody having minimal binding to an antigen binds to that antigen with an affinity that is lower than about $10^2 M^{-1}$ and does not bind to a predetermined antigen with higher affinity than it binds to an irrelevant antigen.

As used herein, the term "high affinity" for an antibody, such as an IgG antibody refers to a binding affinity of at least about $10^7 M^{-1}$, in at least one embodiment at least about $10^8 M^{-1}$, in some embodiments at least about $10^9 M^{-1}$, $10^{10} M^{-1}$, $10^{11} M^{-1}$ or greater, e.g., up to $10^{13} M^{-1}$ or greater. However, "high affinity" binding can vary for other antibody isotypes. For example, "high affinity" binding for an IgM isotype refers to a binding affinity of at least about $10^7 M^{-1}$. As used herein, "isotype" refers to the antibody class (e.g., 1 µM or IgG2) that is encoded by heavy chain constant region genes.

"Complementarity-determining region" or "CDR" refers to one of three hypervariable regions within the variable region of the heavy chain or the variable region of the light chain of an antibody molecule that form the N-terminal antigen-binding surface that is complementary to the three-dimensional structure of the bound antigen. Proceeding from the N-terminus of a heavy or light chain, these complementarity-determining regions are denoted as "CDR1," "CDR2," and "CDR3," respectively (Wu T T, Kabat E A, Bilofsky H, Proc Natl Acad Sci USA. 1975 December; 72(12):5107 and Wu T T, Kabat E A, J Exp Med. 1970 Aug. 1; 132(2):211). CDRs are involved in antigen-antibody binding, and the CDR3 comprises a unique region specific for antigen-antibody binding. An antigen-binding site, therefore, can include six CDRs, comprising the CDR regions from each of a heavy and a light chain V region.

The term "epitope" refers to the area or region of an antigen to which an antibody specifically binds or interacts, which in some embodiments indicates where the antigen is in physical contact with the antibody. Conversely, the term "paratope" refers to the area or region of the antibody on which the antigen specifically binds. Epitopes characterized by competition binding are said to be overlapping if the binding of the corresponding antibodies are mutually exclusive, i.e., binding of one antibody excludes simultaneous binding of another antibody. The epitopes are said to be separate (unique) if the antigen is able to accommodate binding of both corresponding antibodies simultaneously.

The term "competing antibodies," as used herein, refers to antibodies that bind to about, substantially or essentially the same, or even the same, epitope as an antibody against aPC as described herein. "Competing antibodies" include antibodies with overlapping epitope specificities. Competing antibodies are thus able to effectively compete with an antibody as described herein for binding to aPC. In some embodiments, the competing antibody can bind to the same epitope as the antibody described herein. Alternatively viewed, the competing antibody has the same epitope specificity as the antibody described herein.

As used herein, "conservative substitutions" refers to modifications of a polypeptide that involve the substitution of one or more amino acids for amino acids having similar biochemical properties that do not result in loss of a biological or biochemical function of the polypeptide. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine), and aromatic side chains (e.g., tyrosine, phenylalanine, tryptophan, histidine). Antibodies of the present disclosure can have one or more conservative amino acid substitutions yet retain antigen binding activity.

For nucleic acids and polypeptides, the term "substantial homology" indicates that two nucleic acids or two polypeptides, or designated sequences thereof, when optimally aligned and compared, are identical, with appropriate nucleotide or amino acid insertions or deletions, in at least about 80% of the nucleotides or amino acids, usually at least about 85%, in some embodiments about 90%, 91%, 92%, 93%, 94%, or 95%, in at least one embodiment at least about 96%, 97%, 98%, 99%, 99.1%, 99.2%, 99.3%, 99.4%, or 99.5% of the nucleotides or amino acids. Alternatively, substantial homology for nucleic acids exists when the segments will hybridize under selective hybridization conditions to the complement of the strand. Also included are nucleic acid sequences and polypeptide sequences having substantial homology to the specific nucleic acid sequences and amino acid sequences recited herein.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, such as without limitation the AlignX™ module of VectorNTI™ (Invitrogen Corp., Carlsbad, Calif.). For AlignX™, the default parameters of multiple alignment are: gap opening penalty: 10; gap extension penalty: 0.05; gap separation penalty range: 8; % identity for alignment delay: 40 (further details found at the world-wide-web at invitrogen.com/site/us/en/home/LINNEA-Online-Guides/LINNEA-Communities/Vector-NTI-Community/Sequence-analysis-and-data-management-software-for-PCs/AlignX-Module-for-Vector-NTI-Advance.reg.us.html).

Another method for determining the best overall match between a query sequence (a sequence of the present disclosure) and a subject sequence, also referred to as a global sequence alignment, can be determined using the CLUSTALW computer program (Thompson et al., *Nucleic Acids Res*, 1994, 2(22): 4673-4680), which is based on the algorithm of Higgins et al., *Computer Applications in the Biosciences* (CABIOS), 1992, 8(2): 189-191). In a sequence alignment the query and subject sequences are both DNA sequences. The result of said global sequence alignment is in percent identity. Parameters that can be used in a CLUSTALW alignment of DNA sequences to calculate percent identity via pairwise alignments are: Matrix=IUB, k-tuple=1, Number of Top Diagonals=5, Gap Penalty=3, Gap Open Penalty=10, Gap Extension Penalty=0.1. For multiple alignments, the following CLUSTALW parameters can be used: Gap Opening Penalty=10, Gap Extension Parameter=0.05; Gap Separation Penalty Range=8; % Identity for Alignment Delay=40.

The nucleic acids can be present in whole cells, in a cell lysate, or in a partially purified or substantially pure form. A nucleic acid is "isolated" or "rendered substantially pure" when purified away from other cellular components with which it is normally associated in the natural environment. To isolate a nucleic acid, standard techniques such as the following can be used: alkaline/SDS treatment, CsCl banding, column chromatography, agarose gel electrophoresis and others well known in the art.

I. ACTIVATED PROTEIN C (APC) AND ANTIBODIES

A. Activated Protein C

Protein C is activated by thrombin complexed with thrombomodulin on endothelium. Unlike the few-second transient life of active thrombin in vivo, human aPC has about a 20 minute half-life in circulation after its generation (Berg et al., 2003). Therefore, one can feasibly measure a level of aPC in plasma to study its regulation under various pathophysical conditions.

B. Antibodies to aPC

Previously, a murine antibody HAPC1573 was developed which enhanced FL-aPC binding on the endothelial cells. HAPC1573 facilitated aPC internalization on endothelium through the interaction of Gla domain of aPC and EPCR on the cells, and this internalization could be blocked by either EPCR blocking Ab or Gla domain blocking Ab (HPC1575). HAPC1573 also dramatically altered the kinetic parameters of aPC toward its chromogenic substrate, Spectrozyme PCa. This profound change of aPC toward small peptide substrate in the presence of HAPC1573 indicated that this mAb recognized an epitope near active site of aPC and the interaction of Ab and antigen dramatically increased the affinity of APC toward small peptide substrate but decreased the off rate of product from aPC catalytic site. HAPC1573 also almost completely diminished the prolongation effect of aPC in factor Xa initiated one-stage plasma clotting assay, suggesting that the interaction of HAPC1573 and aPC prevents aPC from cleaving factor Va. Surprisingly, HAPC1573 did not inhibit but actually enhanced aPC cleaving histone H3 and H4. Consistently, HAPC1573 did not inhibit but slightly enhanced aPC cytoprotection activity on endothelium against histone H3 and H4. Finally, their results show that HAPC1573, recognizes aPC, but not Protein C. See U.S. Pat. No. 8,153,766.

Recent studies have shown that anticoagulant activity of aPC is dispensable for its cytoprotective function, but aPC cleavage activity toward PAR1 might be essential for its anti-apoptotic effect (Mosnier et al., 2004). However, the cytoprotection effect of aPC has been shown not only in endothelial cells which express EPCR, but also on other cells such as neuron and keratinocytes which do not express EPCR on their cell surfaces (Guo et al., 2004; Berg et al., 2003), indicating other mechanisms than PAR1 mediated aPC signaling might exist.

C. Applications of the Technology

The ability to distinguish between Protein C and aPC demonstrates the utility of antibodies in a convenient ELISA method for measuring aPC level in plasma in vivo. Typically, it takes less than 4 hours to measure a plasma sample containing 1 ng/ml APC with this method compared to 19 hours or even weeks with enzyme capture assays (Gruber and Griffen, 1992; Liaw et al., 2003).

Also, as discussed above, HAPC1573 altered aPC cleavage activity toward a chromogenic peptide substrate and also blocked aPC anticoagulant activity in a plasma clotting assay, suggesting this mAb recognizes an epitope near the aPC active site and alters its catalytic activity upon antibody-antigen binding. At the same time, HAPC1573 actually enhanced aPC cleaving extracellular histones, and enhanced APC cytoprotection activity on endothelium against histones. This indicates that APC anticoagulant activity for cleaving activated factor V and VIII is not required for its cytoprotection activity by cleaving extracellular histones. Cleaving extracellular histones independent from its anticoagulant activity might be one of the molecular mechanisms of aPC regulation inflammation and cytoprotection.

Thus, such antibodies against aPC can, for example, be used in treatment of hemophilia A patients. aPC cleaves both factor VIIIa and factor Va and thus negatively affects blood clotting. In hemophilia A patients, factor VIII levels are low and the inactivation of factor Va by aPC is probably a major pathway to regulate hemostasis and thrombosis in these patients. Recent clinical reports demonstrated factor V Leiden mutant which is resistant to aPC cleavage was beneficial to hemophilia A patients regarding their bleeding symptom (van't Zant et al., 1997). Blocking aPC anticoagulant activity toward factor Va in vivo with an antibody is an alternative approach for hemophilia A treatments, especially for those patients who have high level factor VIII inhibitors so that the factor VIII replacement therapy would not be very effective.

In other embodiments, another possible clinical application for antibodies against aPC is in the treatment of trauma patients wherein homeostasis is disrupted, excessive bleeding is likely, and surgical intervention is delayed to regain homeostatis. Treatment with antibodies can selectively restore the pro-coagulant state without eliminating the cytoprotective or anti-inflammatory activities of APC.

Yet another clinical application of antibodies against aPC is in combination with aPC in sepsis treatment. Its bleeding side effect in patients is due to aPC anticoagulant activity. Because HAPC1573 blocked aPC anticoagulant activity while maintaining, and even enhancing, aPC cytoprotective effect, the mAb-aPC complex can be a better therapeutic than aPC alone regarding its bleeding side effect.

II. ANTIBODY STRUCTURE AND OPTIMIZATION

Antibodies comprise a large family of glycoproteins with common structural features. An antibody is comprised of four polypeptides that form a three dimensional structure. Typically, an antibody is comprised of two different polypeptides, the heavy chain and the light chain. An antibody molecule is comprised of one or more of these units, each unit comprising two heavy chains and two light chains. An antibody molecule typically consists of three functional domains: the Fc, Fab, and antigen-binding site.

There are five different types of heavy chain polypeptides designated as α, δ, ε, γ, and μ. There are two different types of light chain polypeptides designated κ and λ. An antibody typically contains only one type of heavy chain and only one type of light chain, although any light chain can associate with any heavy chain.

The carboxyl terminal of each heavy chain polypeptide is known as the constant (Fc) region. The amino terminal of each heavy and light chain polypeptide is known as the variable (V) region. Within the variable regions of the chains are hypervariable regions known as complementarity determining regions (CDRs). The variable regions of one heavy chain and one light chain associate to form an antigen-binding site. Each heavy chain and each light chain includes three CDRs. The six CDRs of an antigen-binding site define the amino acid residues that form the actual binding site for the antigen. CDR variability accounts for the diversity of antigen recognition.

Antibodies against aPC may be defined by sequences set forth in the following table:

| Antibody | Sequence Name | Sequence Region | Sequence Type | SEQ ID |
|---|---|---|---|---|
| TPP-3639 | HU1573-V4-hIgG2Kappa | VH | PRT | SEQ ID NO: 1 |
| TPP-3639 | HU1573-V4-hIgG2Kappa | HCDR1 | PRT | SEQ ID NO: 2 |
| TPP-3639 | HU1573-V4-hIgG2Kappa | HCDR2 | PRT | SEQ ID NO: 3 |
| TPP-3639 | HU1573-V4-hIgG2Kappa | HCDR3 | PRT | SEQ ID NO: 4 |
| TPP-3639 | HU1573-V4-hIgG2Kappa | VL | PRT | SEQ ID NO: 5 |
| TPP-3639 | HU1573-V4-hIgG2Kappa | LCDR1 | PRT | SEQ ID NO: 6 |
| TPP-3639 | HU1573-V4-hIgG2Kappa | LCDR2 | PRT | SEQ ID NO: 7 |
| TPP-3639 | HU1573-V4-hIgG2Kappa | LCDR3 | PRT | SEQ ID NO: 8 |
| TPP-3639 | HU1573-V4-hIgG2Kappa | VH | DNA | SEQ ID NO: 9 |
| TPP-3639 | HU1573-V4-hIgG2Kappa | VL | DNA | SEQ ID NO: 10 |
| TPP-3639 | HU1573-V4-hIgG2Kappa | Heavy Chain | PRT | SEQ ID NO: 11 |
| TPP-3639 | HU1573-V4-hIgG2Kappa | Light Chain | PRT | SEQ ID NO: 12 |
| TPP-3639 | HU1573-V4-hIgG2Kappa | Heavy Chain | DNA | SEQ ID NO: 13 |
| TPP-3639 | HU1573-V4-hIgG2Kappa | Light Chain | DNA | SEQ ID NO: 14 |
| TPP-3656 | HU1573-V3-hIgG2Kappa | VH | PRT | SEQ ID NO: 15 |
| TPP-3656 | HU1573-V3-hIgG2Kappa | HCDR1 | PRT | SEQ ID NO: 16 |
| TPP-3656 | HU1573-V3-hIgG2Kappa | HCDR2 | PRT | SEQ ID NO: 17 |
| TPP-3656 | HU1573-V3-hIgG2Kappa | HCDR3 | PRT | SEQ ID NO: 18 |
| TPP-3656 | HU1573-V3-hIgG2Kappa | VL | PRT | SEQ ID NO: 19 |
| TPP-3656 | HU1573-V3-hIgG2Kappa | LCDR1 | PRT | SEQ ID NO: 20 |
| TPP-3656 | HU1573-V3-hIgG2Kappa | LCDR2 | PRT | SEQ ID NO: 21 |
| TPP-3656 | HU1573-V3-hIgG2Kappa | LCDR3 | PRT | SEQ ID NO: 22 |
| TPP-3656 | HU1573-V3-hIgG2Kappa | VH | DNA | SEQ ID NO: 23 |
| TPP-3656 | HU1573-V3-hIgG2Kappa | VL | DNA | SEQ ID NO: 24 |
| TPP-3656 | HU1573-V3-hIgG2Kappa | Heavy Chain | PRT | SEQ ID NO: 25 |
| TPP-3656 | HU1573-V3-hIgG2Kappa | Light Chain | PRT | SEQ ID NO: 26 |
| TPP-3656 | HU1573-V3-hIgG2Kappa | Heavy Chain | DNA | SEQ ID NO: 27 |
| TPP-3656 | HU1573-V3-hIgG2Kappa | Light Chain | DNA | SEQ ID NO: 28 |
| TPP-3657 | HU1573-V2-hIgG2Kappa | VH | PRT | SEQ ID NO: 29 |

| Antibody | Sequence Name | Sequence Region | Sequence Type | SEQ ID |
|---|---|---|---|---|
| TPP-3657 | HU1573-V2-hIgG2Kappa | HCDR1 | PRT | SEQ ID NO: 30 |
| TPP-3657 | HU1573-V2-hIgG2Kappa | HCDR2 | PRT | SEQ ID NO: 31 |
| TPP-3657 | HU1573-V2-hIgG2Kappa | HCDR3 | PRT | SEQ ID NO: 32 |
| TPP-3657 | HU1573-V2-hIgG2Kappa | VL | PRT | SEQ ID NO: 33 |
| TPP-3657 | HU1573-V2-hIgG2Kappa | LCDR1 | PRT | SEQ ID NO: 34 |
| TPP-3657 | HU1573-V2-hIgG2Kappa | LCDR2 | PRT | SEQ ID NO: 35 |
| TPP-3657 | HU1573-V2-hIgG2Kappa | LCDR3 | PRT | SEQ ID NO: 36 |
| TPP-3657 | HU1573-V2-hIgG2Kappa | VH | DNA | SEQ ID NO: 37 |
| TPP-3657 | HU1573-V2-hIgG2Kappa | VL | DNA | SEQ ID NO: 38 |
| TPP-3657 | HU1573-V2-hIgG2Kappa | Heavy Chain | PRT | SEQ ID NO: 39 |
| TPP-3657 | HU1573-V2-hIgG2Kappa | Light Chain | PRT | SEQ ID NO: 40 |
| TPP-3657 | HU1573-V2-hIgG2Kappa | Heavy Chain | DNA | SEQ ID NO: 41 |
| TPP-3657 | HU1573-V2-hIgG2Kappa | Light Chain | DNA | SEQ ID NO: 42 |
| TPP-3658 | HU1573-V1-hIgG2Kappa | VH | PRT | SEQ ID NO: 43 |
| TPP-3658 | HU1573-V1-hIgG2Kappa | HCDR1 | PRT | SEQ ID NO: 44 |
| TPP-3658 | HU1573-V1-hIgG2Kappa | HCDR2 | PRT | SEQ ID NO: 45 |
| TPP-3658 | HU1573-V1-hIgG2Kappa | HCDR3 | PRT | SEQ ID NO: 46 |
| TPP-3658 | HU1573-V1-hIgG2Kappa | VL | PRT | SEQ ID NO: 47 |
| TPP-3658 | HU1573-V1-hIgG2Kappa | LCDR1 | PRT | SEQ ID NO: 48 |
| TPP-3658 | HU1573-V1-hIgG2Kappa | LCDR2 | PRT | SEQ ID NO: 49 |
| TPP-3638 | HU1573-V1-hIgG2Kappa | LCDR3 | PRT | SEQ ID NO: 50 |
| TPP-3658 | HU1573-V1-hIgG2Kappa | VH | DNA | SEQ ID NO: 51 |
| TPP-3658 | HU1573-V1-hIgG2Kappa | VL | DNA | SEQ ID NO: 52 |
| TPP-3658 | HU1573-V1-hIgG2Kappa | Heavy Chain | PRT | SEQ ID NO: 53 |
| TPP-3658 | HU1573-V1-hIgG2Kappa | Light Chain | PRT | SEQ ID NO: 54 |
| TPP-3658 | HU1573-V1-hIgG2Kappa | Heavy Chain | DNA | SEQ ID NO: 55 |
| TPP-3658 | HU1573-V1-hIgG2Kappa | Light Chain | DNA | SEQ ID NO: 56 |
| TPP-3356 | H1573VK2-VH1Cgl1-hIgG2Kappa | VH | PRT | SEQ ID NO: 57 |
| TPP-3356 | H1573VK2-VH1Cgl1-hIgG2Kappa | HCDR1 | PRT | SEQ ID NO: 58 |
| TPP-3356 | H1573VK2-VH1Cgl1-hIgG2Kappa | HCDR2 | PRT | SEQ ID NO: 59 |
| TPP-3356 | H1573VK2-VH1Cgl1-hIgG2Kappa | HCDR3 | PRT | SEQ ID NO: 60 |
| TPP-3356 | H1573VK2-VH1Cgl1-hIgG2Kappa | VL | PRT | SEQ ID NO: 61 |
| TPP-3356 | H1573VK2-VH1Cgl1-hIgG2Kappa | LCDR1 | PRT | SEQ ID NO: 62 |
| TPP-3356 | H1573VK2-VH1Cgl1-hIgG2Kappa | LCDR2 | PRT | SEQ ID NO: 63 |
| TPP-3356 | H1573VK2-VH1Cgl1-hIgG2Kappa | LCDR3 | PRT | SEQ ID NO: 64 |
| TPP-3356 | H1573VK2-VH1Cgl1-hIgG2Kappa | VH | DNA | SEQ ID NO: 65 |
| TPP-3356 | H1573VK2-VH1Cgl1-hIgG2Kappa | VL | DNA | SEQ ID NO: 66 |
| TPP-3356 | H1573VK2-VH1Cgl1-hIgG2Kappa | Heavy Chain | PRT | SEQ ID NO: 67 |
| TPP-3356 | H1573VK2-VH1Cgl1-hIgG2Kappa | Light Chain | PRT | SEQ ID NO: 68 |
| TPP-3356 | H1573VK2-VH1Cgl1-hIgG2Kappa | Heavy Chain | DNA | SEQ ID NO: 69 |
| TPP-3356 | H1573VK2-VH1Cgl1-hIgG2Kappa | Light Chain | DNA | SEQ ID NO: 70 |
| TPP-3357 | H1573Vk2A-VH1Cgl2-hIgG2Kappa | VH | PRT | SEQ ID NO: 71 |
| TPP-3357 | H1573Vk2A-VH1Cgl2-hIgG2Kappa | HCDR1 | PRT | SEQ ID NO: 72 |
| TPP-3357 | H1573Vk2A-VH1Cgl2-hIgG2Kappa | HCDR2 | PRT | SEQ ID NO: 73 |
| TPP-3357 | H1573Vk2A-VH1Cgl2-hIgG2Kappa | HCDR3 | PRT | SEQ ID NO: 74 |
| TPP-3357 | H1573Vk2A-VH1Cgl2-hIgG2Kappa | VH | DNA | SEQ ID NO: 75 |
| TPP-3357 | H1573Vk2A-VH1Cgl2-hIgG2Kappa | VL | DNA | SEQ ID NO: 76 |
| TPP-3357 | H1573Vk2A-VH1Cgl2-hIgG2Kappa | Heavy Chain | PRT | SEQ ID NO: 77 |
| TPP-3357 | H1573Vk2A-VH1Cgl2-hIgG2Kappa | Light Chain | PRT | SEQ ID NO: 78 |
| TPP-3357 | H1573Vk2A-VH1Cgl2-hIgG2Kappa | Heavy Chain | DNA | SEQ ID NO: 79 |
| TPP-3357 | H1573Vk2A-VH1Cgl2-hIgG2Kappa | Light Chain | DNA | SEQ ID NO: 80 |
| TPP-3357 | H1573VK2-VH1Cgl1-hIgG2Kappa | VL | PRT | SEQ ID NO: 81 |
| TPP-3357 | H1573VK2-VH1Cgl1-hIgG2Kappa | LCDR1 | PRT | SEQ ID NO: 82 |
| TPP-3357 | H1573VK2-VH1Cgl1-hIgG2Kappa | LCDR2 | PRT | SEQ ID NO: 83 |
| TPP-3357 | H1573VK2-VH1Cgl1-hIgG2Kappa | LCDR3 | PRT | SEQ ID NO: 84 |

A. Germlining

"Germlining" is the process of mutating the framework region amino acids to correspond to the closest human germline sequence. Germlining involves engineering changes in the amino acid sequence of a VH or VL domain to bring it closer to the sequence of a human VH or VL domain, such as the most similar human germline framework. Determination of homology between any VH or VL domain and human VH or VL domains is a critical step both for selection of amino acid residues to be changed and for selecting the appropriate replacement amino acid residues.

The skilled person can select a germline segment that is closest in sequence to the framework sequence of the antibody before germlining and test the affinity or activity of the antibodies to confirm that germlining does not significantly reduce antigen binding or potency in assays described herein. Human germline gene segment sequences are known to those skilled in the art and can be accessed for example from the VBASE compilation (VBASE, MRC Centre of Protein Engineering, UK, 1997).

The advantage of this approach is that the sequences encoded by the human germline genes (i.e., an immunoglobulin sequence encoded by non-lymphoid cells that have not undergone the maturation process that lead to genetic rearrangement) form part of the human immunological self, and are therefore well tolerated during human therapeutic use. The antibodies undergo affinity maturation owing to mutations made to the germline genes, but these mutations can be immunogenic.

WO2004/006955 describes methods for humanizing antibodies, based on selecting variable region framework sequences from human antibody genes by comparing canonical CDR structure types for CDR sequences of the variable region of a non-human antibody to canonical CDR structure types for corresponding CDRs from a library of human antibody sequences, e.g. germline antibody gene segments. Human antibody variable regions having similar canonical CDR structure types to the non-human CDRs form a subset of member human antibody sequences from which to select human framework sequences. The subset members may be further ranked by amino acid similarity between the human and the non-human CDR sequences. In the method of WO2004/006955, top ranking human sequences are selected to provide the framework sequences for constructing a chimeric antibody that functionally replaces human CDR sequences with the non-human CDR counterparts using the selected subset member human frameworks, thereby providing a humanized antibody of high affinity and low immunogenicity without need for comparing framework sequences between the non-human and human antibodies.

The hypervariable regions (CDRs), for their part, are very exposed on the surface of the Abs, so as to interact directly with the antigens. They are therefore very likely to cause a humoral immunologic response, even more than the framework regions. However, the interaction of the Ab with the antigen is closely dependent on the sequences of the hypervariable regions, and any mutation in these regions is highly likely to alter the affinity of the Ab for its antigen. However, the immunogenicity of the antibodies may be decreased by mutating the somatic genes coding for the hypervariable regions of recombinant antibodies to make them closer to human germline genes coding for these regions. In fact, when the hypervariable regions of Abs are mutated to make them as close as possible to the sequences encoded by the human germline genes, the problem of immunogenicity is avoided or limited since the sequences thus mutated are closer to the human "immunological self" and, surprisingly, such mutations are widely possible while preserving affinity of the Ab for its antigen comparable to the affinity of the initial Ab. Methods for germlining CDR sequences are provided in U.S. Patent Publication 2013/018440.

B. Framework Shuffling

Amino acids in the frameworks and CDRs can be substituted to other appropriate amino acids using library techniques such as framework shuffling (Damschroder et al, Mol. Immunol. 2007 April; 44(11): 3049-60) and CDR repair (US 2006/0122377). Antibodies may be reengineered or reshaped to reduce their immunogenicity, while maintaining the immunospecificity of the antibodies for an antigen. For example, antibodies immunospecific for an antigen may be generated by synthesizing a combinatorial library comprising complementarity determining regions (CDRs) from a donor antibody fused in frame to framework regions from a bank of framework regions.

III. ANTIBODIES AGAINST APC

A. Antibody Fragments

Thus, in one embodiment, such molecules may comprise fragments (such as (F(ab'), F(ab')2) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules can contain substituents capable of binding to different epitopes of the same molecule, or they can be capable of binding to an activated protein C epitope and a "non-activated protein C" epitope.

A single-chain variable fragment (scFv) is another form of antibody fragment. It comprises a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alaine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5 \times 10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the VH C terminus and an abundance of arginines and prolines at other positions as the only common features of the selected tethers.

The recombinant antibodies against aPC can also involve sequences or moieties that permit dimerization or multimerization of the receptors. Such sequences include those derived from IgA, which permit formation of multimers in conjunction with the J chain. Another multimerization domain is the Gal4 dimerization domain. In other embodiments, the chains can be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stablizing and coagulating agent. However, it is contemplated that dimers or multimers of the same analog or heteromeric complexes comprised of different analogs can be created. To link two different compounds in a step-wise manner, heterobifunctional cross-linkers can be used that eliminate unwanted homopolymer formation. An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker can react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

A cross-linker having reasonable stability in blood can be employed. Numerous types of disulfide-bond containing linkers are known that can be successfully employed to conjugate targeting and therapeutic/preventative agents. Linkers that contain a disulfide bond that is sterically hindered can prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site. The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxysuccinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers. U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like.

U.S. Pat. Nos. 5,141,648 and 5,563,250 disclose cleavable conjugates containing a labile bond that is cleavable under a variety of mild conditions. This linker is particularly useful in that the agent of interest can be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at 5 least one occurrence of a charged amino acid (e.g., arginine or lysine) followed by a proline, and is characterized by greater stability and reduced aggregation. U.S. Pat. No. 5,880,270 discloses aminooxy-containing linkers useful in a variety of immunodiagnostic and separative techniques.

B. Antibody Conjugates

Further provided are antibody conjugates. For both diagnostic and therapeutic purposes, one can link or covalently bind or complex an agent to an antibody. Such a molecule or moiety can be, but is not limited to, at least one effector or reporter molecule. A reporter molecule is defined as any moiety which can be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired. Another such example is the formation of a conjugate comprising an antibody linked to a cytotoxic or anti cellular agent, and can be termed "immunotoxins."

Antibody conjugates are used as diagnostic agents. Antibody diagnostics generally fall within two classes, those for use in in vitro diagnostics, such as in a variety of immunoassays, and/or those for use in vivo diagnostic protocols, generally known as "antibody-directed imaging."

Many appropriate imaging agents are known in the art, as are methods for their attachment to antibodies (see, e.g., U.S. Pat. Nos. 5,021,236; 4,938,948; and 4,472,509). The imaging moieties used can be paramagnetic ions; radioactive isotopes; fluorochromes, NMR-detectable substances; X-ray imaging.

In the case of paramagnetic ions, one might mention by way of example ions such as chromium (III), manganese (II), iron (III), iron (II), cobalt (II), nickel (II), copper (II), neodymium (Ill), samarium (III), ytterbium (III), gadolinium (III), vanadium (II), terbium (III), dysprosium (III), holmium (III) and/or erbium (III). Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine[211], [14]carbon, [51]chromium, [36]chlorine, [57]cobalt, [58]cobalt, copper[67], [152]Eu, gallium[67], [3]hydrogen, iodine[123], iodine[125], iodine[131], indium[111], [59]iron, [32]phosphorus, rhenium[186], rhenium[188], [75]selenium, [35]sulphur, technicium[99m] and/or yttrium[90]. [125]I is often being commonly used in certain embodiments, and technicium[99]m and/or indium[111] are also often used due to their low energy and suitability for long range detection. Radioactively labeled monoclonal antibodies can be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies can be labeled with technetium$^{99m}$ by ligand exchange process, for example, by reducing pertechnate with stannous solution, chelating the reduced technetium onto a Sephadex column and applying the antibody to this column. Alternatively, direct labeling techniques can be used, e.g., by incubating pertechnate, a reducing agent such as $SNCl_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650. BODIPY 650/665, BODIPY-FL. BODIPY-R6G, BODIPY-TMR, BODIPY-TRX, Cascade Blue, Cy3, Cy5,6-FAM, Fluorescein Isothiocyanate. HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this cannot be advantageous since it results in loss of antigen binding by the antibody conjugate.

Molecules containing azido groups can also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and can be used as antibody binding agents.

Several methods are known in the art for the attachment or conjugation of an antibody to its conjugate moiety. Some attachment methods involve the use of a metal chelate complex employing, for example, an organic chelating agent such as described in U.S. Pat. Nos. 4,472,509 and 4,938,948). Monoclonal antibodies can also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

In another embodiment, one may choose to modify the immunoglobulins to improve their stability and half-life in vivo. PEGylation is one such process that involves covalent attachment of polyethylene glycol (PEG) polymer chains to the antibody. PEGylation is routinely achieved by incubation of a reactive derivative of PEG with the target molecule. The covalent attachment of PEG can "mask" the antibody from the host's immune system (reduced immunogenicity and antigenicity), and increase the hydrodynamic size (size in solution) of the agent which prolongs its circulatory time by reducing renal clearance. PEGylation can also provide water solubility. Other polymers used to modify antibodies include polyethyleneimine and polylysine, often linked through succinic acid groups.

C. Immunodetection Methods

In still further embodiments, also provided are immunodetection methods for binding, purifying, removing, quantifying and/or otherwise generally detecting biological components using antibodies that react immunologically with such components. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle and Ben-Zeev (1999); Gulbis and Galand (1993); De Jager et al. (1993); and Nakamura et al. (1987).

In general, the immunobinding methods include obtaining a sample containing a target of interest, and contacting the sample with a first antibody that reacts immunologically with the target under conditions effective to allow the formation of immunocomplexes. The binding of the antibody to the target can then be assessed using a variety of different formats.

In one format, the antibody can be linked to a solid support, such as in the form of a column matrix, and the sample suspected of containing the target will be applied to the immobilized antibody. The unwanted components will be washed from the column, leaving the target immunocomplexed to the immobilized antibody to be eluted.

The immunobinding methods also include methods for detecting and quantifying the amount of a target in a sample and the detection and quantification of any immune complexes formed during the binding process. Here, one would obtain a sample suspected of containing a target, and contact the sample with an antibody against the target, and then detect and quantify the amount of immune complexes formed under the specific conditions.

In terms of antigen detection, the biological sample analyzed can be any sample that is suspected of containing a target, such as, for example, a body fluid like blood, serum, plasma, mucous, urine, saliva, tears or semen. Alternatively, a tissue can be used. Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to targets that react immunologically with antibodies present. After this time, the sample-antibody composition, such as a tissue section, ELISA plate, dot blot or western blot, will generally be washed to remove any non-specifically bound species, allowing only those molecules specifically bound within the primary immune complexes to be detected.

In general, the detection of immunocomplex formation is well known in the art and can be achieved through the application of numerous approaches. These methods are generally based upon the detection of a label or marker, such as any of those radioactive, fluorescent, biological and enzymatic tags. U.S. Patents concerning the use of such labels include U.S. Pat. Nos. 3,817,837; 3,850,752; 3,939,350; 3,996,345; 4,277,437; 4,275,149 and 4,366,241. Of course, one can find additional advantages through the use of a secondary binding ligand such as a second antibody and/or a biotin/avidin ligand binding arrangement, as is known in the art.

The antibody employed in the detection can itself be linked to a detectable label, wherein one would then simply detect this label, thereby allowing the amount of the primary immune complexes in the composition to be determined. Alternatively, the first antibody that becomes bound within the primary immune complexes can be detected by means of a second binding ligand that has binding affinity for the antibody. In these cases, the second binding ligand can be linked to a detectable label. The second binding ligand is itself often an antibody, which can thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system can provide for signal amplification if this is desired.

One method of immunodetection designed by Charles Cantor uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

Another ELISA in which the antigens are immobilized, involves the use of antibody competition in the detection. In this ELISA, labeled antibodies against an antigen are added to the wells, allowed to bind, and/or detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

As detailed above, immunoassays, in their most simple and/or direct sense, are binding assays. Certain immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like can also be used. Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a non-specific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions can include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures on the order of 25° C. to 27° C., or can be overnight at about 4° C. or so.

D. Purification

In certain embodiments, the antibodies against aPC can be purified. The term "purified," as used herein, is intended to refer to a composition, isolatable from other components, wherein the protein is purified to any degree relative to its naturally-obtainable state. A purified protein therefore also refers to a protein, free from the environment in which it can naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest can be further purified using chromatographic and electrophoretic techniques to achieve partial or complete purification (or purification to homogeneity).

Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody against aPC, it can be desirable to express the polypeptide in a prokaryotic or eukaryotic expression system and extract the protein using denaturing conditions. The polypeptide can be purified from other cellular components using an affinity column, which binds to a tagged portion of the polypeptide. As is generally known in the art, it is believed that the order of conducting the various purification steps can be changed, or that certain steps can be omitted, and still result in a suitable method for the preparation of a substantially purified protein or peptide.

Commonly, complete antibodies are fractionated utilizing agents (i.e., protein A) that bind the Fc portion of the antibody. Alternatively, antigens can be used to simultaneously purify and select appropriate antibodies. Such methods often utilize the selection agent bound to a support, such as a column, filter or bead. The antibodies is bound to a support, contaminants removed, and the antibodies released by applying conditions (salt, heat, and the like).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE. It will therefore be appreciated that under differing electrophoresis conditions, the apparent molecular weights of purified or partially purified expression products can vary.

IV. PHARMACEUTICAL COMPOSITIONS AND USES

A. Compositions

Pharmaceutical compositions can comprise an effective amount of one or more antibodies, therapeutic agents or additional agent dissolved or dispersed in a pharmaceutically acceptable carrier. Aqueous compositions comprise an effective amount of the antibody, dissolved or dispersed in a pharmaceutically acceptable carrier or aqueous medium. The phrases "pharmaceutically or pharmacologically acceptable" refer to molecular entities and compositions that do not produce an adverse, allergic or other untoward reaction when administered to an animal, or a human, as appropriate.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329). The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. For human administration, preparations should meet sterility, pyrogenicity, general safety and purity standards as required by FDA Office of Biologic Standards.

The biological material should be extensively dialyzed to remove undesired small molecular weight molecules and/or lyophilized for more ready formulation into a desired vehicle, where appropriate. The active compounds will then generally be formulated for parenteral administration, e.g., formulated for injection via the intravenous, intramuscular, sub-cutaneous, intranasal, or intraperitoneal routes. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions, formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The antibodies against aPC can be formulated into a composition in a free base, in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, isotonic agents can be included, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the methods of preparation are vacuum-drying and freeze-drying techniques which yield a powder of the active ingredient plus any additional desired ingredient from a previously sterile-filtered solution thereof. The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intranasal, and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

In addition to the compounds formulated for parenteral administration, such as intravenous or intramuscular injection, other pharmaceutically acceptable forms include, e.g., tablets or other solids for oral administration; liposomal formulations; time release capsules; and any other form currently used, including creams.

In certain embodiments, the use of liposomes and/or nanoparticles is contemplated for the formulation and administration of the antibodies and/or analogs thereof. The formation and use of liposomes is generally known to those of skill in the art, and is also described below.

Nanocapsules can generally entrap compounds in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use, and such particles are easily made.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200-500 Å, containing an aqueous solution in the core.

The following information can also be utilized in generating liposomal formulations. Phospholipids can form a variety of structures other than liposomes when dispersed in water, depending on the molar ratio of lipid to water. At low ratios the liposome is the recommended structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one can operate at the same time.

The therapeutic agent can comprise different types of carriers depending on whether it is to be administered in solid, liquid or aerosol form, and whether it needs to be sterile for such routes of administration as injection. The antibodies against aPC can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intramuscularly, intraperitoneally, subcutaneously, subconjunctival, intravesicularlly, mucosally, intrapericardially, intraumbilically, intraocularally, orally, topically, locally, by inhalation (e.g., aerosol inhalation), by injection, by infusion, by continuous infusion, localized perfusion bathing target cells directly, via a catheter, via a lavage, in cremes, in lipid compositions (e.g., liposomes), or by other methods or any combination of the foregoing as would be known to one of ordinary skill in the art (see, for example. Remington's Pharmaceutical Sciences, 18th Ed. Mack Printing Company, 1990).

The actual dosage amount of a composition administered to an animal patient can be determined by physical and physiological factors such as body weight, severity of condition, the type of disease being treated, previous or concurrent therapeutic interventions, idiopathy of the patient and the route of administration. The practitioner responsible for administration will, in any event, determine the concentration of active ingredient(s) in a composition and appropriate dose(s) for the individual subject.

In certain embodiments, pharmaceutical compositions can comprise, for example, at least about 0.1% of an active compound. In other embodiments, an active compound can comprise between about 2% to about 75% of the weight of the unit, or between about 25% to about 60%, for example, and any range derivable therein. In other non-limiting examples, a dose can also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition can comprise various antioxidants to retard oxidation of one or more component.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof. In many cases, isotonic agents can be included, such as, for example, sugars, sodium chloride or combinations thereof.

In other embodiments, one can use eye drops, nasal solutions or sprays, aerosols or inhalants. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in some embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, can be included in the formulation. For example, various commercial nasal preparations are known and include drugs such as antibiotics or antihistamines.

In certain embodiments the antibodies are prepared for administration by such routes as oral ingestion. In these embodiments, the solid composition can comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions can be incorporated directly with the food of the diet. Carriers for oral administration comprise inert diluents, assimilable edible carriers or combinations thereof. In other embodiments, the oral composition can be prepared as a syrup or elixir. A syrup or elixir, can comprise, for example, at least one active agent, a sweetening agent, a preservative, a flavoring agent, a dye, a preservative, or combinations thereof.

In certain embodiments an oral composition can comprise one or more binders, excipients, disintegration agents, lubricants, flavoring agents, and combinations thereof. In certain embodiments, a composition can comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations of the foregoing. When the dosage unit form is a capsule, it can contain, in addition to materials of the above type, carriers such as a liquid carrier. Various other materials can be present as coatings or to otherwise modify the physical form of the dosage unit. For instance, tablets, pills, or capsules can be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers can include, for example, polyalkylene glycols, triglycerides or combinations thereof. In certain embodiments, suppositories can be formed from mixtures containing, for example, the active ingredient in the range of about 0.5% to about 10%, and about 1% to about 2%.

The composition must be stable under the conditions of manufacture and storage, and preserved against the contaminating action of microorganisms, such as bacteria and fungi. It will be appreciated that endotoxin contamination should be kept minimally at a safe level, for example, less than 0.5 ng/mg protein.

In particular embodiments, prolonged absorption of an injectable composition can be brought about by the use in the compositions of agents delaying absorption, such as, for example, aluminum monostearate, gelatin or combinations thereof.

B. Pharmaceutical Uses

The monoclonal antibody can be used for therapeutic purposes for treating genetic and acquired deficiencies or defects in coagulation. For example, the monoclonal antibodies in the embodiments described above can be used to block the interaction of aPC with its substrate, which can include Factor Va or Factor VIIIa.

The monoclonal antibodies have therapeutic use in the treatment of disorders of hemostasis such as thrombocytopenia, platelet disorders and bleeding disorders (e.g., hemophilia A, hemophilia B and hemophilia C). Such disorders can be treated by administering a therapeutically effective amount of the anti-aPC monoclonal antibody to a patient in need thereof. The monoclonal antibodies also have therapeutic use in the treatment of uncontrolled bleeds in indications such as trauma and hemorrhagic stroke. Thus, also provided is a method for shortening the bleeding time comprising administering a therapeutically effective amount of an anti-aPC monoclonal antibody to a patient in need thereof.

In another embodiment, the anti-aPC antibody can be useful as an antidote for aPC-treated patients, including for example wherein aPC is used for the treatment of sepsis or bleeding disorder.

The antibodies can be used as monotherapy or in combination with other therapies to address a hemostatic disorder. For example, co-administration of one or more antibodies with a clotting factor such as factor VIIa, factor VIII or factor IX is believed useful for treating hemophilia. In one embodiment, provided is a method for treating genetic and acquired deficiencies or defects in coagulation comprising administering (a) a first amount of a monoclonal antibody that binds to human tissue factor pathway inhibitor and (b) a second amount of factor VIII or factor IX, wherein said first and second amounts together are effective for treating said deficiencies or defects. In another embodiment, provided is a method for treating genetic and acquired deficiencies or defects in coagulation comprising administering (a) a first amount of a monoclonal antibody that binds to human tissue factor pathway inhibitor and (b) a second amount of factor VIII or factor IX, wherein said first and second amounts together are effective for treating said deficiencies or defects, and further wherein factor VII is not coadministered. Also included is a pharmaceutical composition comprising a therapeutically effective amount of the combination of a monoclonal antibody and factor VIII or factor IX, wherein the composition does not contain factor VII. "Factor VII" includes factor VII and factor VIIa. These combination therapies are likely to reduce the necessary infusion frequency of the clotting factor. By co-administration or combination therapy is meant administration of the two therapeutic drugs each formulated separately or formulated together in one composition, and, when formulated separately, administered either at approximately the same time or at different times, but over the same therapeutic period.

In some embodiments, one or more antibodies described herein can be used in combination to address a hemostatic disorder. For example, co-administration of two or more of the antibodies described herein is believed useful for treating hemophilia or other hemostatic disorder.

The pharmaceutical compositions can be parenterally administered to subjects suffering from hemophilia A or B at a dosage and frequency that can vary with the severity of the bleeding episode or, in the case of prophylactic therapy, can vary with the severity of the patient's clotting deficiency.

The compositions can be administered to patients in need as a bolus or by continuous infusion. For example, a bolus administration of an inventive antibody present as a Fab fragment can be in an amount of from 0.0025 to 100 mg/kg body weight, 0.025 to 0.25 mg/kg, 0.010 to 0.10 mg/kg or 0.10-0.50 mg/kg. For continuous infusion, an inventive antibody present as an Fab fragment can be administered at 0.001 to 100 mg/kg body weight/minute, 0.0125 to 1.25 mg/kg/min., 0.010 to 0.75 mg/kg/min., 0.010 to 1.0 mg/kg/min. or 0.10-0.50 mg/kg/min. for a period of 1-24 hours, 1-12 hours, 2-12 hours, 6-12 hours, 2-8 hours, or 1-2 hours. For administration of an inventive antibody present as a full-length antibody (with full constant regions), dosage amounts can be about 1-10 mg/kg body weight, 2-8 mg/kg, or 5-6 mg/kg. Such full-length antibodies would typically be administered by infusion extending for a period of thirty minutes to three hours. The frequency of the administration would depend upon the severity of the condition. Frequency could range from three times per week to once every two weeks to six months.

Additionally, the compositions can be administered to patients via subcutaneous injection. For example, a dose of 10 to 100 mg anti-aPC antibody can be administered to patients via subcutaneous injection weekly, biweekly or monthly.

As used herein, "therapeutically effective amount" means an amount of an anti-aPC monoclonal antibody or of a combination of such antibody and factor VIII or factor IX that is needed to effectively increase the clotting time in vivo or otherwise cause a measurable benefit in vivo to a patient in need. The precise amount will depend upon numerous factors, including, but not limited to the components and physical characteristics of the therapeutic composition, intended patient population, individual patient considerations, and the like, and can readily be determined by one skilled in the art.

V. KITS

Any of the compositions described herein can be comprised in a kit. The kits will thus comprise, in suitable container, an antibody and/or an additional agent. Other components can be included in a kit. Diagnostic and therapeutic kits comprise in suitable container, a pharmaceutically acceptable formulation of an antibody in a pharmaceutically acceptable formulation. The kit can have a single container, and/or it can have distinct container for each compound.

When the components of the kit are provided in one and/or more liquid solutions, the liquid solution is an aqueous solution, with a sterile aqueous solution being one example of a particular embodiment. The antibody can also be formulated into a syringeable composition, in which case, the container can itself be a syringe, pipette, and/or other such like apparatus, from which the formulation can be applied to an infected area of the body, injected into an animal, and/or even applied to and/or mixed with the other components of the kit.

However, the components of the kit can be provided as dried powder(s). When reagents and/or components are provided as a dry powder, the powder can be reconstituted by the addition of a suitable solvent. It is envisioned that the solvent can also be provided in another container.

The container will generally include at least one vial, test tube, flask, bottle, syringe and/or other container, into which the antibody/antibody formulation is placed, suitably allocated. The kits can also comprise a second container for containing a sterile, pharmaceutically acceptable buffer and/or other diluent.

The kits can also include a means for containing the vials in close confinement for commercial sale, such as, e.g., injection and/or blow-molded plastic containers into which the desired vials are retained.

Irrespective of the number and/or type of containers, the kits can also comprise, and/or be packaged with, an instrument for assisting with the injection/administration and/or placement of the ultimate antibody within the body of an animal. Such an instrument can be a syringe, pipette, forceps, and/or any such medically approved delivery vehicle.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods

Transient transfection of HEK293 cells. Approximately 24 hrs before transfection. FreeStyle™ 293E cells were passaged at $0.5 \times 10^6$ cells/ml and shaken at 120 rpm/min, at 37° C., 8% $CO_2$. On the day of transfection, the cell density was about $1.0-1.2 \times 10^6$ cells/ml. The cells were split to $1 \times 10^6$ cells/ml with growth medium. To ensure optimal transfection, viability of the cells was determined to be >95%. DNA was diluted in FreeStyle™ 293 expression medium (293E) in a volume equivalent to one-tenth of culture transfected. PEI was added into DNA; the mixture was vortex immediately and incubated for 10 min at room temperature prior to its addition to the cells. The final concentration of DNA to PEI ratio was 1:2.

Purification of Humanized 1573 IgG Antibodies.

Conditioned medium (Day 6 after transfection) was loaded onto a 1 ml Protein A column, which was pre-equilibrated with 10 ml PBS, pH 7.0. The column was then washed with equilibrating buffer to baseline after sample loading. After washing, the column was eluted with 100 mM Glycin-HCl, pH3.0, followed with immediate addition of 1M Tris-HCl solution to adjust the pH to 8.0. The final product was dialyzed against PBS solution. Protein purity was analyzed by SDS-PAGE, SEC and its concentration was determined by the Bradford method.

Size Exclusion Chromatography Analysis of the Purified Antibodies.

SEC for analyzing purified antibody was carried out with a Superdex 200 5/150, GL column using a HPLC system (LC-20AD, Shimadzu) at ambient temperature. PBS buffer, pH 7.0, at a flow rate 0.3 ml/min was used as the mobile phase. The protein detection was performed at 280 nm.

Immobilization of anti-mouse FC antibody onto CM5 Chip.

A CM4 or CM5 sensor chip was activated in FC2 and 4 by a 6-min injection (10 µl/min) of freshly prepared 1:1 50 mM NHS: 200 mM EDC. Then ligand capture antibody (30 µg/ml anti-mIgG; GE Healthcare) in 10 mM sodium acetate buffer, pH 5.0 (1.4 µl diluted in 90 µl NaAc, pH 5.0) was injected onto the activated chip at 5 µl/min (HBS-EP running buffer: 10 mM HEPES, pH 7.4, 150 mM NaCl, 3.4 mM EDTA, 0.005% surfactant P20). The remaining active coupling sites were blocked by injection of 35 µl of 1M ethanolamine at 5 µl/min. About 2000-2500 RU was produced for affinity measurements. FC1 and 3 were used as blanks.

Immobilization of Anti-Human FC Antibody onto CM5 Chip.

A CM5 sensor chip was activated in FC2 by a 7-min injection (10 µl/min) of freshly prepared 1:1 50 mM NHS: 200 mM EDC. Then anti-human FC antibody in 10 mM sodium acetate buffer pH 5.0 (2.5 µl diluted in 90 µl NaAc, pH 5.0) was injected onto the activated chip at 5 µl/min (HBS-EP running buffer: 10 mM HEPES, pH 7.4, 150 mM NaCl, 3.4 mM EDTA, 0.005% surfactant P20). The remaining active coupling sites were blocked with a 7-min injection of 1M ethanolamine at 10 µl/min. About 6400 RU was produced.

Biacore Analysis of Human aPC Binding to Optimized Antibodies.

The test antibody (10 µg/ml anti-APC type II antibody in HBS-P, pH 7.4) was first captured on the anti-human FC IgG coated CM5 chip by injection for 60 sec at a flow rate of 5 µl/min, yielding a capture level of about 230 RU. Then, binding of the analyte (wild-type or mutant hAPC protein at to two different concentrations, 100 and 200 nM, in HBS-P, pH 7.4) was measured. Cycle conditions were as follows: 30 µl/min for 90 s of association phase and 350-500 s of dissociation phase. The surface was regenerated with a 30 s injection of 10 mM Glycine, pH 1.7, at 5 µl/min. HBS-EP running buffer: 10 mM HEPES. pH 7.4, 150 mM NaCl, 3.4 mM EDTA, 0.005% surfactant P20. Kinetics were calculated with BIAevaluation Software.

Binding ELISA of Purified Antibodies.

Plates (Nunc, cat #442404) were coated with 100 µl of human aPC (1 µg/ml) or hPC (2 µg/ml) diluted in DPBS (Gibco, cat #14040) overnight (o/n) at 4° C. After washing, the ELISA plate was blocked with 200 µl MPBST for 1 hr at RT, and tapped dry on a stack of paper towels. To each well 100 µl of IgG to be tested was added, and incubated for 1 hr at RT (for $EC_{50}$ determinations 1:3 dilutions were performed starting at 20 nM). Plates were washed 5× with PBST. 100 µl of anti-hIgG Fc-HRP (Sigma, cat #A0170) diluted 1:10,000 in PBST was added to each well. Plates were washed and 100 µl/well of TMB substrate was added and incubated at room temperature for 5 min. 100 µl/well of 1 N HCl was added to terminate the reaction. The plate was read with an ELISA plate reader (Biotek, Elx405) at 450 nm wavelength.

Example 2—Optimization of Humanized 1573

A mouse anti-human aPC antibody 1573 (mIgG1/k) was previously generated via hybridoma technology. All 6 mouse CDRs from antibody 1573 (mIgG1/k) were grafted onto human IgG1 frameworks (VH3-72 and VK2D-29), resulting in the humanized 1573 TPP-1940 (hIgG1/k), which had a high in silico immunogenicity score (830) and poor expression titers in mammalian cells (<20 mg/L 653). Back mutations were also introduced to conserve aPC-binding affinity and specificity.

Germlining of all CDRs and frameworks led to generation of 2 germlined variants (TPP-3356/3357) with reduced immunogenicity scores. They were further optimized by framework-shuffling with additional mutations. Optimized antibodies (TPP-3656/3657/3658/3639) show improved expression titers and thermal stability while conserving aPC-binding affinity and specificity.

Germlining.

In order to reduce immunogenicity and to improve expression titer of the humanized 1573 (TPP-1940), all CDRs and frameworks were germlined while conserving aPC-binding affinity and specificity. Two germlined humanized antibodies (TPP-3356/3357) were created. The isotype of TPP-3356/3357 was changed to hIgG2 to avoid any potential antibody effector functions, such as ADCC and CDC, due to safety concerns. Their immunogenicity scores were reduced to 772 for TPP-3356 and 653 for TPP-3357. The antibodies retained aPC-binding affinity as determined by SPR (Table 1). Furthermore, TPP-3356/3357 retained specificity for aPC, as no binding to human PC was observed. However, TPP-3356/3357 showed poor thermal stability as reflected by a low Tm (62-63° C.) and non-cooperative melting behaviors, in addition to low expression levels in HEK293 or CHO cells.

(the original VH sequence of TPP-3357); and where L-chains were selected from: KV2D-29 with corrected canonical structure (insertion of L in LCDR1); KV7-3; KV4-1. KV4-1 with LY insertion in LCDR1; KV2-30-2; or KV2-30-2 with L insertion in LCDR1.

Fifteen variants of TPP-3356 were created where H-chains were selected from: VH3-72 with full HCDR3; VH3-7 with RL deletion in HCDR3; or VH3-48 is the original VH sequence of TPP-3356; and where L-chains were selected from: KV2D-29 with corrected canonical structure (insertion of L in LCDR1); KV7-3; KV2D-28; KV2D-28 with L insertion in LCDR1; or KV2-24.

TABLE 1

Comparable binding affinities for germlined humanized antibodies (TPP-3356 and 3357) vs. Ab1573 for human aPC by SPR

| Anti-aPC antibody | | On-rate ka (s−1) | Off-rate kd (M−1s−1) | Binding affinity KD (M) |
|---|---|---|---|---|
| TPP-3356 | H1573VK2_1_R24K_VH1C | 6.37E+05 | 0.008666 | 1.36E−08 |
| TPP-3357 | H1573VK2A_VH1C_3_N31S | 5.11E+05 | 0.01196 | 2.34E−08 |
| Parental Ab 1573 (mIgG1/k) | | 8.06E+05 | 0.008486 | 1.05E−08 |

Framework Shuffling.

The germlined 1573 (TPP-3356/3357) antibodies were further optimized by framework-shuffling with additional mutations to improve expression titer and thermal stability. New variants were derived from different combinations of heavy (H)-chain and light (L)-chain frameworks while conserving the CDRs from TPP-3356/3357.

Eighteen variants of TPP-3357 were created where H-chains were selected from: VH3-48 with RL deletion in HCDR3; VH3-7 with full HCDR3; or VH3-72 of TPP-3357

Transient transfection experiments of these antibody expression vectors in HEK293 cells showed that 4 out of 33 variants (TPP-3656/3657/3658/3639) produced 50-100 mg/L IgG. These four optimized 1573 TPP-3656/3657/3658/3639 antibodies contain the same VK7-3 as their LC framework, but their HC framework varied (VH3-72/VH3-7delRL/VH3-7 and VK3-7). These four antibodies had good expression titers in HEK293 cells and had improved thermal stability while conserving aPC binding affinity/specificity and conserving aPC-inhibition activity like TPP-1940 (Table 2). Moreover, immunogenicity scores were 764/642/848/690 for TPP-3656/3657/3658/3639, respectively.

TABLE 2

Use of the Light Chain Framework VK7-3 Improved Antibody Expression Titer and Thermal Stability for the optimized germlined TPP-3639/3656/3657/3658

Figure 2:
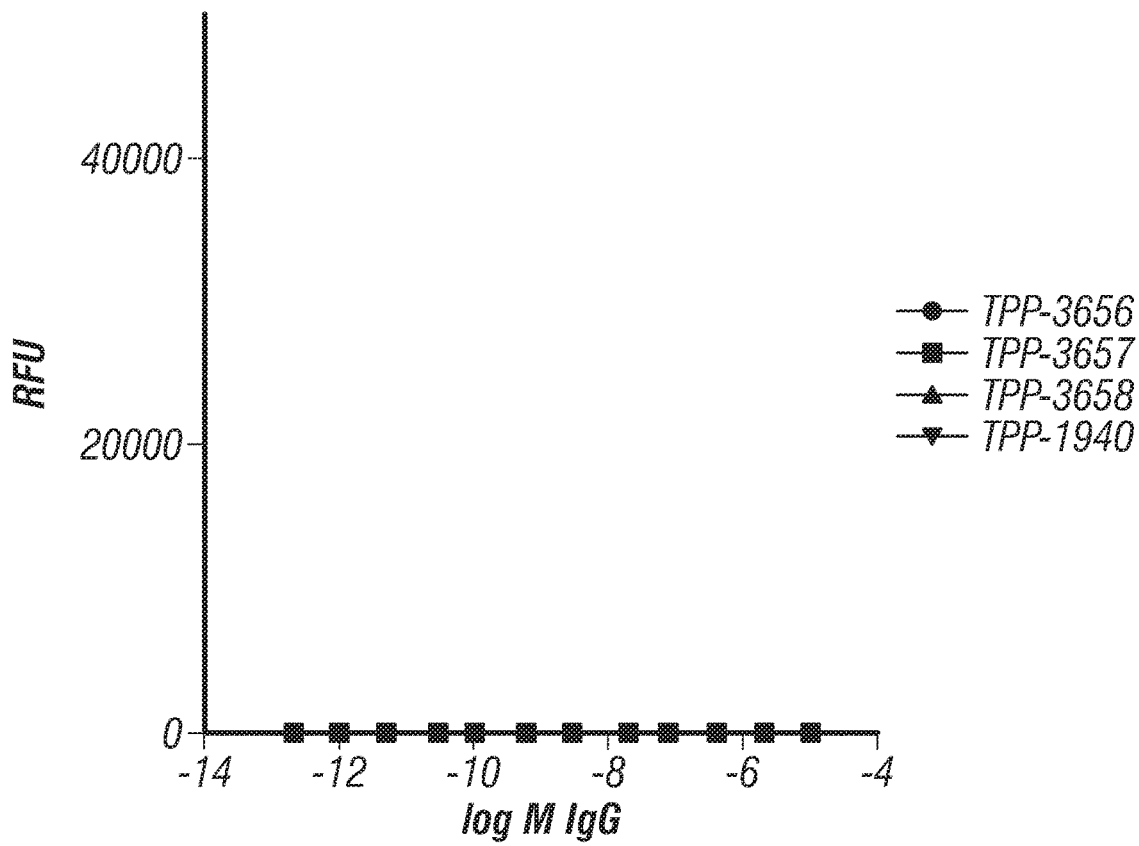
FIG. 2. PC binding for the optimized germlined anti-aPC IgGs. Titration of anti-aPC IgGs in a PC-ELISA. These data correspond to data summarized in Table 2.
Figure 3:
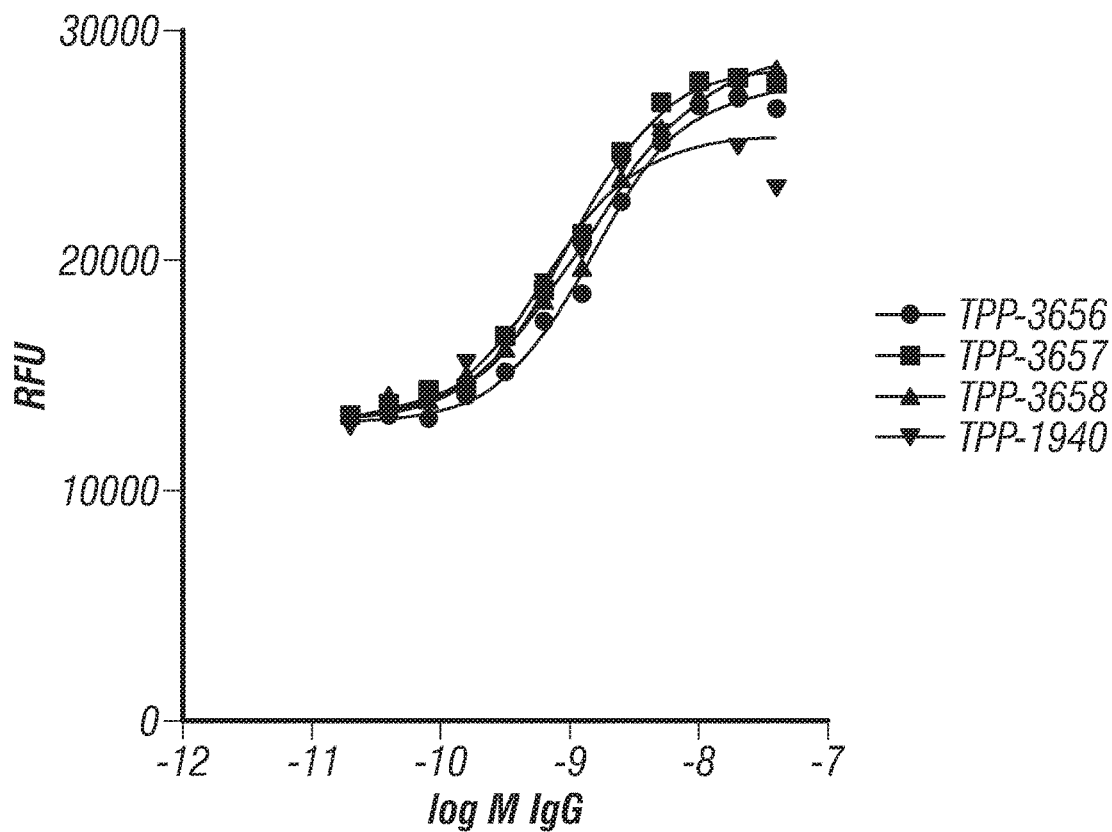
FIG. 3. aPC activity for the optimized germlined anti-aPC IgGs. Anti-aPC IgGs in an aPC activity assay. These data correspond to data summarized in Table 2.
Figure 4A:
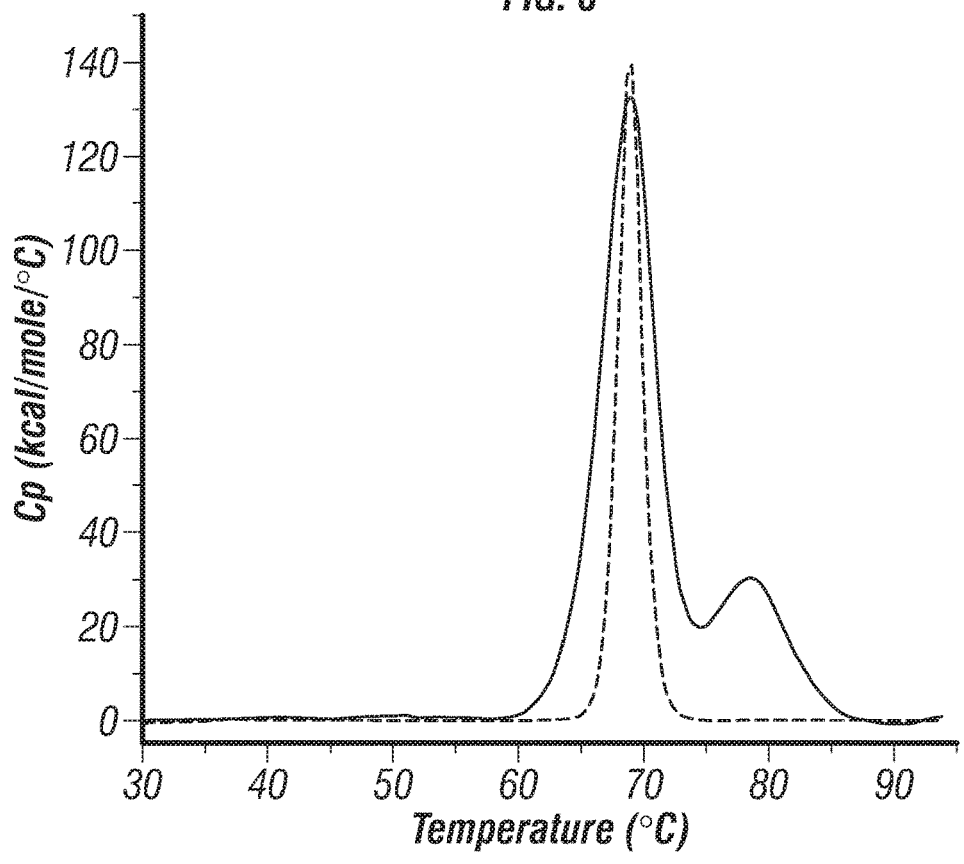
FIGS. 4A-C. Thermal Stability for the optimized germlined anti-aPC IgGs. 4A is TPP-3656.
Figure 4B:
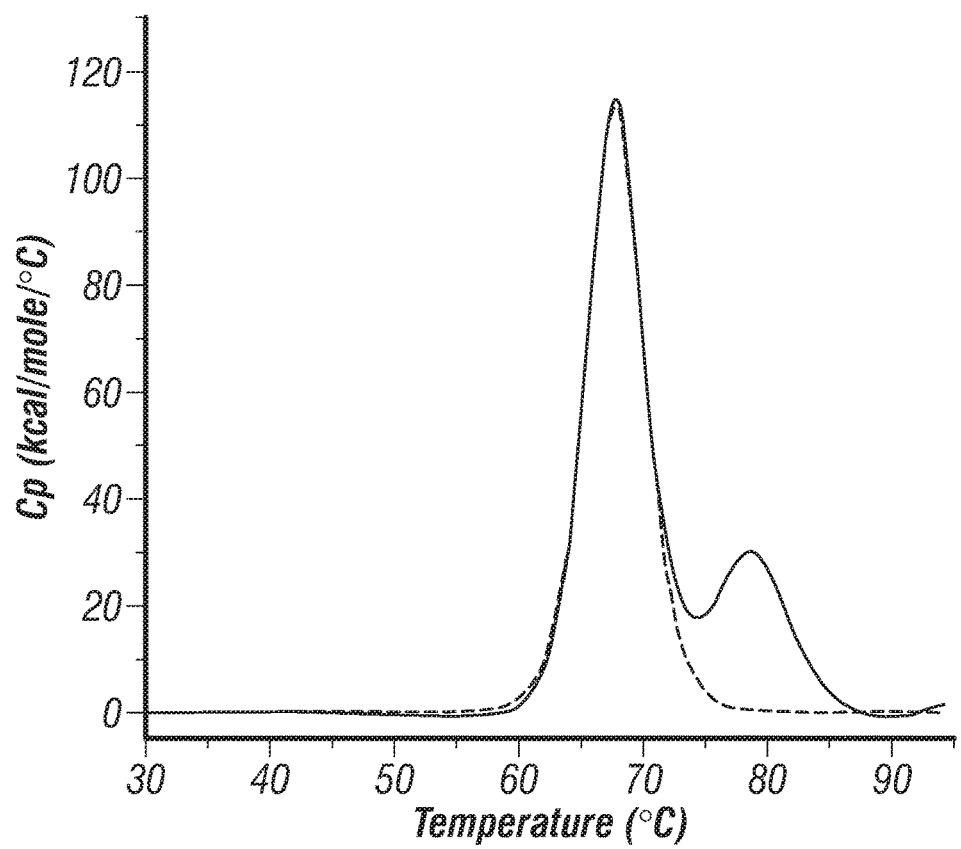
Figure 4C:
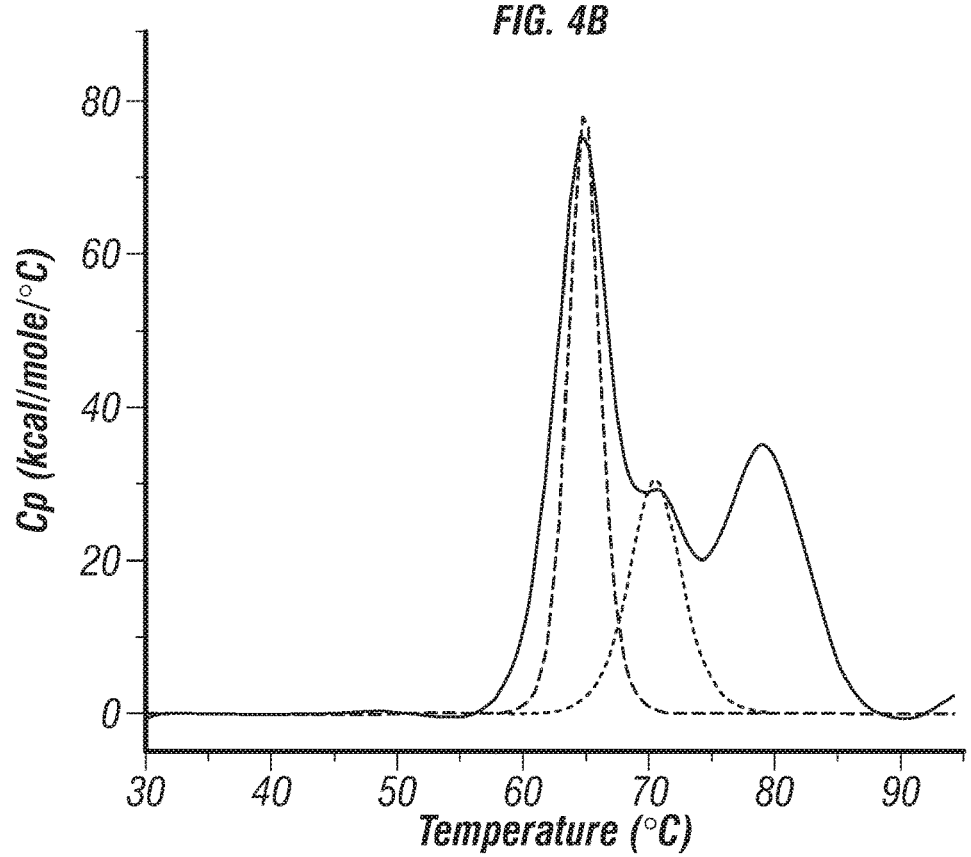

| TPP No. | aPC binding activity by ELISA (EC50 value: TPP-1940/1573 0.2-0.8 nM) (see FIG. 1) | PC-binding by ELISA (see FIG. 2) | Inhibition of aPC amidolytic activity (see FIG. 3) | In silico Immunogenicity score | Expression titer in HEK293 (mg/L) | Thermal Stability Tm (° C.) (see FIGS. 4A-C) |
|---|---|---|---|---|---|---|
| TPP-3639 VK7-3 | 0.42 nM | no binding | ≡ TPP-1940 | 690 | 57 | n.d. |
| TPP-3656 VK7-3 | 0.67 nM | no binding (up to 10 μM) | ≡ TPP-1940 | 764 | 70 | 68.9 (coop) |
| TPP-3657 VK7-3 | 0.43 nM | no binding (up to 10 μM) | ≡ TPP-1940 | 642 | 104 | 67.2 (coop) |
| TPP-3658 VK7-3 | 0.65 nM | no binding (up to 10 μM) | ≡ TPP-1940 | 847 | 110 | 64.9/70.5 (non-coop) |
| TPP-3356 VK2D-29 | 0.5 nM | no binding (up to 10 μM) | ≡ TPP-1940 | 772 | 1.8 | 63.5/70 (non-coop) |

Example 3—1573 Antibody Binding Characterization

Figure 5:
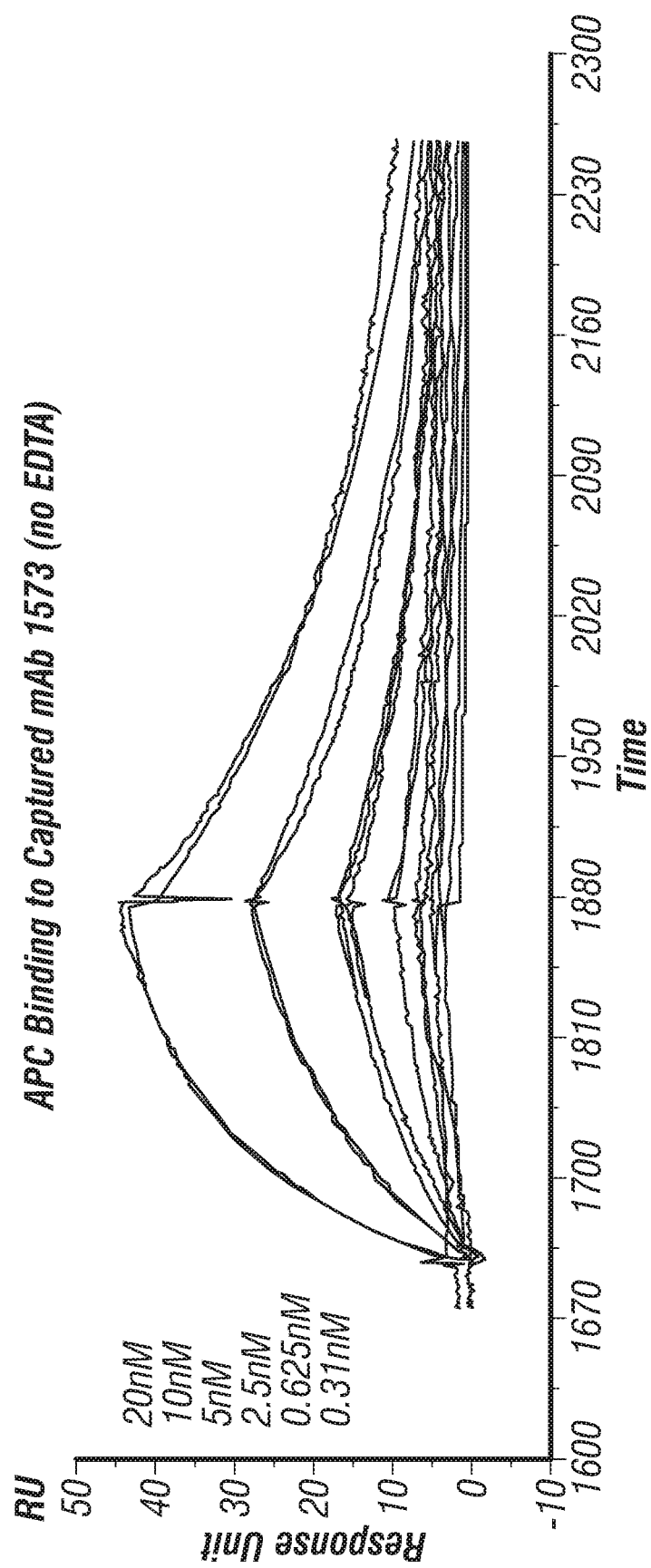
FIG. 5. Effects of PPACK on APC binding to Mabs 1573 and C25K23 by Biacore. Data were fitted to a Langmuir 1:1 model. Kinetics and affinity data corresponding to these experiments are provided in Table 3.
Figure 5:
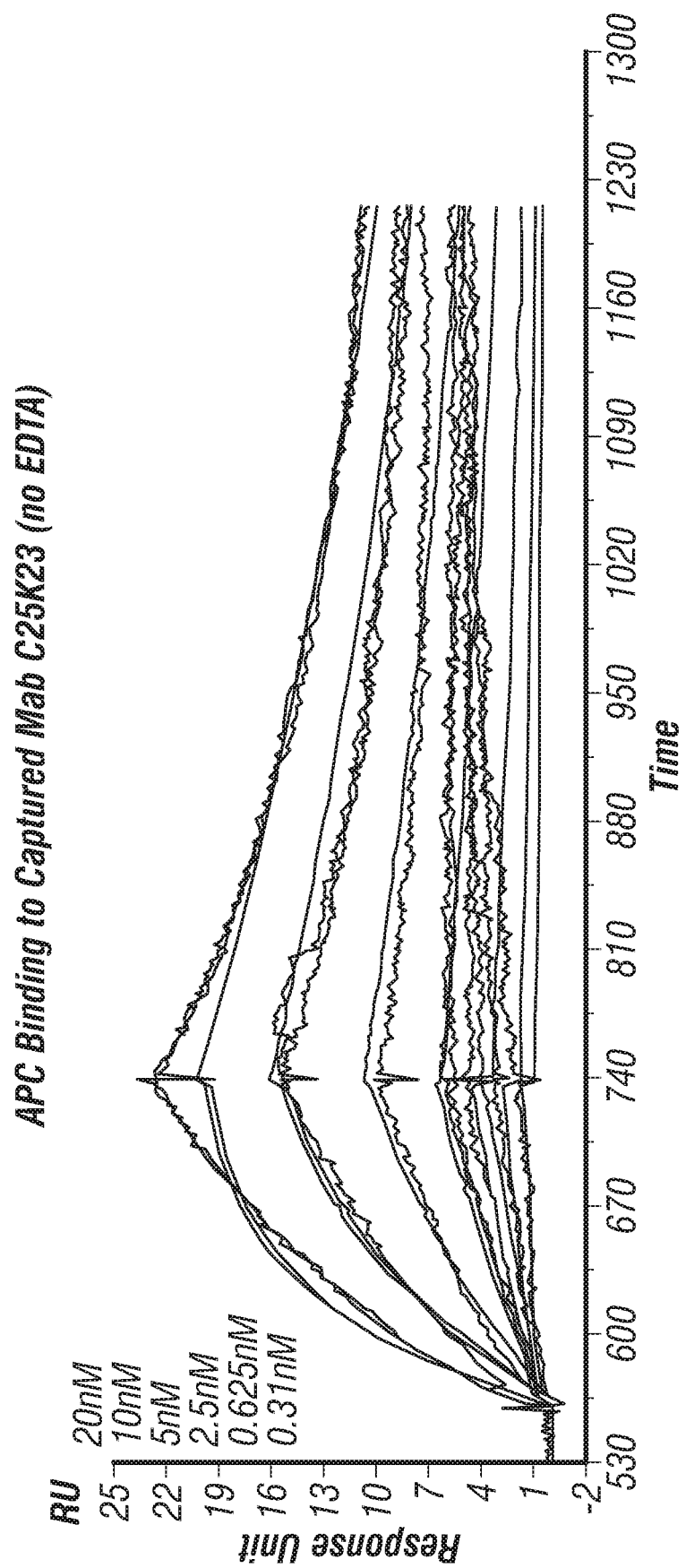
Figure 5:
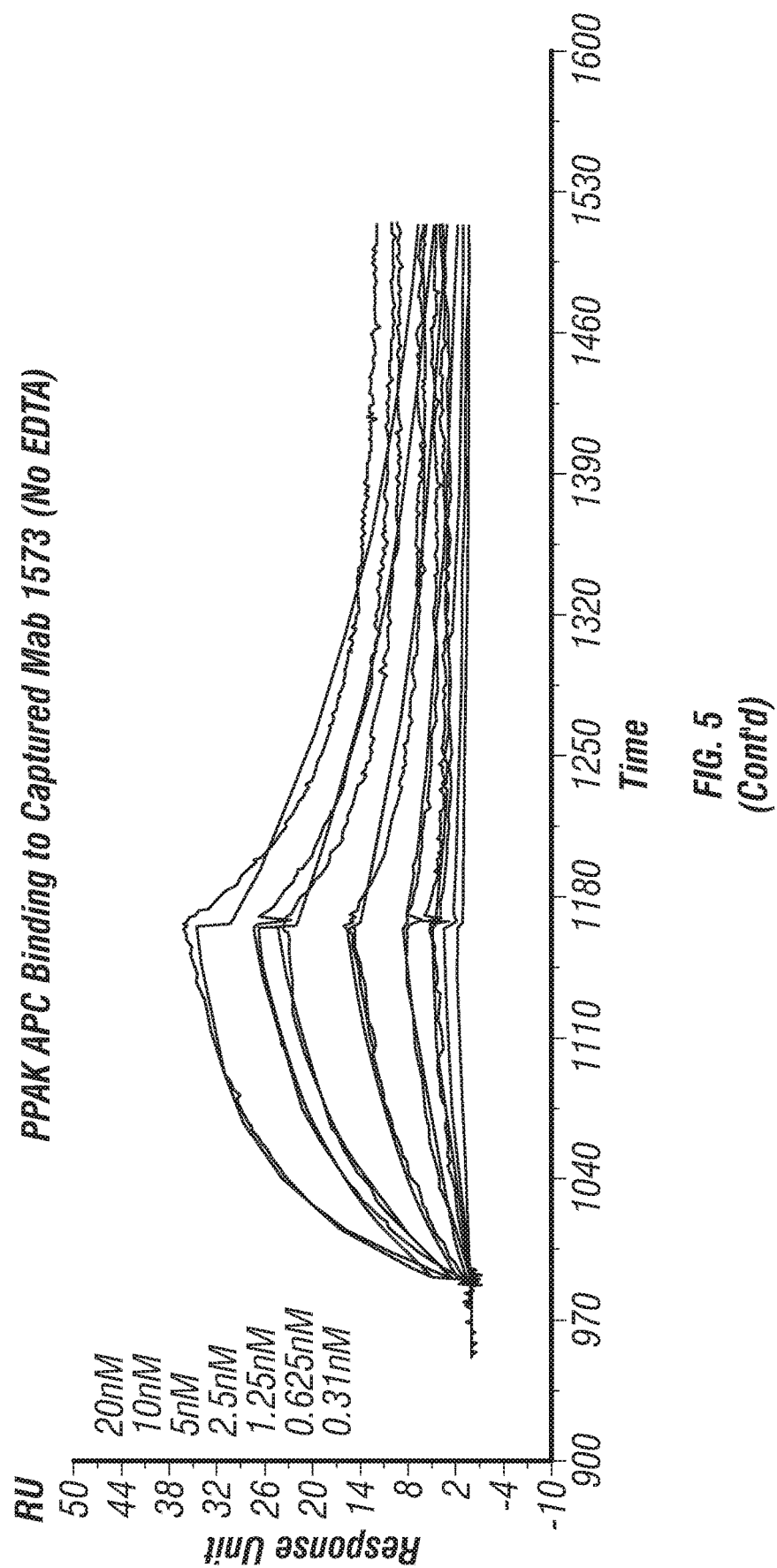
Figure 5:
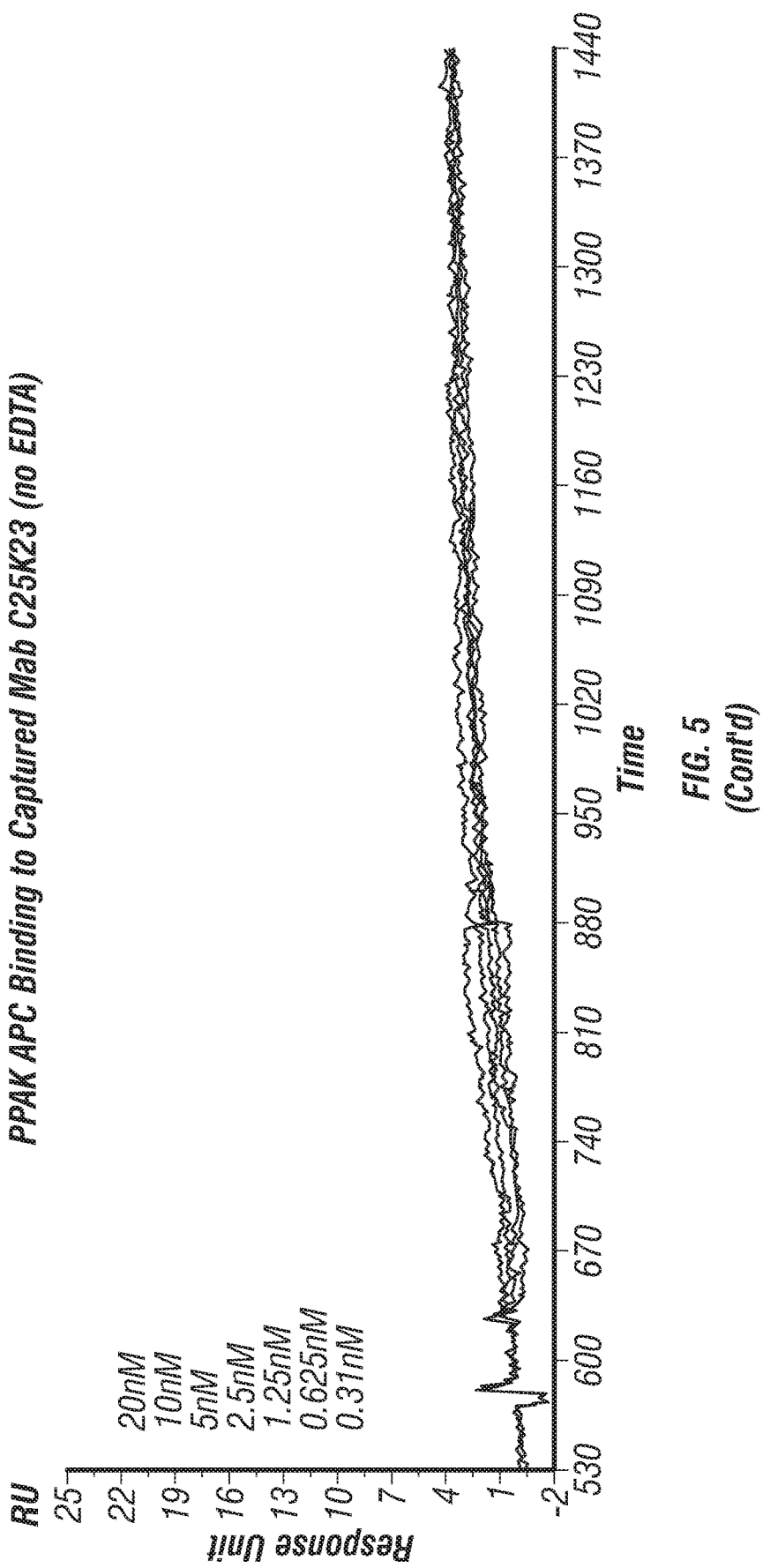

The Surface Plasmon Resonance (SPR) method was used to determine the effect of PPACK modification of the aPC active site on antibody binding affinity and kinetics. Anti-aPC IgGs were captured by immobilized anti-human or anti-mouse IgG Fc capture antibodies on a biochip. hAPC antigen (Xigris or Xigris-PPACK) was injected in HBS-P. pH 7.4 from 200-0.312 nM in two-fold dilutions in duplicate. Anti-IgG levels were regenerated after each antigen injection. In this experiment, antibody C25K23, which is known to bind the aPC active site based on X-ray structure (2.2 Angstrom), was used as a reference. PPACK modification of the aPC active site blocked antibody C25K23-aPC binding. In contrast, PPACK modification of the aPC active site did not affect 1573 antibody binding to aPC (FIG. 5 and Table 3). These data suggest that the active site of aPC is not required for 1573 binding. Thus, 1573 Ab is not an aPC-active site binder.

TABLE 3

PPACK modification of the aPC active site does not affect 1573 antibody binding to aPC by SPR. Corresponding sensorgrams are provided in FIG. 5

| Mab | Analyte | $k_a$ (1/Msec) | $k_d$ (1/sec) | $K_A$ (1/M) | $K_D$ (M) | Chi$^2$ |
|---|---|---|---|---|---|---|
| 1573 | Xigris | 5.78E05 | 4.56E-03 | 1.27E08 | 7.89E-09 | 2.3 |
| 1573 | Xigris + PPACK | 7.24E05 | 4.46E-03 | 1.67E08 | 5.97E-09 | 0.919 |
| C25K23 | Xigris | 2.12E05 | 1.48E-03 | 1.43E08 | 6.98E-09 | 1.56 |
| C25K23 | Xigris + PPACK | | | ---(no binding)--- | | |

Example 4—Comparative Studies on Parental and Optimized Antibodies

Figure 6:
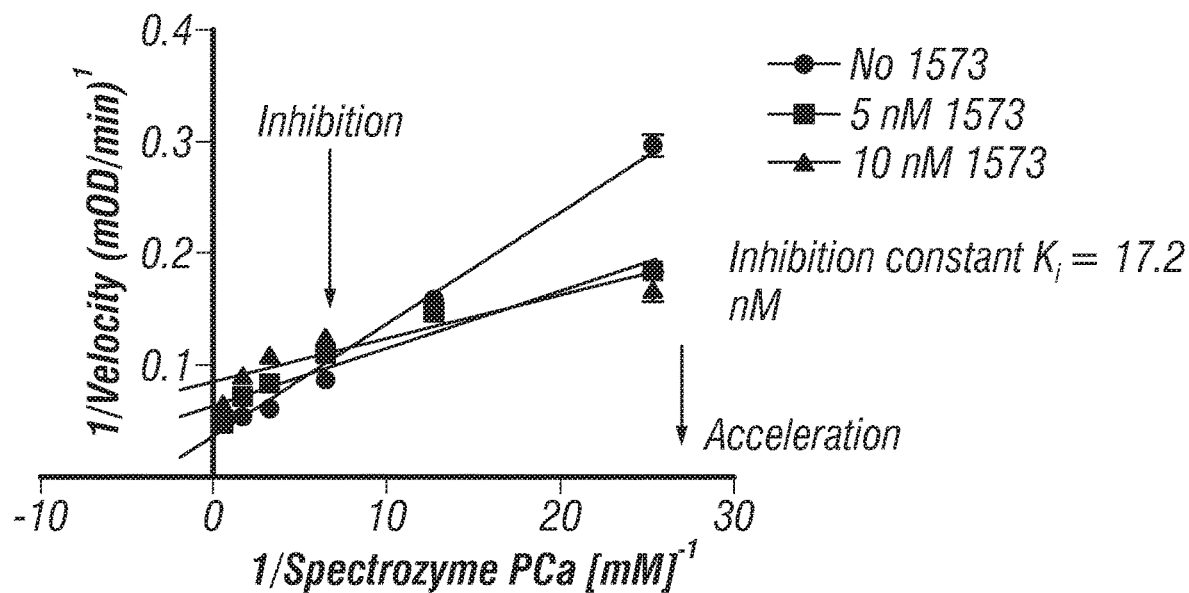
FIG. 6. Lineweaver-Burk plot of mAb 1573 on APC cleavage of Spectrozyme PCa. Type II parental antibody 1573 inhibits APC cleavage of small substrate Spectrozyme PCa at high substrate concentrations but accelerates the cleavage of the substrate by APC at low substrate concentrations.
Figure 7:
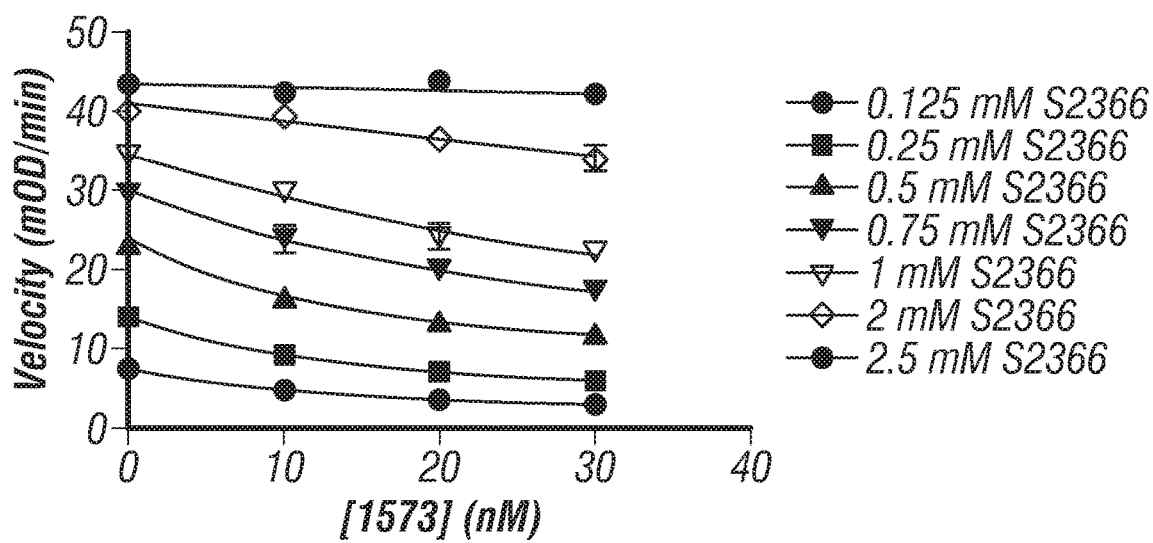
FIG. 7. Hydrolysis of S2366 by APC in the Presence of Ab 1573. Parental Type II antibody 1573 partially inhibits APC cleavage of small substrate S2366.

In amidolytic assays using small oligopeptidic substrates Spectrozyme PCa and S2366, type II antibodies (mAb 1573) partially inhibited the activity of APC. This inhibition was substrate and substrate-concentration dependent, was of a complex nature and did not conform to traditional classifications of "competitive" or "non-competitive" type inhibition (FIGS. 6-7).

FVa is a cofactor for the generation of thrombin by the prothrombinase complex (Factor Xa-FVa and phospholipids). FVa increases the rate of thrombin generation by the prothrombinase complex by 200,000-fold. Thus FVa is absolutely necessary for the amplification of thrombin generation and hence clot formation.

Figure 8:
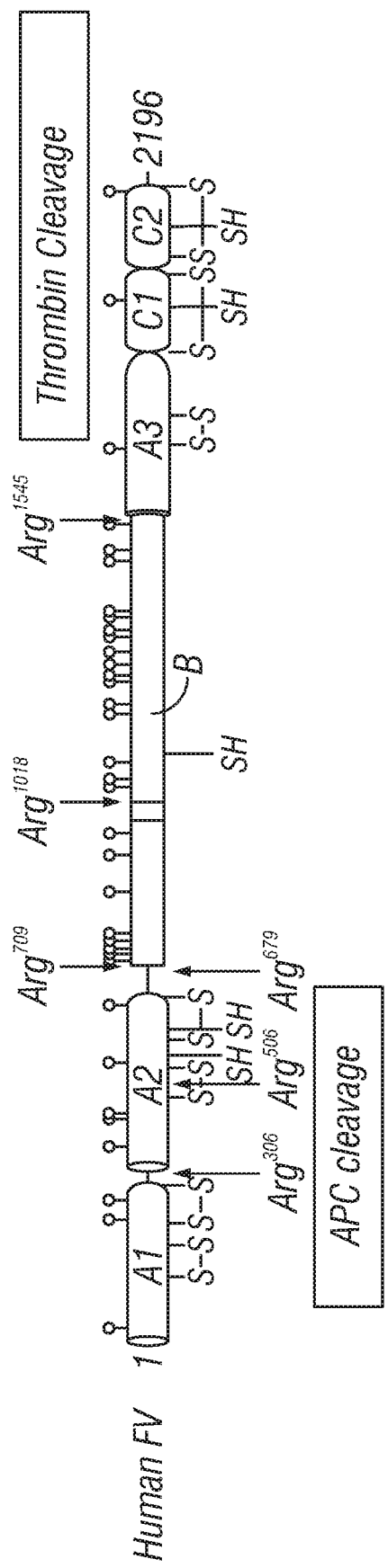
FIG. 8. Thrombin activates single-chain Factor V to two-chain Factor Va in a feedback loop.

Thrombin activates single-chain Factor V to two-chain Factor Va in a feedback loop (FIG. 8). APC regulates thrombin generation by proteolytically cleaving and inactivating FVa. APC cleaves FVa at three places on the A2 domain of the heavy chain of FVa (at Arg 506, 306 and 679). Proteolytic cleavage of FVa at Arg 506 is kinetically favored and results in loss of FVa cofactor activity. The cleavage at Arg 306 accounts for the loss or the remaining cofactor activity of FVa. The cleavage at Arg 679 is not associated with loss of any functional activity of FVa.

Figure 9:
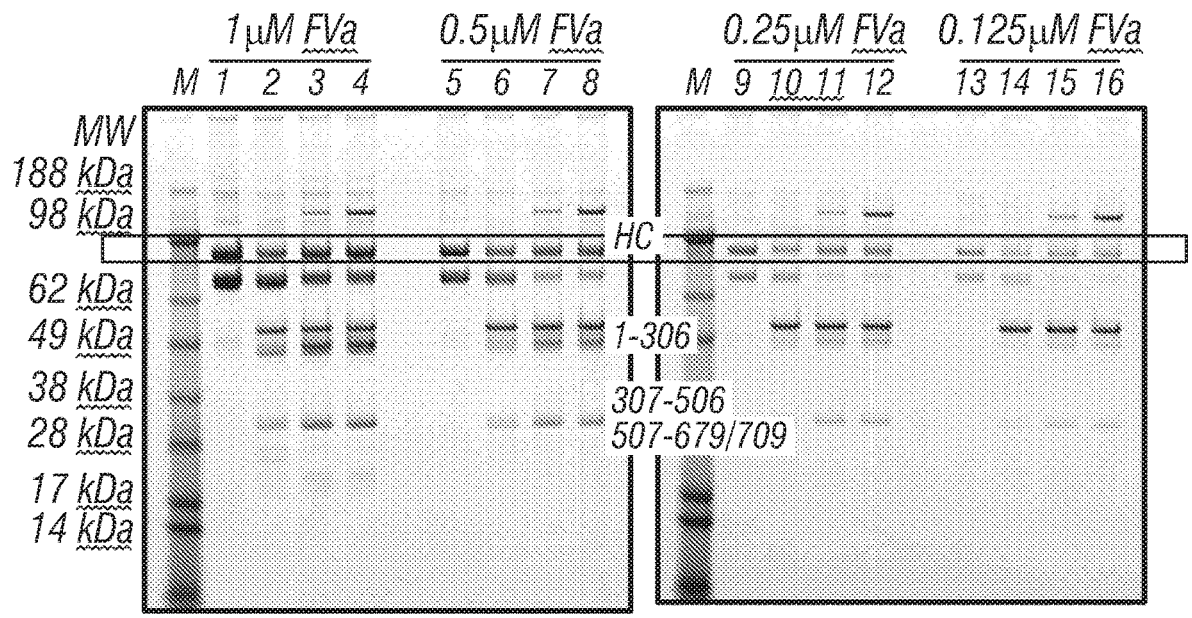
FIG. 9. FVa Heavy chain cleavage by APC is protected by type II parental ab 1573 at 4 different FVa concentrations (1
Figure 10:
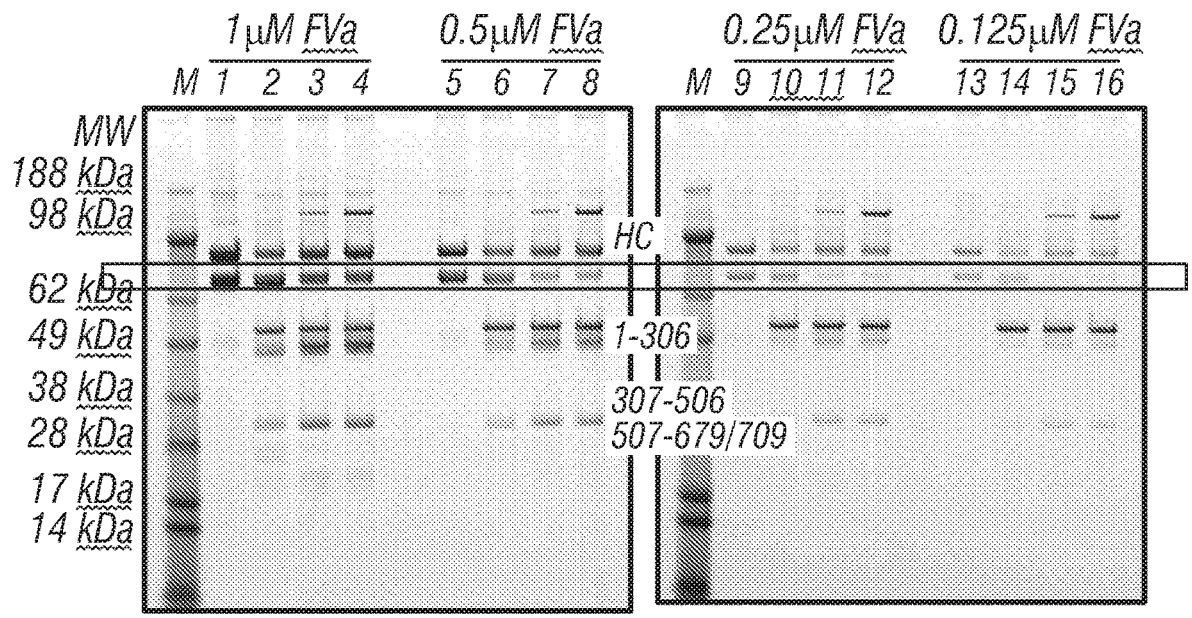

When FVa was used as a substrate for APC, type II abs inhibited the heavy chain cleavage of FVa by APC, whereas they accelerated the light chain cleavage of FVa by APC. The inhibition of FVa heavy chain cleavage and the acceleration of the light chain cleavage in the presence of type II abs were evident at different concentrations of FVa suggesting that this phenomenon was not substrate concentration dependent (FIGS. 9 and 10).

Figure 11A:
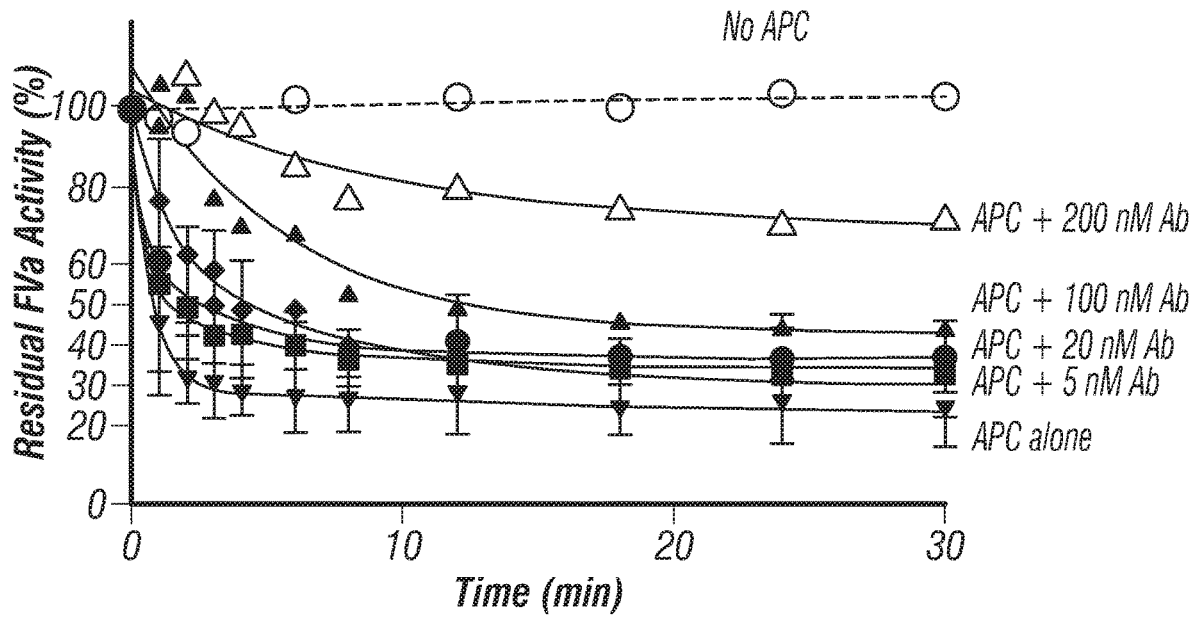
Figure 11B:
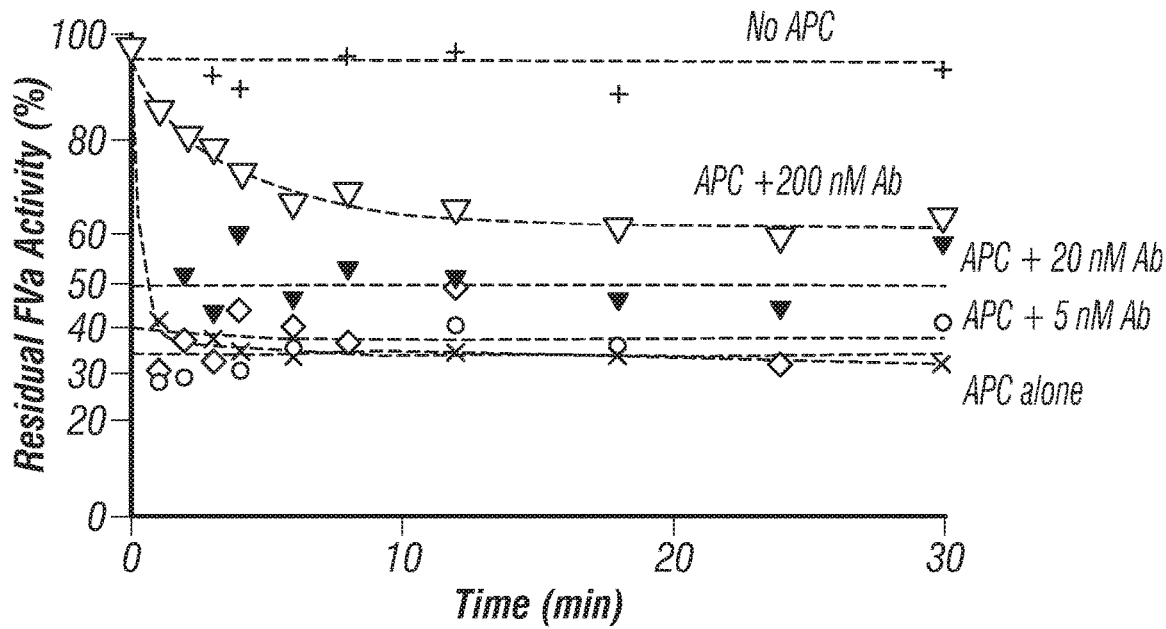
Figure 12:
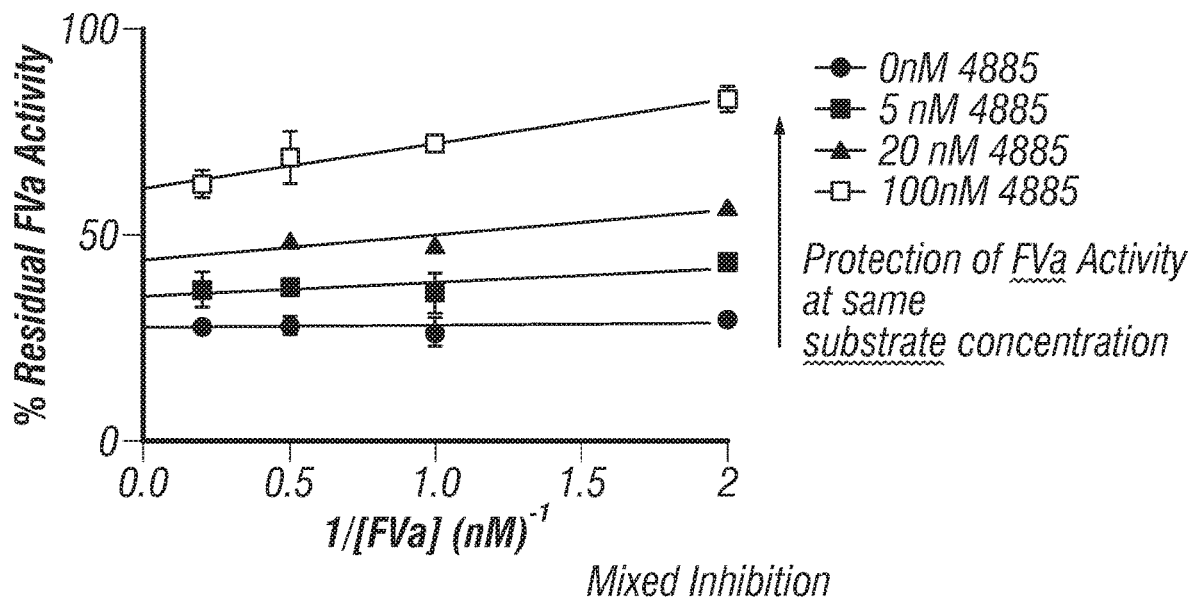
FIG. 12. Lineweaver-Burk plot of TPP 4885 on APC inhibition of FVa. Type II ab TPP4885 (BAY1896502) protects FVa activity from APC inactivation at both low and high FVa concentrations suggesting it is not a competitive (active site) inhibitor of APC. TPP4885 contains the N85D mutation in the light chain of TPP3656.

In purified system assays, type II abs 1573 and TPP4885 (BAY1896502) partially protected the functional activity of FVa from APC-dependent inactivation in a dose-dependent fashion (FIGS. 11A-B). This restoration of FVa activity from APC inactivation was also evident at high concentrations of FVa suggesting that type II antibodies are not competitive inhibitors of APC (FIG. 12).

Figure 13A:
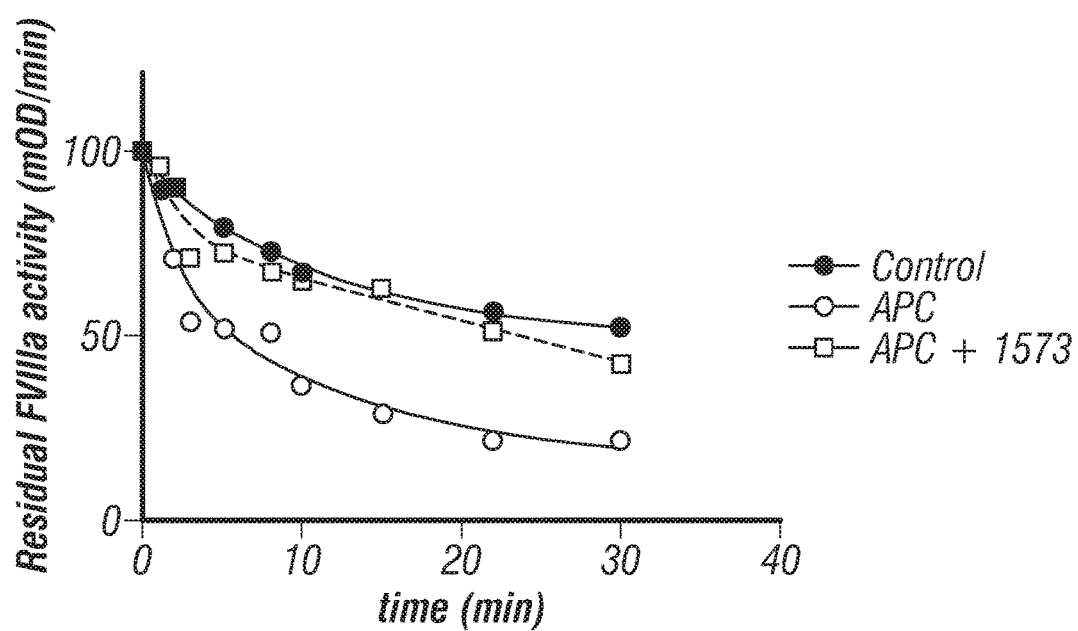
FIG. 13A. Type II parenetal Ab 1573 completely protected FVIIIa from APC inactivation.
Figure 13B:
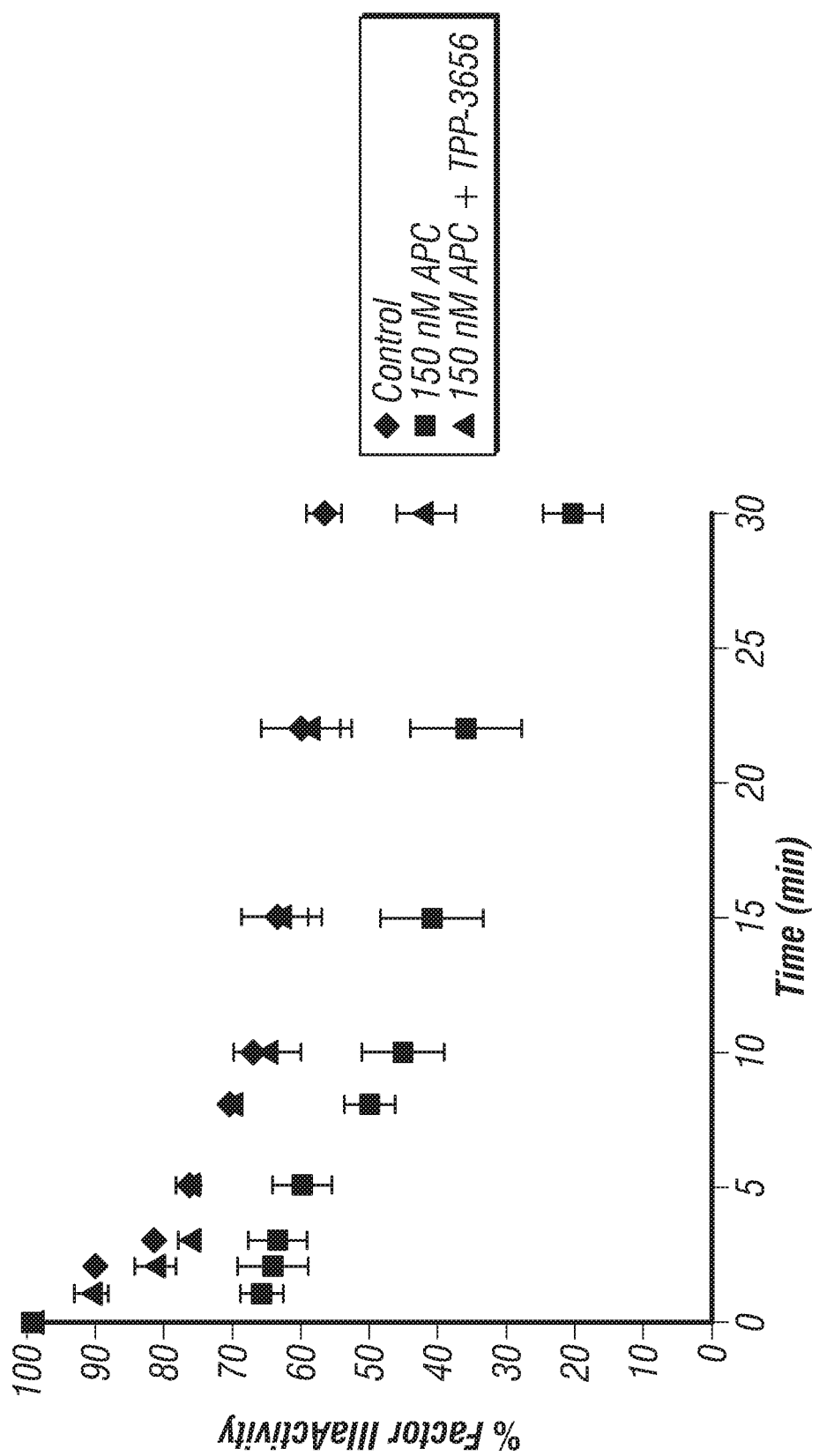
FIG. 13B. Type II those with skill in the art, and the fragments are analyzed for utility in the same manner as are intact antibodies.
Figure 14A:
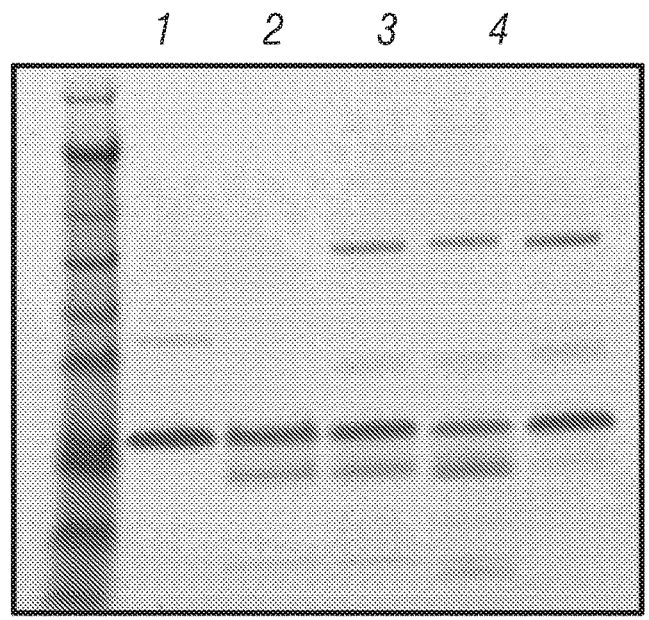
Figure 14B:
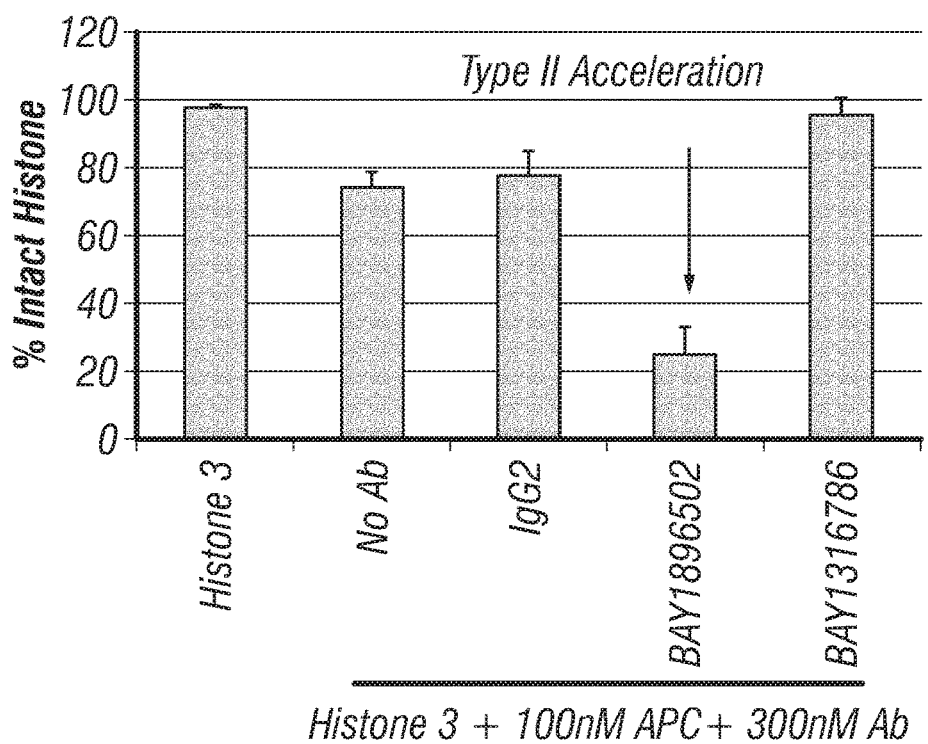
Figure 15A:
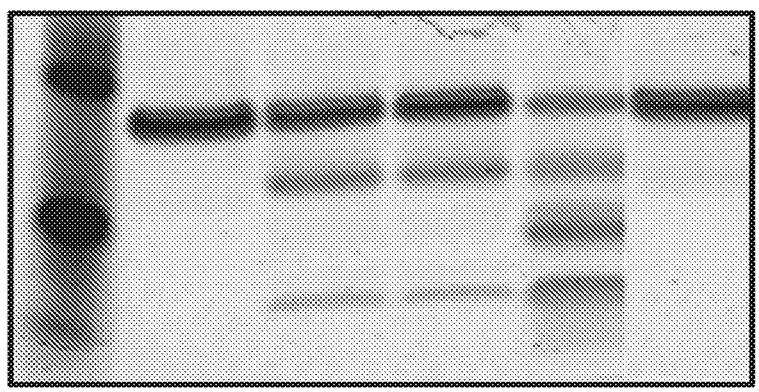
Figure 15B:
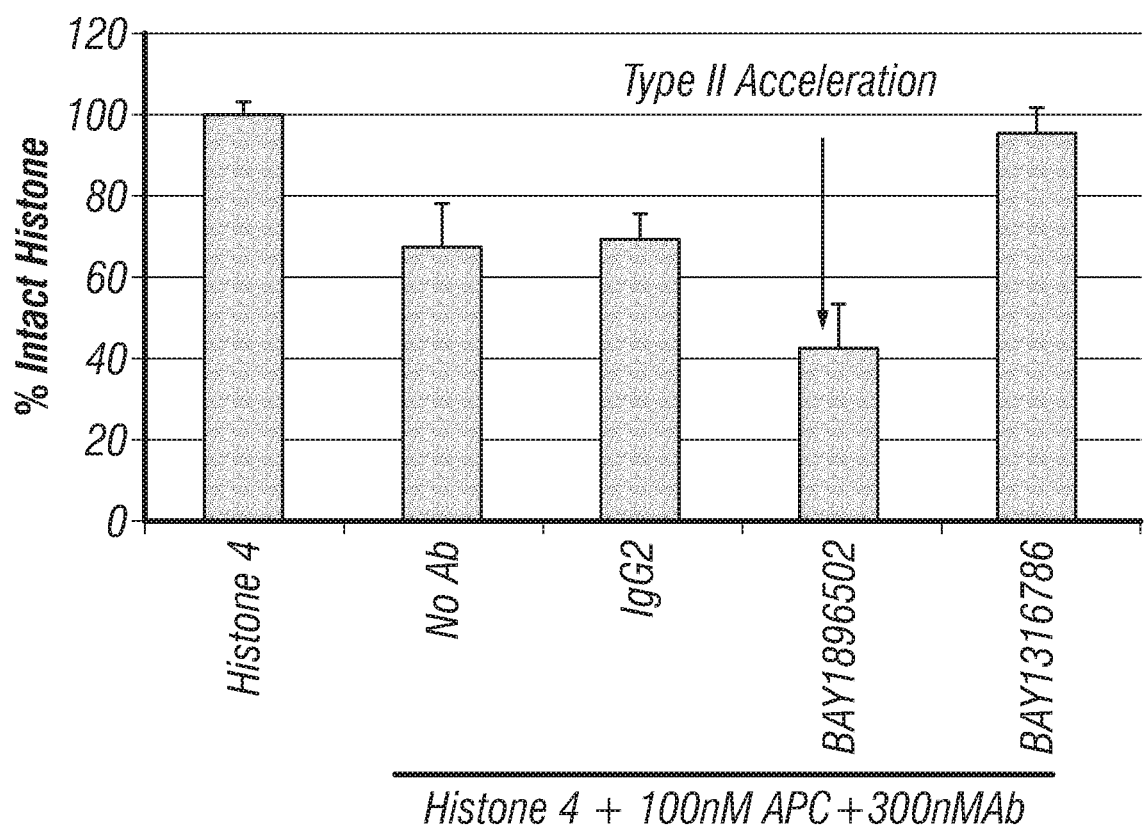
Figure 16:
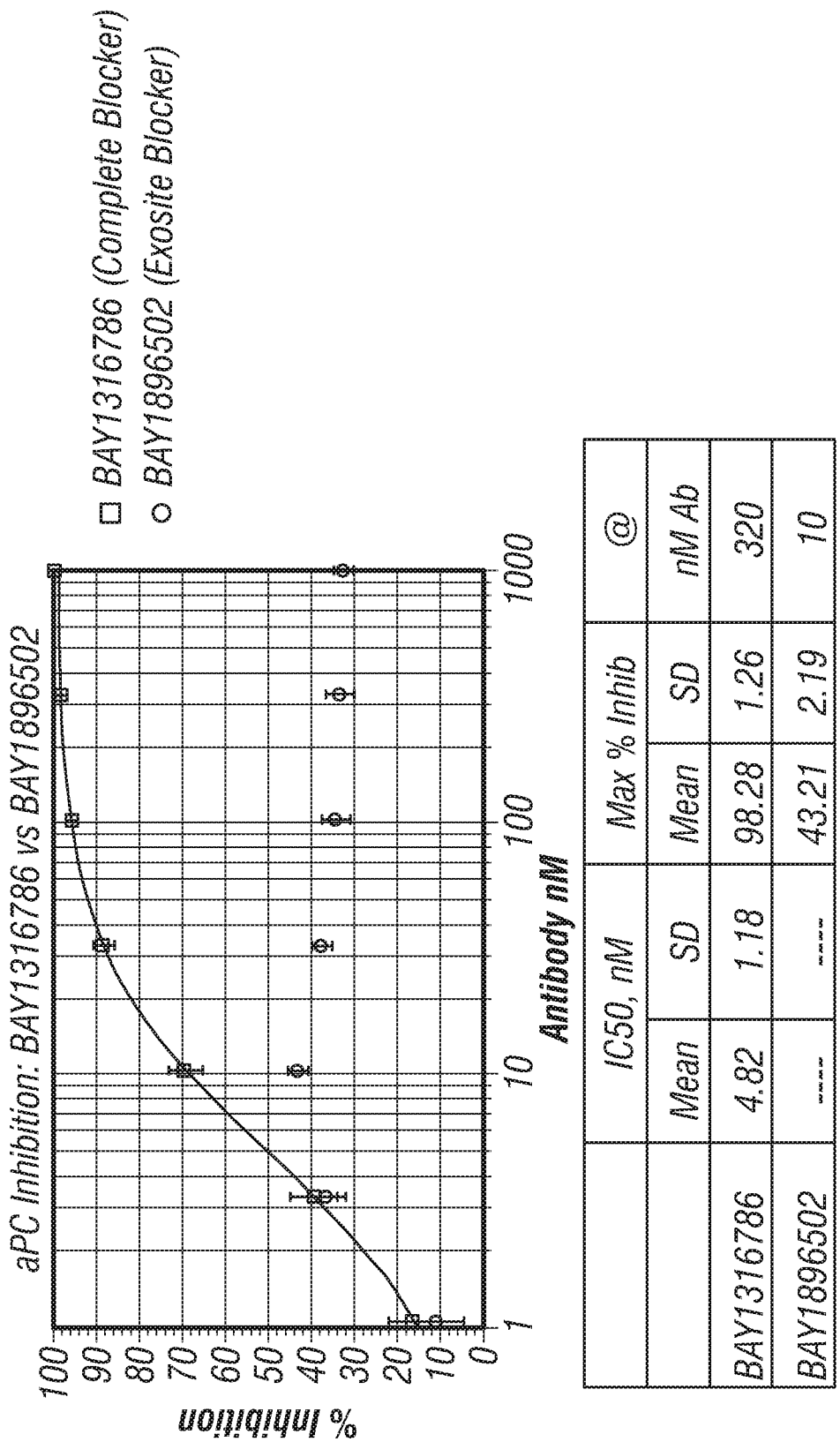

When FVIIIa was used as a substrate, type II abs completely protected FVIIIa from APC-dependent inactivation (FIGS. 13A-B). To assess the effect or type II abs on the cytoprotective functions of APC, histone 3 (FIGS. 14A-B) and histone 4 (FIGS. 15A-B) cleavage by APC were monitored in the presence and absence of type II abs. Type II abs accelerated both histone 3 and 4 cleavages by APC (FIGS. 14A-B).

In conclusion, these data suggest that type II abs can effectively protect the functional activities of FVa and FVIIIa from APC inactivation and might be effective in upregulating thrombin generation. Type II abs accelerate histone 3 and 4 cleavage by APC and therefore may augment the cytoprotective effects of APC. Our studies with various substrates suggest that type II antibodies bind to a site other than the active site of APC and are an allosteric modulator of APC activity.

Example 5—Anti-Activated Protein C (APC) Antibodies Block APC's Anti-Coagulant Function for Treatment of Hemophilia and Trauma-Induced Coagulopathy BAY1896502 binds to human aPC with high-affinity without binding to human PC similar to its precursor antibody, HAPC1573. Moreover, this antibody acts as a selective aPC function blocker by inhibiting the anti-coagulant activity of aPC while retaining aPC cytoprotective activity. It has a possible binding epitope at an exosite of APC that is involved in interaction with other protein factors like FVa or FVIIIa in the anti-coagulant process.

Figure 17:
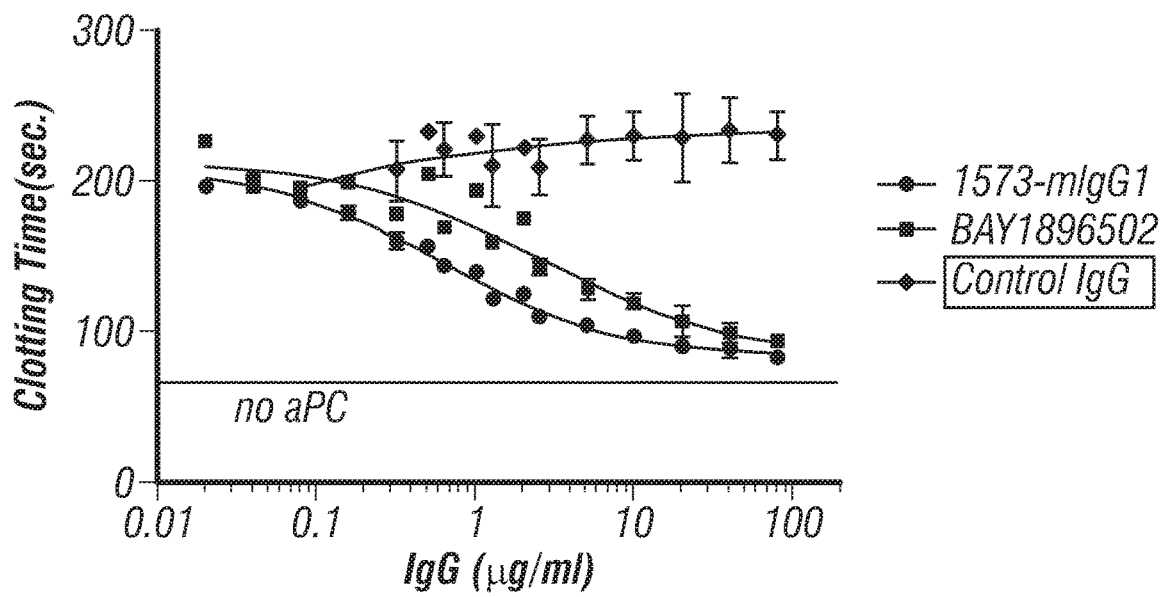
Figure 18:
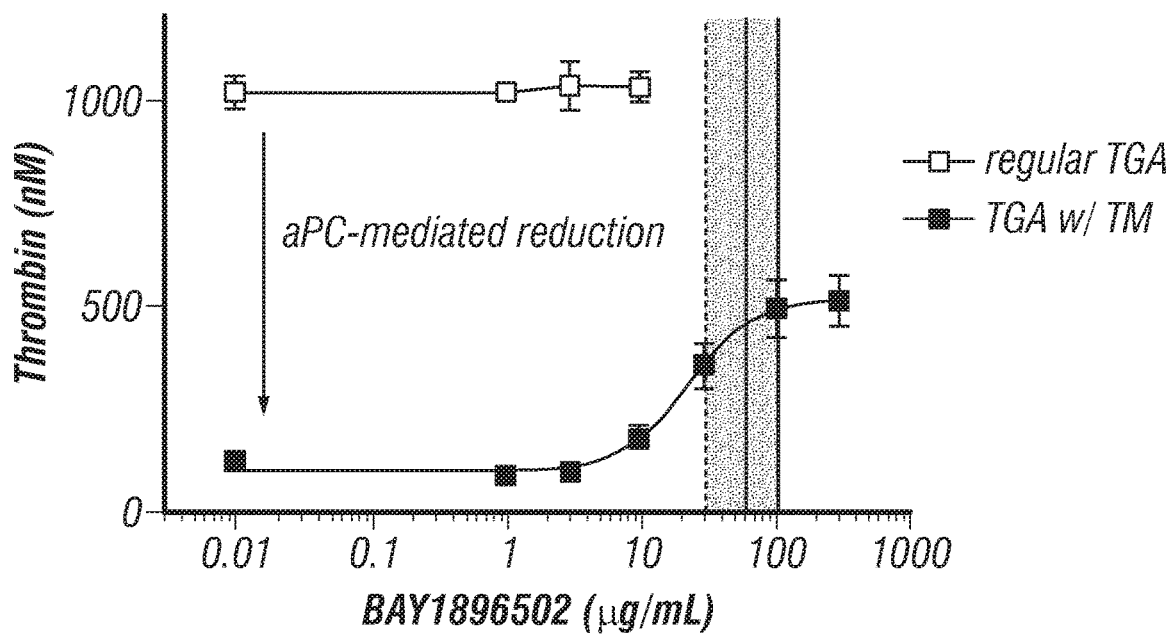
Figure 19:
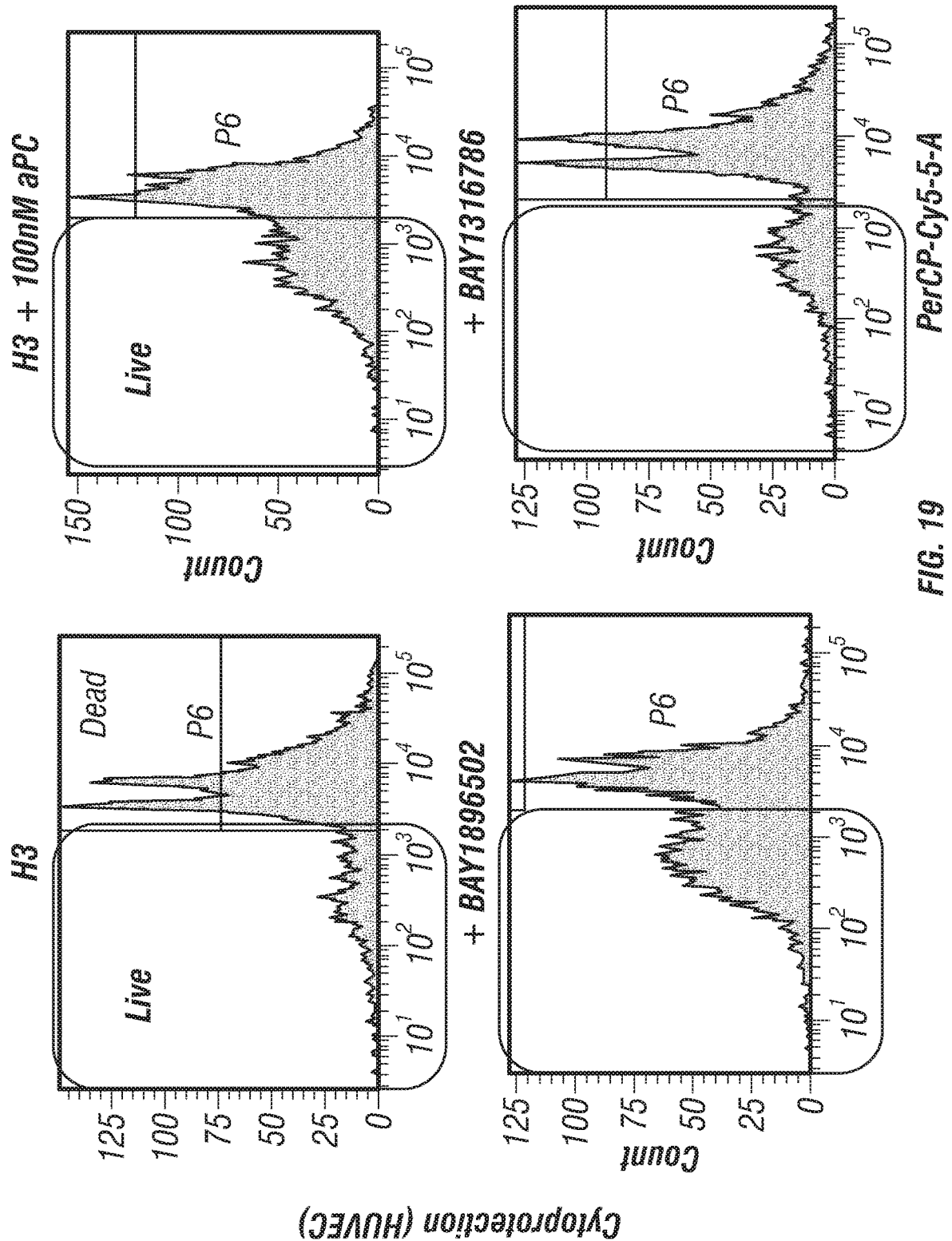

The antibody BAY1896502 was characterized in a number of functional assays. First, in FIG. 14, the influence of mAb on aPC activity was measured by chromogenic substrate-based assay or amidolytic activity assay. An exosite blocker, BAY1896502 blocks<50% of aPC activity in all concentrations tested. Next, FIG. 17 shows the influence of the same mAb on the anti-coagulant activity of aPC in a modified activated partial-thromboplastin time (aPTT assay). As shown, APC is a potent anticoagulant in aPTT assay and increased the clotting time (CT) of normal plasma from 60 second (no aPC) to 200 seconds. Anti-aPC mAbs blocked anticoagulant function of aPC and restored clotting time close to normal (~80 seconds) in dose-dependent manner. FIG. 18 shows the inhibitory effects of the anti-APC antibody on thrombin generation as determined in modified thrombin generation assay (TM-TGA) using human plasma. The added thrombomulin facilitated plasma PC activation to aPC, reducing total thrombin generation. Anti-aPC antibody BAY1896502 inhibited aPC and restored thrombin generation in dose dependent manner and promoted clot formation. Finally, FIG. 19 shows that BAY1896502 does not block aPC cytoprotective activity on human endothelium. aPC rapidly cleaves extracellular histones and rescues HUVECs from histone cytotoxicity (upper right panel) increasing number of live cells. BAY1896502 did not inhibit aPC cytoprotective activity and increased number of live cells further (lower left panel). However, active site blocking antibody (BAY1316786) blocked aPC cytoprotective activity and most of cells died due to histone cytotoxicity.

Example 6—X-Ray Crystallography Studies for Structural Epitope Mapping

Antibody information and details. Humanized antibody 1573 conserves the aPC-binding affinity and specificity but it has a number of issues e.g. high immunogenicity score, low expression titers in mammalian cells, reduced thermostability, etc. Germlining and framework-shuffling were used to optimize the antibody. The optimized germlined humanized antibody (TPP-4885) shows reduced immunogenicity scores, improved expression titers, and improved thermalstability while conserving aPC-binding affinity and specificity.

Epitope mapping using Hydrogen Deuterium Exchange has not been successful for this antibody. Here X-ray crystallography analysis was used to determine the binding epitopes of this antibody on aPC protein. Remarkably, the contacting epitopes were different from the active site of the aPC molecules.

An anti-activated Protein C-exosite antibody (humanized 1573 antibody) was germlined to reduce immunogenicity and optimized via framework-shuffling to improve antibody expression titers and antibody thermostability. The resulting humanized/germlined/optimized anti-APC exosite antibody TPP-4885 binds specifically to human APC at 14 nM (KD by Biacore) but not binds to human PC. Its Fab (TPP-5040) was used for structural epitope mapping by X-ray crystallography. X-ray structures at 3.7 angstrom revealed that the antibody contacting residues (binding epitope) comprises one or more residues selected from Y143, S145, S146, R147, E148, K149, E149-A, A149-B, S173, G186, R187, C191, E192, G216, E217, G218, C219, G220, L221, L222, H223, and N224 of human activated Protein C. Many contacting residues are located in the autolysis loop of APC (147-151 in CHT numbering). Data shows a ~13 Å movement of the His144-Thr152 loop (autolysis loop) of aPC between the PPACK binding APC and hu1573 binding APC states.

X-ray structures at 3.7 angstrom revealed that the antibody contacting residues (binding epitope) comprises one or more residues selected from Y143, S145, S146, R147, E148, K149, E149-A, A149-B, S173, G186, R187, C191, E192, G216, E217, G218, C219, G220, L221, L222, H223, and N224 of human activated Protein C (aPC). Many contacting residues are located in the autolysis loop of APC (147-151 in CHT numbering).

The optimized germlined anti-aPC antibodies TPP-3656/3657/3658/3639/TPP-4885 show improved expression titers in mammalian cells, improved thermal stability, and reduced immunogenicity scores while conserving aPC-binding affinity and specificity. They have passed antibody developability test for preclinical development as therapeutic antibody candidates.

Other Epitope Mapping methods such as H/DX have hitherto not been successful for this antibody. Epitope Mapping by X-ray crystallography revealed the contacting residues by this antibody on APC in the autolysis loop (a known FVa-binding loop). Results explain the mechanism of action of this antibody by competing against the cofactor FVa for APC-binding, thereby protecting FVa from APC inactivation to promote clotting.

Antibody Preparation and Quality Control.

Recombinant anti-aPC human Fabs (hu1573Fab) were expressed in mammalian cells and purified to homogeneity by using KappaSelect affinity chromatography followed by Superdex 200 size exclusion chromatography. Purified Fabs were showed to have a >90% purity and are lack of aggregation by SDS-PAGE and by analytical size exclusion chromatography. Their functions were characterized by aPC-binding assay (ELISA). Over 40 milligrams of these Fabs were produced from 4 L of media. They are intended for co-crystallography studies with aPC.

Antigen Preparation and Quality Control.

Plasma-derived human aPC-Gla-domain-less (aPC-GD) was purchased from Enzyme Research Lab and characterized by ELISA to confirm that it can be recognized by hu1573Fab.

Complex Formation.

For complex formation, 0.25 mg aPC-GD was mixed with 0.25 mg hu1573Fab and the reaction mixture was incubated over night at 4° C. The mixture was loaded onto a gel filtration column equilibrated with HBS buffer (10 mM HEPES, 150 mM NaCl, pH 7.2) to separate free Fab or free aPC from the aPC-hu1573Fab complex. Each fraction was collected and analyzed by SDS-PAGE under a non-reducing and reducing condition. This process was repeated two to four times, and the fractions containing the aPC-hu1573Fab complex were pooled and concentrated to 15 mg/ml. Crystallization of aPC-hu1573Fab complex under different crystal growth conditions was performed to produce crystals suitable for structure determination. The crystallization instrument Gryphon and 10 commercial high throughput crystallization screening kits were utilized and several hits were identified, the best pf which are (a) 0.2M sodium fluoride, 20% (w/v) PEG 3350; (b) 0.1M MES pH 6.0, 0.2M zinc acetate, 10% (w/v) PEG 8000; and (c) 0.1M cacodylate pH 6.5, 0.2M lithium sulfate, 30% (v/v) PEG 400. The best crystal was grown in sitting drop with 0.5 μl protein mixed with 0.5 μl well buffer at 18° C.

Data Collection and Structural Determination.

Diffraction data was collected at the BL17U beamline at the Shanghai Synchrotron Research Facility (SSRF). The images were processed with program HKL2000. The structure was determined at 3.7 Å resolution by the molecular replacement method with reported aPC (PDB code: 1 AUT) and other antibody Fab X-ray structures as models, and refined to a final $R_{work}$ of 0.278 and $R_{free}$ of 0.302. Shown in FIG. 20A is a cartoon representation of the aPC-hu1573Fab structure. Very significantly, as shown in FIG. 20B, the His144-Thr152 loop of aPC moved ~13 Å upon hu1573Fab binding in comparison with the aPC structure in PPACK (a previously reported tri-peptide inhibitor of aPC) binding state (PDB code: 1AUT). The binding of hu1573Fab to aPC does not have steric overlap with a PPACK (FIG. 20B).

From this structure, it was determined that the epitope of aPC bound by the antibody is in the heavy chain of aPC. Contacting residues of aPC include residues Y143, S145, S146, R147, E148, K149, E149-A, A149-B, S173, G186, R187, C191, E192, G216, E217, G218, C219, G220, L221, L222, H223, and N224.

For Fab hu1573, it was determined that the paratope comprises residues D30, S31, F32, G33, A34, F36, Y53, L54, S56, N57, N95, N96, E97, D98, and Y100 of the light chain shown in SEQ ID NOs: 5, 12, 19, 26, 33, 40, 47, 54, 61, 68, 78, and 81, and N31, Y32, Y33, R52, N56, E59, H60, E101, G102, D103, and Y104 of the heavy chain shown in SEQ ID NOs: 1, 11, 15, 25, 29, 39, 43, 53, 67, 71, and 77.

FIG. 20A shows x-ray structure of the aPC-hu1573Fab complex at 3.7 angstrom resolution that was refined to a final $R_{work}=0.278$, $R_{free}=0.302$. The left and right panels show the same complex structure with a rotation change of 90°.

Figure 20A:
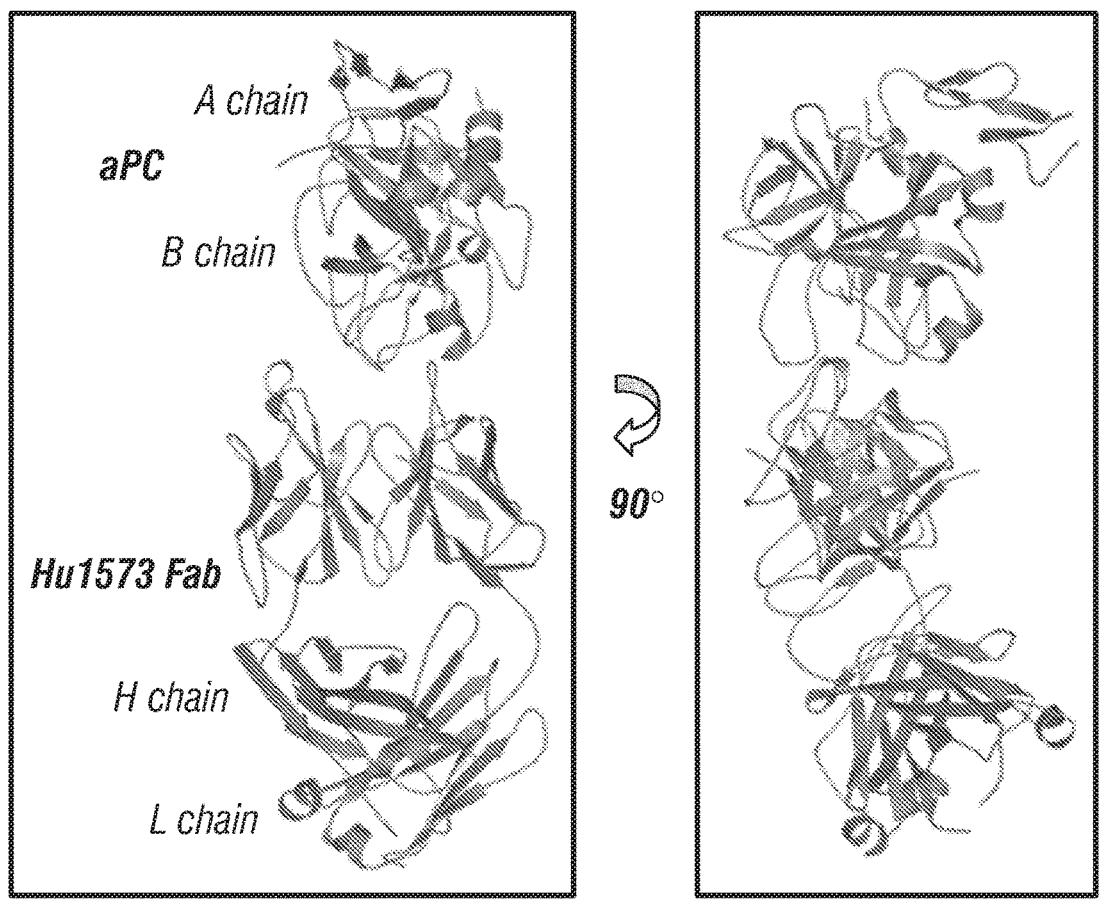
Figure 20B:
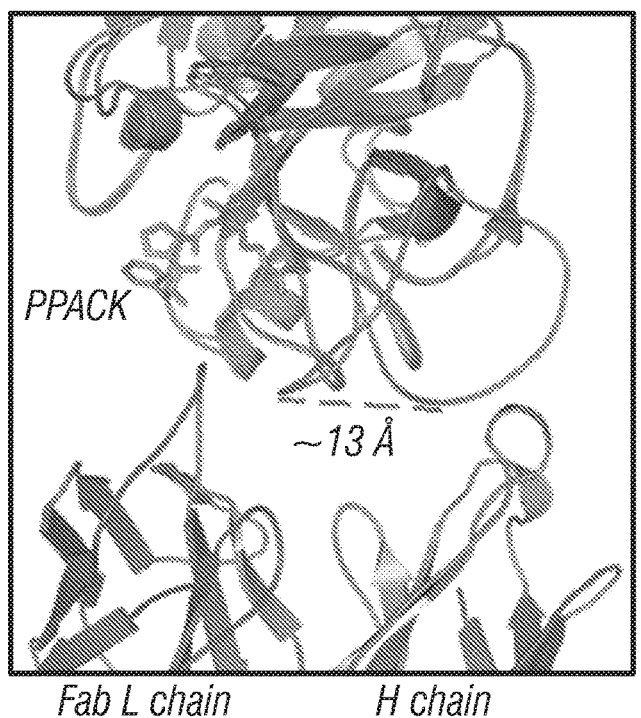

FIG. 20B shows a ~13 Å movement of the His144-Thr152 loop of aPC between the PPACK binding (dark gray) and hu1573 binding (light gray) states. Structural superimposition also shows that the hu1573Fab binding does not block the binding site of the previously reported PPACK on aPC.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,472,509
U.S. Pat. No. 4,938,948
U.S. Pat. No. 5,021,236
U.S. Pat. No. 5,141,648
U.S. Pat. No. 5,196,066
U.S. Pat. No. 5,563,250
U.S. Pat. No. 5,856,456
U.S. Pat. No. 5,880,270
U.S. Pat. No. 8,153,766
U.S. Patent Publication 2006/0122377
U.S. Patent Publication 2013/018440
PCT Publication WO2004/006955
Atherton et al., *Biol. Reprod.*, 32:155-171, 1985.
Berg et al., *Proc. Natl. Acad Sci. USA* 4, 100:4423-4428, 2003.
Bird et al., *Science*, 242:423-426, 1998.
Damschroder et al., *Mol. Immunol.*, 44:3049-3060, 2007.
De Jager et al., *Semin. Nucl. Med.*, 23:165-179, 1993.
Dholakia et al., 1989 *J. Biol. Chem.*, 264:20638-20642, 1989.
Doolittle and Ben-Zeev, *Methods Mol. Biol.*, 109:215-237, 1999.
Esmon, *J. Biol. Chem.*, 264:4743-4746, 1989.
Esmon, In: Handbook of Experimental Pharmacology. Uprichard and Gallagher (Eds.), Heidelberg: Springer-Verlag, vol. 132, pp. 447-476, 1999.
Gruber and Griffen, *Blood*, 79:2340-2348, 1992.
Gulbis and Galand. *Hum. Pathol.*, 24:1271-1285, 1993.
Guo et al., *Neuron*, 41:563-572, 2004.
Higgins et al., *Computer Applications in the Biosciences* (CABIOS), 8:189-191, 1992.
Huston et al., *Proc. Natl. Acad. Sci. USA*, 85:5879-5883, 1988.
Ill et al., *Protein Eng.*, 10:949-957, 1997.
Khatoon et al., *Ann. of Neurology*, 26:210-219, 1989.
King et al., *J. Biol. Chem.*, 269:10210-10218, 1989.
Liaw et al., *J. Thromb. Haemost.*, 1:662-670, 2003.
Manithody et al., *Blood*, 101:4802-4807, 2003.
Mosnier et al., *Blood*, 104:1740-1744, 2004.
Nakamura et al., In: Handbook of Experimental Immunology (4th Ed.), Weir et al. (Eds.), Blackwell Scientific Publ., Oxford, 1:27, 1987.
O'Shannessy et al., *J. Immun. Meth.*, 99:153-161, 1987.
Owens & Haley, *J. Biol. Chem.*, 259:14843-14848, 1987.
Potter & Haley, *Methods Enzymol.*, 91:613-633, 1983.
*Remington's Pharmaceutical Sciences*, 18th Ed., Mack Printing Company, pp. 1289-1329, 1990.
Tang et al., *J. Biol. Chem.*, 271:15682-15686, 1996.
Thompson et al., *Nucleic Acids Res.*, 2:4673-4680, 1994.
van't Zant et al., *Blood*, 90:3067-3072, 1997.
VBASE, MRC Centre of Protein Engineering, U K, 1997.
Ward et al., *Nature*, 341:544-546, 1989.
Wawrzynczak & Thorpe, In: Immunoconjugates: Antibody Conjugates in Radioimaging and Therapy of Cancer, Vogel (Ed.), New York: Oxford University Press, pp. 28-55, 1987.
Wu et al., *Proc. Natl. Acad. Sci. USA.*, 72:5107, 1975.
Wu and Kabat, *J. Exp. Med.*, 132:211, 1970.

The invention claimed is:

1. A human or humanized monoclonal antibody or human or humanized antibody fragment that is capable of specifically binding activated human protein C, but not unactivated human protein C, wherein said antibody or antibody fragment comprise a variable light chain of SEQ ID NO: 19 but with an N→D substitution at position 85 and a variable heavy chain of SEQ ID NO: 15.

2. The antibody or antibody fragment of claim 1, wherein the antibody is a diabody or minibody.

3. The antibody or antibody fragment of claim 1, wherein the antibody is germ-lined, affinity matured or framework shuffled antibody.

4. The antibody or antibody fragment of claim 1, wherein the antibody is a bispecific antibody or a chimeric antibody.

5. The antibody or antibody fragment of claim 1, wherein the antibody is a humanized or antibody.

6. The antibody or antibody fragment of claim 1, wherein said antibody is a single chain antibody.

7. The antibody or antibody fragment of claim 1, wherein said antibody fragment is an Fab'.

8. The antibody or antibody fragment of claim 1, wherein said antibody is capable of specifically binding an epitope in the autolysis lysis loop of the human activated protein C.

9. A pharmaceutical composition comprising an antibody or antibody fragment according to claim 1 and a pharmaceutically acceptable carrier or diluent.

10. A method of treating a subject in need of coagulation comprising administering to said subject an human or humanized antibody or human or humanized antibody fragment that is capable of specifically binding activated human protein C, but not unactivated human protein C, wherein said antibody or antibody fragment comprise a variable light chain of SEQ ID NO: 19 but with an N→D substitution at position 85 and a variable heavy chain of SEQ ID NO: 15.

11. The method of claim 10, wherein the antibody is a diabody or minibody.

12. The method of claim 10, wherein the antibody is a single chain antibody, a bispecific antibody or a chimeric antibody.

13. The method of claim 10, wherein the antibody is a humanized antibody.

14. The method of claim 10, wherein said antibody fragment is an Fab'.

15. The method of claim 10, wherein said antibody is capable of specifically binding an epitope in the autolysis lysis loop of the human activated protein C.

16. The method of claim 10, wherein said subject suffers from hemophilia or other bleeding diseases.

17. The method of claim 16, wherein the disease is including acute bleeding and/or bleeding associated with traumatic coagulopathy (endogenous acute coagulopathy EAC).

* * * * *

SEQUENCE LISTING

<160> NUMBER OF SEQ ID NOS: 84

<210> SEQ ID NO 1
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

```
Tyr Met Asn Trp Val Arg Gln Ala Pro Gly Lys Gly Leu Glu Trp Val
         35                  40                  45

Ala Asp Ile Arg Leu Lys Ser Asn Asn Tyr Glu Lys His Tyr Ala Asp
 50                  55                  60

Ser Val Lys Gly Arg Phe Thr Ile Ser Arg Asp Asn Ala Lys Asn Ser
 65                  70                  75                  80

Leu Tyr Leu Gln Met Asn Ser Leu Arg Ala Glu Asp Thr Ala Val Tyr
                 85                  90                  95

Tyr Cys Ala Arg Glu Gly Asp Tyr Phe Asp Tyr Trp Gly Gln Gly Thr
                100                 105                 110

Leu Val Thr Val Ser Ser
             115

<210> SEQ ID NO 2
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 2

Ser Tyr Tyr Met Asn
1               5

<210> SEQ ID NO 3
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 3

Asp Ile Arg Leu Lys Ser Asn Asn Tyr Glu Lys His Tyr Ala Asp Ser
1               5                   10                  15

Val Lys Gly

<210> SEQ ID NO 4
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 4

Ala Arg Glu Gly Asp Tyr Phe Asp Tyr
1               5

<210> SEQ ID NO 5
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 5

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Ser Phe
                20                  25                  30

Gly Ala Thr Phe Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
```

```
                    50                  55                  60
Arg Phe Ser Gly Ser Gly Ser Gly Thr Asp Phe Thr Leu Thr Ile Asn
 65                  70                  75                  80

Pro Val Glu Ala Asn Asp Thr Ala Asn Tyr Tyr Cys Gln Gln Asn Asn
                     85                  90                  95

Glu Asp Pro Tyr Thr Phe Gly Gln Gly Thr Lys Leu Glu Ile Lys
                100                 105                 110
```

<210> SEQ ID NO 6
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 6

```
Arg Ala Ser Glu Ser Val Asp Ser Phe Gly Ala Thr Phe Met His
 1               5                  10                  15
```

<210> SEQ ID NO 7
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 7

```
Leu Ala Ser Asn Leu Glu Ser
 1               5
```

<210> SEQ ID NO 8
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 8

```
Gln Gln Asn Asn Glu Asp Pro Tyr Thr
 1               5
```

<210> SEQ ID NO 9
<211> LENGTH: 354
<212> TYPE: DNA
<213> ORGANISM: Artificial Sequence
<220> FEATURE:
<223> OTHER INFORMATION: Synthetic nucleic acid

<400> SEQUENCE: 9

```
gaagtgcagc tggtggaatc cggcggaggc ctggtgcagc ctggcggatc tctgagactg    60
tcttgtgccg cctccggctt caccttctcc agctactaca tgaactgggt gcgacaggcc   120
cctggcaagg gcctggaatg gtggccgac atccggctga agtccaacaa ctacgagaag   180
cactacgccg actccgtgaa gggccggttc accatcagcc gggacaacgc caagaactcc   240
ctgtacctgc agatgaacag cctgcgggcc gaggacaccg ccgtgtacta ctgtgctaga   300
gagggcgact acttcgacta ctggggccag ggcacactcg tgaccgtcag ctca         354
```

<210> SEQ ID NO 10
<211> LENGTH: 333
<212> TYPE: DNA
<213> ORGANISM: Artificial Sequence
<220> FEATURE:
<223> OTHER INFORMATION: Synthetic nucleic acid

<400> SEQUENCE: 10

```
gatatcgtgc tgacccagtc tcctgcctcc ctggctgtgt ctcctggcca gagagccacc    60
atcacctgtc gggcctctga gtccgtggac tctttcggcg ccaccttcat gcactggtat   120
cagcagaagc ccggccagcc ccccaagctg ctgatctacc tggcctccaa cctggaatcc   180
ggcgtgcccg ccagattctc cggctctggc tctggcaccg acttcaccct gaccatcaac   240
cccgtggaag ccaacgacac cgccaactac tactgccagc agaacaacga ggaccccta c   300 accttcggcc agggcaccaa gctggaaatc aag                                 333
```

<210> SEQ ID NO 11
<211> LENGTH: 443
<212> TYPE: PRT
<213> ORGANISM: Artificial Sequence
<220> FEATURE:
<223> OTHER INFORMATION: Synthetic polypeptide

<400> SEQUENCE: 11

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Tyr Met Asn Trp Val Arg Gln Ala Pro Gly Lys Gly Leu Glu Trp Val
         35                  40                  45

Ala Asp Ile Arg Leu Lys Ser Asn Asn Tyr Glu Lys His Tyr Ala Asp
     50                  55                  60

Ser Val Lys Gly Arg Phe Thr Ile Ser Arg Asp Asn Ala Lys Asn Ser
 65                  70                  75                  80

Leu Tyr Leu Gln Met Asn Ser Leu Arg Ala Glu Asp Thr Ala Val Tyr
             85                  90                  95

Tyr Cys Ala Arg Glu Gly Asp Tyr Phe Asp Tyr Trp Gly Gln Gly Thr
        100                 105                 110

Leu Val Thr Val Ser Ser Ala Ser Thr Lys Gly Pro Ser Val Phe Pro
    115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285
```

Arg Glu Glu Gln Phe Asn Ser Thr Phe Arg Val Val Ser Val Leu Thr
290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
            325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
            405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
            435                 440

<210> SEQ ID NO 12
<211> LENGTH: 218
<212> TYPE: PRT
<213> ORGANISM: Artificial Sequence
<220> FEATURE:
<223> OTHER INFORMATION: Synthetic polypeptide

<400> SEQUENCE: 12

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Ser Phe
            20                  25                  30

Gly Ala Thr Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln Gln Asn Asn
                85                  90                  95

Glu Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 13
<211> LENGTH: 1329
<212> TYPE: DNA
<213> ORGANISM: Artificial Sequence
<220> FEATURE:
<223> OTHER INFORMATION: Synthetic nucleic acid

<400> SEQUENCE: 13

| | |
|---|---|
| gaagtgcagc tggtggaatc cggcggaggc ctggtgcagc ctggcggatc tctgagactg | 60 |
| tcttgtgccg cctccggctt caccttctcc agctactaca tgaactgggt gcgacaggcc | 120 |
| cctggcaagg gcctggaatg ggtggccgac atccggctga agtccaacaa ctacgagaag | 180 |
| cactacgccg actccgtgaa gggccggttc accatcagcc gggacaacgc caagaactcc | 240 |
| ctgtacctgc agatgaacag cctgcgggcc gaggacaccg ccgtgtacta ctgtgctaga | 300 |
| gagggcgact acttcgacta ctggggccag ggcacactcg tgaccgtcag ctcagcttcc | 360 |
| accaagggcc cctccgtgtt ccctctggcc ccttgctccc ggtccacctc tgagtctacc | 420 |
| gccgctctgg gctgcctggt gaaagactac ttccccgagc ccgtgaccgt gtcctggaac | 480 |
| tctggcgccc tgacctccgg cgtgcacacc tttccagccg tgctgcagtc ctccggcctg | 540 |
| tactccctgt cctccgtggt gacagtgccc tcctccaact tcggcaccca gacctacacc | 600 |
| tgtaacgtgg accacaagcc ctccaacacc aaggtggaca gaccgtgga acggaagtgc | 660 |
| tgcgtggaat gccaccctg tcctgctcca cctgtggctg gccccagcgt gttcctgttc | 720 |
| cccccaaagc ccaaggacac cctgatgatc tcccggaccc ccgaagtgac ctgcgtggtg | 780 |
| gtggacgtgt cccacgagga ccccgaggtg cagttcaatt ggtacgtgga cggcgtggaa | 840 |
| gtgcacaacg ccaagaccaa gcccagagag gaacagttca actccacctt ccgggtggtg | 900 |
| tccgtgctga ccgtggtgca tcaggactgg ctgaacggca agagtacaa gtgcaaggtc | 960 |
| tccaacaagg cctgcctgc ccccatcgaa aagaccatca gcaagaccaa gggccagccc | 1020 |
| cgcgagcccc aggtgtacac actgcccccc agccgggaag atgaccaa gaaccaggtg | 1080 |
| tccctgacct gtctggtgaa aggcttctac ccctccgaca ttgccgtgga atgggagtcc | 1140 |
| aacggacagc ctgagaacaa ctacaagacc ccccccccca tgctggactc cgacggctca | 1200 |
| ttcttcctgt actccaagct gacagtggac aagtcccgt ggcagcaggg caacgtgttc | 1260 |
| tcctgctccg tgatgcacga ggccctgcac aaccactaca cccagaagtc cctgtccctg | 1320 |
| agccccggc | 1329 |

<210> SEQ ID NO 14
<211> LENGTH: 654
<212> TYPE: DNA
<213> ORGANISM: Artificial Sequence
<220> FEATURE:
<223> OTHER INFORMATION: Synthetic nucleic acid

<400> SEQUENCE: 14

| | |
|---|---|
| gatatcgtgc tgacccagtc tcctgcctcc ctggctgtgt cctggccca gagagccacc | 60 |
| atcacctgtc gggcctctga gtccgtggac tctttcggcg ccaccttcat gcactggtat | 120 |
| cagcagaagc ccggccagcc ccccaagctg ctgatctacc tggcctccaa cctggaatcc | 180 |
| ggcgtgcccg ccagattctc cggctctggc tctggcaccg acttcaccct gaccatcaac | 240 |
| cccgtggaag ccaacgacac cgccaactac tactgccagc agaacaacga ggacccctac | 300 |

```
accttcggcc agggcaccaa gctggaaatc aagcggaccg tggccgctcc ctccgtgttt       360
atcttcccac cctccgacga gcagctgaag tccggcacag cttccgtcgt gtgcctgctg       420
aacaacttct accctcggga agccaaggtg cagtggaagg tggacaacgc cctgcagtcc       480
ggcaactccc aggaatccgt gaccgagcag gactccaagg acagcaccta ctccctgtcc       540
tctaccctga cccgtgtcaa ggccgactac gagaagcaca aggtgtacgc ctgcgaagtg       600
acccaccagg gcctgtctag ccccgtgacc aagtctttca accggggcga gtgt             654
```

```
<210> SEQ ID NO 15
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Leu Asn Trp Val Arg Gln Ala Pro Gly Lys Gly Leu Glu Trp Val
        35                  40                  45

Gly Asp Ile Arg Leu Lys Ser Asn Asn Tyr Glu Lys His Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Asp Thr Ala Val Tyr
                85                  90                  95

Tyr Cys Ala Arg Glu Gly Asp Tyr Phe Asp Tyr Trp Gly Gln Gly Thr
            100                 105                 110

Leu Val Thr Val Ser Ser
        115
```

```
<210> SEQ ID NO 16
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 16

Asn Tyr Tyr Leu Asn
1               5
```

```
<210> SEQ ID NO 17
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 17

Asp Ile Arg Leu Lys Ser Asn Asn Tyr Glu Lys His Tyr Ala Glu Ser
1               5                   10                  15

Val Lys Gly
```

```
<210> SEQ ID NO 18
<211> LENGTH: 9
<212> TYPE: PRT
<213> ORGANISM: Artificial Sequence
```

<220> FEATURE:
<223> OTHER INFORMATION: Synthetic polypeptide

<400> SEQUENCE: 18

Ala Arg Glu Gly Asp Tyr Phe Asp Tyr
1               5

<210> SEQ ID NO 19
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 19

Asp Ile Val Leu Thr Gln Ser Pro Ala Ser Leu Ala Val Ser Pro Gly
1               5                   10                  15

Gln Arg Ala Thr Ile Thr Cys Lys Ala Ser Glu Ser Val Asp Ser Phe
            20                  25                  30

Gly Ala Thr Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln Gln Asn Asn
                85                  90                  95

Glu Asp Pro Tyr Thr Phe Gly Gln Gly Thr Lys Leu Glu Ile Lys
            100                 105                 110

<210> SEQ ID NO 20
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 20

Lys Ala Ser Glu Ser Val Asp Ser Phe Gly Ala Thr Phe Met His
1               5                   10                  15

<210> SEQ ID NO 21
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 21

Leu Ala Ser Asn Leu Glu Ser
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 22

Gln Gln Asn Asn Glu Asp Pro Tyr Thr
1               5

<210> SEQ ID NO 23
<211> LENGTH: 354
<212> TYPE: DNA
<213> ORGANISM: Artificial Sequence
<220> FEATURE:
<223> OTHER INFORMATION: Synthetic nucleic acid

<400> SEQUENCE: 23

```
gaagtgcagc tggtggaatc cggcggaggc ctggtgcagc ctggcggatc tctgagactg      60
tcttgtgccg cctccggctt caccttctcc aactactacc tgaactgggt gcgacaggcc     120
cctggcaagg gactggaatg ggtgggagac atccggctga gtccaacaa ctacgagaag      180
cactacgccg agtccgtgaa gggccggttc accatctctc gggacgactc caagaactcc     240
ctgtacctgc agatgaacag cctgaaaacc gaggacaccg ccgtgtacta ctgcgccaga     300
gagggcgact acttcgacta ctggggccag ggcacactcg tgaccgtcag ctca           354
```

<210> SEQ ID NO 24
<211> LENGTH: 333
<212> TYPE: DNA
<213> ORGANISM: Artificial Sequence
<220> FEATURE:
<223> OTHER INFORMATION: Synthetic nucleic acid

<400> SEQUENCE: 24

```
gatatcgtgc tgacccagtc tcctgcctcc ctggctgtgt ctcctggcca gagagccacc      60
attacctgca aggcctccga gtccgtggac tccttcggcg ccaccttcat gcactggtat     120
cagcagaagc ccggccagcc ccccaagctg ctgatctacc tggcctccaa cctggaatcc     180
ggcgtgcccg ccagattctc cggctctggc tctggcaccg acttcaccct gaccatcaac     240
cccgtggaag ccaacgacac cgccaactac tactgccagc agaacaacga ggaccccctac    300
accttcggcc agggcaccaa gctggaaatc aag                                  333
```

<210> SEQ ID NO 25
<211> LENGTH: 443
<212> TYPE: PRT
<213> ORGANISM: Artificial Sequence
<220> FEATURE:
<223> OTHER INFORMATION: Synthetic polypeptide

<400> SEQUENCE: 25

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Leu Asn Trp Val Arg Gln Ala Pro Gly Lys Gly Leu Glu Trp Val
        35                  40                  45

Gly Asp Ile Arg Leu Ser Asn Asn Tyr Glu Lys His Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Glu Gly Asp Tyr Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140
```

```
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
            195                 200                 205

Asn Thr Lys Val Asp Lys Thr Val Glu Arg Lys Cys Cys Val Glu Cys
210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Phe Arg Val Val Ser Val Leu Thr
290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
            325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
            405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
            435                 440

<210> SEQ ID NO 26
<211> LENGTH: 218
<212> TYPE: PRT
<213> ORGANISM: Artificial Sequence
<220> FEATURE:
<223> OTHER INFORMATION: Synthetic polypeptide

<400> SEQUENCE: 26

Asp Ile Val Leu Thr Gln Ser Pro Ala Ser Leu Ala Val Ser Pro Gly
1               5                   10                  15

Gln Arg Ala Thr Ile Thr Cys Lys Ala Ser Glu Ser Val Asp Ser Phe
            20                  25                  30

Gly Ala Thr Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
50                  55                  60
```

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln Gln Asn Asn
            85                  90                  95

Glu Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
210                 215

<210> SEQ ID NO 27
<211> LENGTH: 1329
<212> TYPE: DNA
<213> ORGANISM: Artificial Sequence
<220> FEATURE:
<223> OTHER INFORMATION: Synthetic nucleic acid

<400> SEQUENCE: 27
gaagtgcagc tggtggaatc cggcggaggc ctggtgcagc ctggcggatc tctgagactg      60
tcttgtgccg cctccggctt caccttctcc aactactacc tgaactgggt gcgacaggcc     120
cctggcaagg gactggaatg ggtgggagac atccggctga gtccaacaa ctacgagaag      180 cactacgccg agtccgtgaa gggccggttc accatctctc gggacgactc caagaactcc     240
ctgtacctgc agatgaacag cctgaaaacc gaggacaccg ccgtgtacta ctgcgccaga     300
gagggcgact acttcgacta ctggggccag ggcacactcg tgaccgtcag ctcagcttcc     360
accaagggcc cctccgtgtt ccctctggcc ccttgctccc ggtccacctc tgagtctacc     420
gccgctctgg gctgcctggt gaaagactac ttccccgagc ccgtgaccgt gcctggaac      480 tctggcgccc tgacctccgg cgtgcacacc tttccagccg tgctgcagtc ctccggcctg     540
tactccctgt cctccgtggt gacagtgccc tcctccaact tcggcaccca gacctacacc     600
tgtaacgtgg accacaagcc ctccaacacc aaggtggaca gaccgtgga cggaagtgc      660 tgcgtggaat gcccacccty tcctgctcca cctgtggctg gccccagcgt gttcctgttc     720
cccccaaagc ccaaggacac cctgatgatc tcccggaccc ccgaagtgac ctgcgtggtg     780
gtggacgtgt cccacgagga ccccgaggtg cagttcaatt ggtacgtgga cggcgtggaa     840
gtgcacaacg ccaagaccaa gcccagagag gaacagttca ctccaccctt ccgggtggtg     900
tccgtgctga ccgtggtgca tcaggactgg ctgaacggca agagtacaa gtgcaaggtc     960 tccaacaagg gcctgcctgc ccccatcgaa aagaccatca gcaagaccaa gggccagccc    1020
cgcgagcccc aggtgtacac actgcccccc agcegggaag atgaccaa gaaccaggtg     1080 tccctgacct gtctggtgaa aggcttctac ccctccgaca ttgccgtgga atgggagtcc    1140

```
aacggacagc ctgagaacaa ctacaagacc accccccccca tgctggactc cgacggctca    1200
ttcttcctgt actccaagct gacagtggac aagtcccggt ggcagcaggg caacgtgttc    1260
tcctgctccg tgatgcacga ggccctgcac aaccactaca cccagaagtc cctgtccctg    1320
agccccggc                                                            1329
```

<210> SEQ ID NO 28
<211> LENGTH: 654
<212> TYPE: DNA
<213> ORGANISM: Artificial Sequence
<220> FEATURE:
<223> OTHER INFORMATION: Synthetic nucleic acid

<400> SEQUENCE: 28

```
gatatcgtgc tgacccagtc tcctgcctcc ctggctgtgt ctcctggcca gagagccacc      60
attacctgca aggcctccga gtccgtggac tccttcggcg ccaccttcat gcactggtat     120
cagcagaagc ccggccagcc ccccaagctg ctgatctacc tggcctccaa cctggaatcc     180
ggcgtgcccg ccagattctc cggctctggc tctggcaccg acttcaccct gaccatcaac     240
cccgtggaag ccaacgacac cgccaactac tactgccagc agaacaacga ggacccctac     300
accttcggcc agggcaccaa gctggaaatc aagcggaccg tggccgctcc ctccgtgttt     360
atcttcccac cctccgacga gcagctgaag tccggcacag cttccgtcgt gtgcctgctg     420
aacaacttct accctcggga agccaaggtg cagtggaagg tggacaacgc cctgcagtcc     480
ggcaactccc aggaatccgt gaccgagcag gactccaagg acagcaccta ctccctgtcc     540
tctaccctga ccctgtccaa ggccgactac gagaagcaca aggtgtacgc ctgcgaagtg     600
acccaccagg gcctgtctag ccccgtgacc aagtctttca ccggggcga gtgt            654
```

<210> SEQ ID NO 29
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 29

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Leu Asn Trp Val Arg Gln Ala Pro Gly Lys Gly Leu Glu Trp Val
        35                  40                  45

Ala Asp Ile Lys Ser Asn Asn Tyr Glu Lys His Tyr Ala Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Asp Tyr Phe Asp Tyr Trp Gly Gln Gly Thr Leu Val
            100                 105                 110

Thr Val Ser Ser
        115
```

<210> SEQ ID NO 30
<211> LENGTH: 5
<212> TYPE: PRT
<213> ORGANISM: Artificial Sequence

```
<220> FEATURE:
<223> OTHER INFORMATION: Synthetic polypeptide

<400> SEQUENCE: 30

Asn Tyr Tyr Leu Asn
1               5

<210> SEQ ID NO 31
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 31

Asp Ile Lys Ser Asn Asn Tyr Glu Lys His Tyr Ala Glu Ser Val Lys
1               5                   10                  15

Gly

<210> SEQ ID NO 32
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 32

Ala Arg Glu Gly Asp Tyr Phe Asp Tyr
1               5

<210> SEQ ID NO 33
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 33

Asp Ile Val Leu Thr Gln Ser Pro Ala Ser Leu Ala Val Ser Pro Gly
1               5                   10                  15

Gln Arg Ala Thr Ile Thr Cys Lys Ala Ser Gln Ser Val Asp Ser Phe
            20                  25                  30

Gly Ala Thr Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln Gln Asn Asn
                85                  90                  95

Glu Asp Pro Tyr Thr Phe Gly Gln Gly Thr Lys Leu Glu Ile Lys
            100                 105                 110

<210> SEQ ID NO 34
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 34

Lys Ala Ser Glu Ser Val Asp Ser Phe Gly Ala Thr Phe Met His
1               5                   10                  15
```

<210> SEQ ID NO 35
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 35

Leu Ala Ser Asn Leu Glu Ser
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 36

Gln Gln Asn Asn Glu Asp Pro Tyr Thr
1               5

<210> SEQ ID NO 37
<211> LENGTH: 348
<212> TYPE: DNA
<213> ORGANISM: Artificial Sequence
<220> FEATURE:
<223> OTHER INFORMATION: Synthetic nucleic acid

<400> SEQUENCE: 37
gaagtgcagc tggtggaatc cggcggaggc ctggtgcagc tggcggatc tctgagactg      60 tcttgtgccg cctccggctt caccttctcc aactactacc tgaactgggt gcgacaggcc    120
cctggcaagg gactggaatg ggtggccgac atcaagtcca caactacga aagcactac     180 gccgagtccg tgaagggccg gttcaccatc agccgggaca cgccaagaa ctccctgtac    240 ctgcagatga acagcctgcg ggccgaggac accgccgtgt actactgtgc tagagagggc    300
gactacttcg actactgggg ccagggcaca ctcgtgaccg tcagctca                 348

<210> SEQ ID NO 38
<211> LENGTH: 333
<212> TYPE: DNA
<213> ORGANISM: Artificial Sequence
<220> FEATURE:
<223> OTHER INFORMATION: Synthetic nucleic acid

<400> SEQUENCE: 38
gatatcgtgc tgacccagtc tcctgcctcc ctggctgtgt ctcctggcca gagagccacc     60
attacctgca aggcctccga gtccgtggac tccttcggcg ccaccttcat gcactggtat    120
cagcagaagc ccggccagcc ccccaagctg ctgatctacc tggcctccaa cctggaatcc    180
ggcgtgcccg ccagattctc cggctctggc tctggcaccg acttcaccct gaccatcaac    240
cccgtggaag ccaacgacac cgccaactac tactgccagc agaacaacga ggacccctac    300
accttcggcc agggcaccaa gctggaaatc aag                                 333

<210> SEQ ID NO 39
<211> LENGTH: 441
<212> TYPE: PRT
<213> ORGANISM: Artificial Sequence
<220> FEATURE:
<223> OTHER INFORMATION: Synthetic polypeptide

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Leu Asn Trp Val Arg Gln Ala Pro Gly Lys Gly Leu Glu Trp Val
        35                  40                  45

Ala Asp Ile Lys Ser Asn Asn Tyr Glu Lys His Tyr Ala Glu Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Asp Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
        195                 200                 205

Lys Val Asp Lys Thr Val Glu Arg Lys Cys Cys Val Glu Cys Pro Pro
210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Phe Arg Val Val Ser Val Leu Thr Val Val
290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
370                 375                 380

Asn Tyr Lys Thr Thr Pro Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

```
Val Phe Ser Cys Ser Val Met His Glu Ala Leu His Asn His Tyr Thr
            420                 425                 430
Gln Lys Ser Leu Ser Leu Ser Pro Gly
        435                 440
```

<210> SEQ ID NO 40
<211> LENGTH: 218
<212> TYPE: PRT
<213> ORGANISM: Artificial Sequence
<220> FEATURE:
<223> OTHER INFORMATION: Synthetic polypeptide

<400> SEQUENCE: 40

```
Asp Ile Val Leu Thr Gln Ser Pro Ala Ser Leu Ala Val Ser Pro Gly
1               5                   10                  15
Gln Arg Ala Thr Ile Thr Cys Lys Ala Ser Glu Ser Val Asp Ser Phe
            20                  25                  30
Gly Ala Thr Phe Met His Trp Tyr Gln Gln Lys Pro Gly Gln Pro Pro
        35                  40                  45
Lys Leu Leu Ile Tyr Leu Ala Ser Asn Leu Glu Ser Gly Val Pro Ala
    50                  55                  60
Arg Phe Ser Gly Ser Gly Ser Gly Thr Asp Phe Thr Leu Thr Ile Asn
65                  70                  75                  80
Pro Val Glu Ala Asn Asp Thr Ala Asn Tyr Tyr Cys Gln Gln Asn Asn
                85                  90                  95
Glu Asp Pro Tyr Thr Phe Gly Gln Gly Thr Lys Leu Glu Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215
```

<210> SEQ ID NO 41
<211> LENGTH: 1323
<212> TYPE: DNA
<213> ORGANISM: Artificial Sequence
<220> FEATURE:
<223> OTHER INFORMATION: Synthetic nucleic acid

<400> SEQUENCE: 41

```
gaagtgcagc tggtggaatc cggcggaggc ctggtgcagc ctggcggatc tctgagactg      60
tcttgtgccg cctccggctt caccttctcc aactactacc tgaactgggt gcgacaggcc     120
cctggcaagg gactggaatg ggtggccgac atcaagtcca caactacga gaagcactac      180
gccgagtccg tgaagggccg gttcaccatc agcggggaca cgccaagaa ctccctgtac      240
ctgcagatga acagcctgcg ggccgaggac accgccgtgt actactgtgc tagagagggc     300
```

```
gactacttcg actactgggg ccagggcaca ctcgtgaccg tcagctcagc ttccaccaag    360 ggccctccg tgttccctct ggccccttgc tcccggtcca cctctgagtc taccgccgct     420
ctgggctgcc tggtgaaaga ctacttcccc gagcccgtga ccgtgtcctg aactctggc    480 gccctgacct ccggcgtgca cacctttcca gccgtgctgc agtcctccgg cctgtactcc    540
ctgtcctccg tggtgacagt gccctcctcc aacttcggca cccagaccta cacctgtaac    600
gtggaccaca gccctccaa caccaaggtg gacaagaccg tggaacggaa gtgctgcgtg     660
gaatgcccac cctgtcctgc tccacctgtg gctggcccca gcgtgttcct gttcccccca    720
aagcccaagg acaccctgat gatctcccgg acccccgaag tgacctgcgt ggtggtggac    780
gtgtcccacg aggaccccga ggtgcagttc aattggtacg tggacggcgt ggaagtgcac    840
aacgccaaga ccaagcccag agaggaacag ttcaactcca ccttccgggt ggtgtccgtg    900
ctgaccgtgg tgcatcagga ctggctgaac ggcaaagagt acaagtgcaa ggtctccaac    960
aagggcctgc ctgcccccat cgaaaagacc atcagcaaga ccaagggcca gccccgcgag    1020
ccccaggtgt acacactgcc ccccagccgg gaagagatga ccaagaacca ggtgtccctg    1080
acctgtctgg tgaaaggctt ctacccctcc gacattgccg tggaatggga gtccaacgga    1140
cagcctgaga caactacaa gaccaccccc cccatgctgg actccgacgg ctcattcttc     1200
ctgtactcca agctgacagt ggacaagtcc cggtggcagc agggcaacgt gttctcctgc    1260
tccgtgatgc acgaggccct gcacaaccac tacacccaga gtccctgtc cctgagcccc    1320 ggc                                                                 1323

<210> SEQ ID NO 42
<211> LENGTH: 654
<212> TYPE: DNA
<213> ORGANISM: Artificial Sequence
<220> FEATURE:
<223> OTHER INFORMATION: Synthetic nucleic acid

<400> SEQUENCE: 42
gatatcgtgc tgacccagtc tcctgcctcc ctggctgtgt ctcctggcca gagagccacc     60
attacctgca aggcctccga gtccgtggac tccttcggcg ccaccttcat gcactggtat    120
cagcagaagc ccggccagcc ccccaagctg ctgatctacc tggcctccaa cctggaatcc    180
ggcgtgcccg ccagattctc cggctctggc tctggcaccg acttcaccct gaccatcaac    240
cccgtggaag ccaacgacac cgccaactac tactgccagc agaacaacga ggacccctac    300
accttcggcc agggcaccaa gctggaaatc aagcggaccg tggccgctcc ctccgtgttt    360
atcttcccac cctccgacga gcagctgaag tccggcacag cttccgtcgt gtgcctgctg    420
aacaacttct accctcggga agccaaggtg cagtggaagg tggacaacgc cctgcagtcc    480
ggcaactccc aggaatccgt gaccgagcag gactccaagg acagcaccta ctccctgtcc    540 tctacccctga ccctgtccaa ggccgactac gagaagcaca aggtgtacgc ctgcgaagtg    600
acccaccagg gcctgtctag ccccgtgacc aagtctttca ccggggcga gtgt           654

<210> SEQ ID NO 43
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 43

Glu Val Gln Leu Val Glu Ser Gly Gly Gly Leu Val Gln Pro Gly Gly
```

-continued

```
                1               5                  10                  15
Ser Leu Arg Leu Ser Cys Ala Ala Ser Gly Phe Thr Phe Ser Asn Tyr
                    20                  25                  30

Tyr Leu Asn Trp Val Arg Gln Ala Pro Gly Lys Gly Leu Glu Trp Val
            35                  40                  45

Ala Asp Ile Arg Leu Lys Ser Asn Asn Tyr Glu Lys His Tyr Ala Glu
        50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ile Arg Glu Gly Asp Tyr Phe Asp Tyr Trp Gly Gln Gly Thr
            100                 105                 110

Thr Val Thr Val Ser Ser
        115
```

<210> SEQ ID NO 44
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 44

```
Asn Tyr Tyr Leu Asn
1               5
```

<210> SEQ ID NO 45
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 45

```
Asp Ile Arg Leu Lys Ser Asn Asn Tyr Glu Lys His Tyr Ala Glu Ser
1               5                   10                  15

Val Lys Gly
```

<210> SEQ ID NO 46
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 46

```
Ile Arg Glu Gly Asp Tyr Phe Asp Tyr
1               5
```

<210> SEQ ID NO 47
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 47

```
Asp Ile Val Leu Thr Gln Ser Pro Ala Ser Leu Ala Val Ser Pro Gly
1               5                   10                  15

Gln Arg Ala Thr Ile Thr Cys Lys Ala Ser Glu Ser Val Asp Ser Phe
            20                  25                  30
```

Gly Ala Thr Phe Met His Trp Tyr Gln Gln Lys Pro Gly Gln Pro
            35                  40                  45

Lys Leu Leu Ile Tyr Leu Ala Ser Asn Leu Glu Ser Gly Val Pro Ala
        50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln Gln Asn Asn
                85                  90                  95

Glu Asp Pro Tyr Thr Phe Gly Gln Gly Thr Lys Leu Glu Ile Lys
            100                 105                 110

<210> SEQ ID NO 48
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 48

Lys Ala Ser Glu Ser Val Asp Ser Phe Gly Ala Thr Phe Met His
1               5                   10                  15

<210> SEQ ID NO 49
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 49

Leu Ala Ser Asn Leu Glu Ser
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 50

Gln Gln Asn Asn Glu Asp Pro Tyr Thr
1               5

<210> SEQ ID NO 51
<211> LENGTH: 354
<212> TYPE: DNA
<213> ORGANISM: Artificial Sequence
<220> FEATURE:
<223> OTHER INFORMATION: Synthetic nucleic acid

<400> SEQUENCE: 51
gaagtgcagc tggtggaatc cggcggaggc ctggtgcagc ctggcggatc tctgagactg      60
tcttgtgccg cctccggctt caccttctcc aactactacc tgaactgggt gcgacaggcc     120
cctggcaagg gactggaatg ggtggccgac atccggctga gtccaacaa ctacgagaag      180 cactacgccg agtccgtgaa gggccggttc accatctctc gggacgactc caagaactcc     240
ctgtacctgc agatgaacag cctgaaaacc gaggacaccg ccgtgtacta ctgcatcaga     300
gagggcgact acttcgacta ctggggccag ggcaccaccg tgaccgtcag ctca           354

<210> SEQ ID NO 52

<211> LENGTH: 333
<212> TYPE: DNA
<213> ORGANISM: Artificial Sequence
<220> FEATURE:
<223> OTHER INFORMATION: Synthetic nucleic acid

<400> SEQUENCE: 52

```
gatatcgtgc tgacccagtc tcctgcctcc ctggctgtgt ctcctggcca gagagccacc        60
attacctgca aggcctccga gtccgtggac tccttcggcg ccaccttcat gcactggtat       120
cagcagaagc ccggccagcc ccccaagctg ctgatctacc tggcctccaa cctggaatcc       180
ggcgtgcccg ccagattctc cggctctggc tctggcaccg acttcaccct gaccatcaac       240
cccgtggaag ccaacgacac cgccaactac tactgccagc agaacaacga ggaccnctac       300
accttcggcc agggcaccaa gctggaaatc aag                                    333
```

<210> SEQ ID NO 53
<211> LENGTH: 443
<212> TYPE: PRT
<213> ORGANISM: Artificial Sequence
<220> FEATURE:
<223> OTHER INFORMATION: Synthetic polypeptide

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Leu Asn Trp Val Arg Gln Ala Pro Gly Lys Gly Leu Glu Trp Val
        35                  40                  45

Ala Asp Ile Arg Leu Lys Ser Asn Asn Tyr Glu Lys His Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ile Arg Glu Gly Asp Tyr Phe Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe

```
                     260                 265                 270
Asn Trp Tyr Val Asp Gly Val Glu Val His Asn Ala Lys Thr Lys Pro
            275                 280                 285
Arg Glu Glu Gln Phe Asn Ser Thr Phe Arg Val Val Ser Val Leu Thr
        290                 295                 300
Val Val His Gln Asp Trp Leu Asn Gly Lys Glu Tyr Lys Cys Lys Val
305                 310                 315                 320
Ser Asn Lys Gly Leu Pro Ala Pro Ile Glu Lys Thr Ile Ser Lys Thr
                325                 330                 335
Lys Gly Gln Pro Arg Glu Pro Gln Val Tyr Thr Leu Pro Pro Ser Arg
            340                 345                 350
Glu Glu Met Thr Lys Asn Gln Val Ser Leu Thr Cys Leu Val Lys Gly
        355                 360                 365
Phe Tyr Pro Ser Asp Ile Ala Val Glu Trp Glu Ser Asn Gly Gln Pro
    370                 375                 380
Glu Asn Asn Tyr Lys Thr Thr Pro Pro Met Leu Asp Ser Asp Gly Ser
385                 390                 395                 400
Phe Phe Leu Tyr Ser Lys Leu Thr Val Asp Lys Ser Arg Trp Gln Gln
                405                 410                 415
Gly Asn Val Phe Ser Cys Ser Val Met His Glu Ala Leu His Asn His
            420                 425                 430
Tyr Thr Gln Lys Ser Leu Ser Leu Ser Pro Gly
        435                 440

<210> SEQ ID NO 54
<211> LENGTH: 218
<212> TYPE: PRT
<213> ORGANISM: Artificial Sequence
<220> FEATURE:
<223> OTHER INFORMATION: Synthetic polypeptide

<400> SEQUENCE: 54

Asp Ile Val Leu Thr Gln Ser Pro Ala Ser Leu Ala Val Ser Pro Gly
1               5                   10                  15
Gln Arg Ala Thr Ile Thr Cys Lys Ala Ser Glu Ser Val Asp Ser Phe
            20                  25                  30
Gly Ala Thr Phe Met His Trp Tyr Gln Gln Lys Pro Gly Gln Pro Pro
        35                  40                  45
Lys Leu Leu Ile Tyr Leu Ala Ser Asn Leu Glu Ser Gly Val Pro Ala
    50                  55                  60
Arg Phe Ser Gly Ser Gly Ser Gly Thr Asp Phe Thr Leu Thr Ile Asn
65                  70                  75                  80
Pro Val Glu Ala Asn Asp Thr Ala Asn Tyr Tyr Cys Gln Gln Asn Asn
                85                  90                  95
Glu Asp Pro Tyr Thr Phe Gly Gln Gly Thr Lys Leu Glu Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
```

```
                180             185              190
His Lys Val Tyr Ala Cys Glu Val Thr His Gln Gly Leu Ser Ser Pro
        195                  200                  205

Val Thr Lys Ser Phe Asn Arg Gly Glu Cys
    210                 215
```

<210> SEQ ID NO 55
<211> LENGTH: 1329
<212> TYPE: DNA
<213> ORGANISM: Artificial Sequence
<220> FEATURE:
<223> OTHER INFORMATION: Synthetic nucleic acid

<400> SEQUENCE: 55

| | | |
|---|---|---|
| gaagtgcagc tggtggaatc cggcggaggc ctggtgcagc ctggcggatc tctgagactg | 60 |
| tcttgtgccg cctccggctt caccttctcc aactactacc tgaactgggt gcgacaggcc | 120 |
| cctggcaagg gactggaatg ggtggccgac atccggctga agtccaacaa ctacgagaag | 180 |
| cactacgccg agtccgtgaa gggccggttc accatctctc gggacgactc caagaactcc | 240 |
| ctgtacctgc agatgaacag cctgaaaacc gaggacaccg ccgtgtacta ctgcatcaga | 300 |
| gagggcgact acttcgacta ctggggccag ggcaccaccg tgaccgtcag ctcagcttcc | 360 |
| accaagggcc cctccgtgtt ccctctggcc ccttgctccc ggtccacctc tgagtctacc | 420 |
| gccgctctgg gctgcctggt gaaagactac ttccccgagc ccgtgaccgt gtcctggaac | 480 |
| tctggcgccc tgacctccgg cgtgcacacc tttccagccg tgctgcagtc ctccggcctg | 540 |
| tactccctgt cctccgtggt gacagtgccc tcctccaact cggcaccca gacctacacc | 600 |
| tgtaacgtgg accacaagcc ctccaacacc aaggtggaca gaccgtgga cggaagtgc | 660 |
| tgcgtggaat gccacccctg tcctgctcca cctgtggctg gccccagcgt gttcctgttc | 720 |
| cccccaaagc ccaaggacac cctgatgatc tcccggaccc ccgaagtgac ctgcgtggtg | 780 |
| gtggacgtgt cccacgagga ccccgaggtg cagttcaatt ggtacgtgga cggcgtggaa | 840 |
| gtgcacaacg ccaagaccaa gccagagag gaacagttca actccacctt ccgggtggtg | 900 |
| tccgtgctga ccgtggtgca tcaggactgg ctgaacggca agagtacaa gtgcaaggtc | 960 |
| tccaacaagg gcctgcctgc ccccatcgaa aagaccatca gcaagaccaa gggccagccc | 1020 |
| cgcgagcccc aggtgtacac actgccccc agcggaagg gatgaccaa gaaccaggtg | 1080 |
| tccctgacct gtctggtgaa aggcttctac ccctccgaca ttgccgtgga atgggagtcc | 1140 |
| aacggacagc ctgagaacaa ctacaagacc ccccccccca tgctggactc cgacggctca | 1200 |
| ttcttcctgt actccaagct gacagtggac aagtcccggt ggcagcaggg caacgtgttc | 1260 |
| tcctgctccg tgatgcacga ggccctgcac aaccactaca cccagaagtc cctgtccctg | 1320 |
| agccccggc | 1329 |

<210> SEQ ID NO 56
<211> LENGTH: 654
<212> TYPE: DNA
<213> ORGANISM: Artificial Sequence
<220> FEATURE:
<223> OTHER INFORMATION: Synthetic nucleic acid

<400> SEQUENCE: 56

| | | |
|---|---|---|
| gatatcgtgc tgacccagtc tcctgcctcc ctggctgtgt ctcctggcca gagagccacc | 60 |
| attacctgca aggcctccga gtccgtggac tccttcggcg ccaccttcat gcactggtat | 120 |
| cagcagaagc ccggccagcc ccccaagctg ctgatctacc tggcctccaa cctggaatcc | 180 |

```
ggcgtgcccg ccagattctc cggctctggc tctggcaccg acttcaccct gaccatcaac    240
cccgtggaag ccaacgacac cgccaactac tactgccagc agaacaacga ggacccctac    300
accttcggcc agggcaccaa gctggaaatc aagcggaccg tggccgctcc ctccgtgttt    360
atcttcccac cctccgacga gcagctgaag tccggcacag cttccgtcgt gtgcctgctg    420
aacaacttct accctcggga agccaaggtg cagtggaagg tggacaacgc cctgcagtcc    480
ggcaactccc aggaatccgt gaccgagcag gactccaagg acagcaccta ctccctgtcc    540
tctaccctga ccctgtccaa ggccgactac gagaagcaca aggtgtacgc ctgcgaagtg    600
acccaccagg gcctgtctag ccccgtgacc aagtctttca accggggcga gtgt          654
```

<210> SEQ ID NO 57
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 57

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Leu Asn Trp Val Arg Gln Ala Pro Gly Lys Gly Leu Glu Trp Val
        35                  40                  45

Ala Asp Ile Arg Leu Lys Ser Asn Asn Tyr Glu Lys His Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ile Arg Glu Gly Asp Tyr Phe Asp Tyr Trp Gly Gln Gly Thr
            100                 105                 110

Thr Val Thr Val Ser Ser
        115
```

<210> SEQ ID NO 58
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 58

```
Asn Tyr Tyr Leu Asn
1               5
```

<210> SEQ ID NO 59
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 59

```
Asp Ile Arg Leu Lys Ser Asn Asn Tyr Glu Lys His Tyr Ala Glu Ser
1               5                   10                  15

Val Lys Gly
```

<210> SEQ ID NO 60
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 60

Ile Arg Glu Gly Asp Tyr Phe Asp Tyr
1               5

<210> SEQ ID NO 61
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 61

Asp Ile Val Met Thr Gln Thr Pro Leu Ser Leu Ser Val Thr Pro Gly
1               5                   10                  15

Gln Pro Ala Ser Ile Ser Cys Lys Ala Ser Glu Ser Val Asp Ser Phe
            20                  25                  30

Gly Ala Thr Phe Met His Trp Tyr Leu Gln Lys Pro Gly Gln Pro Pro
        35                  40                  45

Gln Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Asn Asn
                85                  90                  95

Glu Asp Pro Tyr Thr Phe Gly Gln Gly Thr Lys Leu Glu Ile Lys
            100                 105                 110

<210> SEQ ID NO 62
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 62

Lys Ala Ser Glu Ser Val Asp Ser Phe Gly Ala Thr Phe Met His
1               5                   10                  15

<210> SEQ ID NO 63
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 63

Leu Ala Ser Asn Leu Glu Ser
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 64

```
Gln Gln Asn Asn Glu Asp Pro Tyr Thr
1               5
```

<210> SEQ ID NO 65
<211> LENGTH: 354
<212> TYPE: DNA
<213> ORGANISM: Artificial Sequence
<220> FEATURE:
<223> OTHER INFORMATION: Synthetic nucleic acid

<400> SEQUENCE: 65

```
gaagtgcagc tggtggaatc cggcggaggc ctggtgcagc ctggcggatc tctgagactg      60
tcttgtgccg cctccggctt caccttctcc aactactacc tgaactgggt gcgacaggcc     120
cctggcaagg gactggaatg ggtggccgac atccggctga agtccaacaa ctacgagaag     180
cactacgccg agtccgtgaa gggccggttc accatctctc gggacgactc caagaactcc     240
ctgtacctgc agatgaacag cctgaaaacc gaggacaccg ccgtgtacta ctgcatcaga     300
gagggcgact acttcgacta ctggggccag ggcaccaccg tgaccgtgag ctca           354
```

<210> SEQ ID NO 66
<211> LENGTH: 333
<212> TYPE: DNA
<213> ORGANISM: Artificial Sequence
<220> FEATURE:
<223> OTHER INFORMATION: Synthetic nucleic acid

<400> SEQUENCE: 66

```
gacatcgtga tgacccagac ccctctgtcc ctgtccgtga cccctggaca gcctgcctcc      60
atctcctgca aggcctccga gtccgtggac tctttcggcg ccaccttcat gcactggtat     120
ctgcagaagc ccggccagcc ccctcagctg ctgatctacc tggcctccaa cctggaatcc     180
ggcgtgcccg acagattctc cggctctggc tctggcaccg acttcaccct gaagatctcc     240
cgggtggaag ccgaggacgt gggcgtgtac tactgccagc agaacaacga ggaccectac     300
accttcggcc agggcaccaa gctggaaatc aag                                  333
```

<210> SEQ ID NO 67
<211> LENGTH: 443
<212> TYPE: PRT
<213> ORGANISM: Artificial Sequence
<220> FEATURE:
<223> OTHER INFORMATION: Synthetic polypeptide

<400> SEQUENCE: 67

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Leu Asn Trp Val Arg Gln Ala Pro Gly Lys Gly Leu Glu Trp Val
        35                  40                  45

Ala Asp Ile Arg Leu Lys Ser Asn Asn Tyr Glu Lys His Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ile Arg Glu Gly Asp Tyr Phe Asp Tyr Trp Gly Gln Gly Thr
            100                 105                 110
```

Thr Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
        435                 440

<210> SEQ ID NO 68
<211> LENGTH: 218
<212> TYPE: PRT
<213> ORGANISM: Artificial Sequence
<220> FEATURE:
<223> OTHER INFORMATION: Synthetic polypeptide

<400> SEQUENCE: 68

Asp Ile Val Met Thr Gln Thr Pro Leu Ser Leu Ser Val Thr Pro Gly
1               5                   10                  15

Gln Pro Ala Ser Ile Ser Cys Lys Ala Ser Glu Ser Val Asp Ser Phe
            20                  25                  30

Gly Ala Thr Phe Met His Trp Tyr Leu Gln Lys Pro Gly Gln Pro Pro
                35                  40                  45

Gln Leu Leu Ile Tyr Leu Ala Ser Asn Leu Glu Ser Gly Val Pro Asp
 50                  55                  60

Arg Phe Ser Gly Ser Gly Ser Gly Thr Asp Phe Thr Leu Lys Ile Ser
 65                  70                  75                  80

Arg Val Glu Ala Glu Asp Val Gly Val Tyr Tyr Cys Gln Gln Asn Asn
                 85                  90                  95

Glu Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
210                 215

<210> SEQ ID NO 69
<211> LENGTH: 1329
<212> TYPE: DNA
<213> ORGANISM: Artificial Sequence
<220> FEATURE:
<223> OTHER INFORMATION: Synthetic nucleic acid

<400> SEQUENCE: 69

```
gaagtgcagc tggtggaatc cggcggaggc ctggtgcagc ctggcggatc tctgagactg      60
tcttgtgccg cctccggctt cacctttctc aactactacc tgaactgggt gcgacaggcc     120
cctggcaagg gactggaatg ggtggccgac atccggctga agtccaacaa ctacgagaag     180
cactacgccg agtccgtgaa gggccggttc accatctctc gggacgactc caagaactcc     240
ctgtacctgc agatgaacag cctgaaaacc gaggacaccg ccgtgtacta ctgcatcaga     300
gagggcgact acttcgacta ctggggccag ggcaccaccg tgaccgtgag ctcagcttcc     360
accaagggcc cctccgtgtt ccctctggcc ccttgctccc ggtccacctc tgagtctacc     420
gccgctctgg gctgcctggt gaaagactac ttccccgagc ccgtgaccgt gtcctggaac     480
tctggcgccc tgacctccgg cgtgcacacc tttccagccg tgctgcagtc ctccggcctg     540
tactccctgt cctccgtggt gacagtgccc tcctccaact ccggcaccca gacctacacc     600
tgtaacgtgg accacaagcc ctccaacacc aaggtggaca gaccgtgga cggaagtgc      660
tgcgtggaat gccaccctg tcctgctcca cctgtggctg gccccagcgt gttcctgttc     720
cccccaaagc ccaaggacac cctgatgatc tcccggaccc ccgaagtgac ctgcgtggtg     780
gtggacgtgt cccacgagga cccgaggtg cagttcaatt ggtacgtgga cggcgtggaa     840
gtgcacaacg ccaagaccaa gcccagagag aacagttca actccaccttc cgggtggtg      900
tccgtgctga ccgtgtgca tcaggactgg ctgaacggca agagtacaa gtgcaaggtc     960
tccaacaagg cctgcctgc ccccatcgaa aagaccatca gcaagaccaa gggccagccc    1020
```

```
cgcgagcccc aggtgtacac actgccccc agccgggaag agatgaccaa gaaccaggtg    1080
tccctgacct gtctggtgaa aggcttctac ccctccgaca ttgccgtgga atgggagtcc    1140
aacggacagc ctgagaacaa ctacaagacc ccccccca tgctggactc cgacggctca     1200
ttcttcctgt actccaagct gacagtggac aagtcccggt ggcagcaggg caacgtgttc    1260
tcctgctccg tgatgcacga ggccctgcac aaccactaca cccagaagtc cctgtccctg    1320
agccccggc                                                           1329
```

<210> SEQ ID NO 70
<211> LENGTH: 654
<212> TYPE: DNA
<213> ORGANISM: Artificial Sequence
<220> FEATURE:
<223> OTHER INFORMATION: Synthetic nucleic acid

<400> SEQUENCE: 70

```
gacatcgtga tgacccagac ccctctgtcc ctgtccgtga cccctggaca gcctgcctcc     60
atctcctgca aggcctccga gtccgtggac tctttcggcg ccaccttcat gcactggtat    120
ctgcagaagc ccggccagcc ccctcagctg ctgatctacc tggcctccaa cctggaatcc    180
ggcgtgcccg acagattctc cggctctggc tctggcaccg acttcaccct gaagatctcc    240
cgggtggaag ccgaggacgt gggcgtgtac tactgcgcag agaacaacga ggacccctac    300
accttcggcc agggcaccaa gctggaaatc aagcggaccg tggccgctcc ctccgtgttt    360
atcttcccac cctccgacga gcagctgaag tccggcacag cttccgtcgt gtgcctgctg    420
aacaacttct accccgcga ggccaaggtg cagtggaagg tggacaacgc cctgcagtcc    480
ggcaactccc aggaatccgt gaccgagcag gactccaagg acagcaccta ctccctgtcc    540
tccaccctga cccctgtccaa ggccgactac gagaagcaca aggtgtacgc ctgcgaagtg    600
acccaccagg gcctgtctag ccccgtgacc aagtctttca ccggggcga gtgt            654
```

<210> SEQ ID NO 71
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 71

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Asn Trp Val Arg Gln Ala Pro Gly Lys Gly Leu Glu Trp Val
        35                  40                  45

Ser Asp Ile Arg Leu Lys Ser Asn Asn Tyr Glu Lys His Tyr Ala Asp
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Glu Gly Asp Tyr Phe Asp Tyr Trp Gly Gln Gly Thr
            100                 105                 110

Leu Val Thr Val Ser Ser
        115

<210> SEQ ID NO 72
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 72

Ser Tyr Tyr Met Asn
1               5

<210> SEQ ID NO 73
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 73

Asp Ile Arg Leu Lys Ser Asn Asn Tyr Glu Lys His Tyr Ala Asp Ser
1               5                   10                  15

Val Lys Gly

<210> SEQ ID NO 74
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 74

Ala Arg Glu Gly Asp Tyr Phe Asp Tyr
1               5

<210> SEQ ID NO 75
<211> LENGTH: 354
<212> TYPE: DNA
<213> ORGANISM: Artificial Sequence
<220> FEATURE:
<223> OTHER INFORMATION: Synthetic nucleic acid

<400> SEQUENCE: 75
gaagtgcagc tggtggaatc cggcggaggc ctggtgcagc ctggcggatc tctgagactg      60
tcttgtgccg cctccggctt caccttctcc agctactaca tgaactgggt gcgacaggcc     120
cctggcaagg gcctggaatg ggtgtccgac atccggctga gtccaacaa ctacgagaag      180 cactacgccg actccgtgaa gggccggttc accatcagcc gggacaacgc caagaactcc     240
ctgtacctgc agatgaacag cctgcgggcc gaggacaccg ccgtgtacta ctgtgctaga     300
gagggcgact acttcgacta ctggggccag ggcacccteg tgaccgtgag ctca            354

<210> SEQ ID NO 76
<211> LENGTH: 333
<212> TYPE: DNA
<213> ORGANISM: Artificial Sequence
<220> FEATURE:
<223> OTHER INFORMATION: Synthetic nucleic acid

<400> SEQUENCE: 76
gatatcgtgc tgacccagac ccctctgtcc ctgtctgtga ccctggccca gcctgcctcc      60
atctcctgta gagcctccga gtccgtggac tccttcggcg ccaccttcat gcactggtat     120
ctgcagaagc ccggccagcc ccctcagctg ctgatctacc tggcctccaa cctggaatcc     180

```
ggcgtgcccg acagattctc cggctctggc tctggcaccg acttcaccct gaagatctcc      240
cgggtggaag ccgaggacgt gggcgtgtac tactgccagc agaacaacga ggacccctac      300
accttcggcc agggcaccaa gctggaaatc aag                                   333
```

<210> SEQ ID NO 77
<211> LENGTH: 443
<212> TYPE: PRT
<213> ORGANISM: Artificial Sequence
<220> FEATURE:
<223> OTHER INFORMATION: Synthetic polypeptide

<400> SEQUENCE: 77

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Asn Trp Val Arg Gln Ala Pro Gly Lys Gly Leu Glu Trp Val
        35                  40                  45

Ser Asp Ile Arg Leu Lys Ser Asn Asn Tyr Glu Lys His Tyr Ala Asp
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Glu Gly Asp Tyr Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335
```

```
Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
        435                 440

<210> SEQ ID NO 78
<211> LENGTH: 218
<212> TYPE: PRT
<213> ORGANISM: Artificial Sequence
<220> FEATURE:
<223> OTHER INFORMATION: Synthetic polypeptide

<400> SEQUENCE: 78

Asp Ile Val Leu Thr Gln Thr Pro Leu Ser Leu Ser Val Thr Pro Gly
1               5                   10                  15

Gln Pro Ala Ser Ile Ser Cys Arg Ala Ser Glu Ser Val Asp Ser Phe
            20                  25                  30

Gly Ala Thr Phe Met His Trp Tyr Leu Gln Lys Pro Gly Gln Pro Pro
        35                  40                  45

Gln Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Asn Asn
                85                  90                  95

Glu Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 79
<211> LENGTH: 1329
<212> TYPE: DNA
<213> ORGANISM: Artificial Sequence
<220> FEATURE:
```

<223> OTHER INFORMATION: Synthetic nucleic acid

<400> SEQUENCE: 79

```
gaagtgcagc tggtggaatc cggcggaggc ctggtgcagc tggcggatc tctgagactg      60
tcttgtgccg cctccggctt caccttctcc agctactaca tgaactgggt gcgacaggcc    120
cctggcaagg gcctggaatg ggtgtccgac atccggctga agtccaacaa ctacgagaag    180
cactacgccg actccgtgaa gggccggttc accatcagcc gggacaacgc caagaactcc    240
ctgtacctgc agatgaacag cctgcgggcc gaggacaccg ccgtgtacta ctgtgctaga    300
gagggcgact acttcgacta ctggggccag ggcaccctcg tgaccgtgag ctcagcttcc    360
accaagggcc cctccgtgtt ccctctggcc ccttgctccc ggtccacctc tgagtctacc    420
gccgctctgg gctgcctggt gaaagactac ttccccgagc ccgtgaccgt gtcctggaac    480
tctggcgccc tgacctccgg cgtgcacacc tttccagccg tgctgcagtc ctccggcctg    540
tactccctgt cctccgtggt gacagtgccc tcctccaact tcggcaccca gacctacacc    600
tgtaacgtgg accacaagcc ctccaacacc aaggtggaca gaccgtggga acggaagtgc    660
tgcgtggaat gcccaccctg tcctgctcca cctgtggctg ccccagcgt gttcctgttc     720
cccccaaagc ccaaggacac cctgatgatc tcccggaccc ccgaagtgac ctgcgtggtg    780
gtggacgtgt cccacgagga cccgaggtg cagttcaatt ggtacgtgga cggcgtggaa    840
gtgcacaacg ccaagaccaa gcccagagag gaacagttca actccacctt ccgggtggtg    900
tccgtgctga ccgtggtgca tcaggactgg ctgaacggca agagtacaa gtgcaaggtc     960
tccaacaagg gcctgcctgc ccccatcgaa aagaccatca gcaagaccaa gggccagccc   1020
cgcgagcccc aggtgtacac actgccccca gccgggaag agatgaccaa gaaccaggtg   1080
tccctgacct gtctggtgaa aggcttctac ccctccgaca ttgccgtgga atgggagtcc    1140
aacggacagc ctgagaacaa ctacaagacc accccccca tgctggactc cgacggctca   1200
ttcttcctgt actccaagct gacagtggac aagtcccggt ggcagcaggg caacgtgttc   1260
tcctgctccg tgatgcacga ggccctgcac aaccactaca cccagaagtc cctgtccctg   1320
agccccggc                                                             1329
```

<210> SEQ ID NO 80
<211> LENGTH: 654
<212> TYPE: DNA
<213> ORGANISM: Artificial Sequence
<220> FEATURE:
<223> OTHER INFORMATION: Synthetic nucleic acid

<400> SEQUENCE: 80

```
gatatcgtgc tgacccagac ccctctgtcc ctgtctgtga cccctggcca gcctgcctcc     60
atctcctgta gagcctccga gtccgtggac tccttcggcg ccaccttcat gcactggtat    120
ctgcagaagc ccggccagcc ccctcagctg ctgatctacc tggcctccaa cctggaatcc    180
ggcgtgcccg acagattctc cggctctggc tctggcaccg acttcaccct gaagatctcc    240
cgggtggaag ccgaggacgt gggcgtgtac tactgccagc agaacaacga ggaccctac     300
accttcggcc agggcaccaa gctggaaatc aagcggaccg tggccgctcc ctccgtgttt    360
atcttcccac cctccgacga gcagctgaag tccggcacag cttccgtcgt gtgcctgctg    420
aacaacttct accccgcga ggccaaggtg cagtggaagg tggacaacgc cctgcagtcc    480
ggcaactccc aggaatccgt gaccgagcag gactccaagg acagcaccta ctccctgtcc    540
tccaccctga cctgtccaa ggccgactac gagaagcaca aggtgtacgc ctgcgaagtg    600
```

```
acccaccagg gcctgtctag ccccgtgacc aagtctttca accggggcga gtgt      654
```

```
<210> SEQ ID NO 81
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 81
```

Asp Ile Val Leu Thr Gln Thr Pro Leu Ser Leu Ser Val Thr Pro Gly
1               5                   10                  15

Gln Pro Ala Ser Ile Ser Cys Arg Ala Ser Glu Ser Val Asp Ser Phe
            20                  25                  30

Gly Ala Thr Phe Met His Trp Tyr Leu Gln Lys Pro Gly Gln Pro Pro
        35                  40                  45

Gln Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Asn Asn
                85                  90                  95

Glu Asp Pro Tyr Thr Phe Gly Gln Gly Thr Lys Leu Glu Ile Lys
            100                 105                 110

```
<210> SEQ ID NO 82
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 82
```

Arg Ala Ser Glu Ser Val Asp Ser Phe Gly Ala Thr Phe Met His
1               5                   10                  15

```
<210> SEQ ID NO 83
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 83
```

Leu Ala Ser Asn Leu Glu Ser
1               5

```
<210> SEQ ID NO 84
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 84
```

Gln Gln Asn Asn Glu Asp Pro Tyr Thr
1               5

UNITED STATES PATENT AND TRADEMARK OFFICE
CERTIFICATE OF CORRECTION

PATENT NO. : 11,077,187 B2
APPLICATION NO. : 15/775056
DATED : August 3, 2021
INVENTOR(S) : Zhao et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 178 days.

Signed and Sealed this
Thirty-first Day of January, 2023

*Katherine Kelly Vidal*
Katherine Kelly Vidal
*Director of the United States Patent and Trademark Office*